(12) United States Patent
Kufer et al.

(10) Patent No.: US 7,632,925 B2
(45) Date of Patent: Dec. 15, 2009

(54) ANTIBODIES THAT BIND HUMAN 17-A1/EPCAM TUMOR ANTIGEN

(75) Inventors: Peter Kufer, Moosburg (DE); Tobias Raum, Munich (DE)

(73) Assignee: Micromet AG, Munich (DE)

( * ) Notice: Subject to any disclaimer, the term of this patent is extended or adjusted under 35 U.S.C. 154(b) by 165 days.

(21) Appl. No.: 11/860,242

(22) Filed: Sep. 24, 2007

(65) Prior Publication Data

US 2009/0081191 A1 Mar. 26, 2009

Related U.S. Application Data

(60) Continuation of application No. 10/325,694, filed on Dec. 19, 2002, now abandoned, which is a division of application No. 09/403,107, filed as application No. PCT/EP98/02180 on Apr. 14, 1998, now Pat. No. 7,227,002.

(30) Foreign Application Priority Data

Apr. 14, 1997 (EP) .................................. 97106109

(51) Int. Cl.
C12P 21/08 (2006.01)
C07K 16/00 (2006.01)
A61K 39/395 (2006.01)
C12P 21/04 (2006.01)
C07H 21/04 (2006.01)

(52) U.S. Cl. ............................... 530/387.3; 530/388.15; 530/388.85; 530/391.3; 530/391.7; 424/133.1; 424/142.1; 424/156.1; 424/174.1; 424/181.1; 424/183.1; 435/69.6; 536/23.53

(58) Field of Classification Search .................. None
See application file for complete search history.

(56) References Cited

U.S. PATENT DOCUMENTS

| 5,565,332 A | 10/1996 | Hoogenboom et al. ..... 435/69.1 |
| 5,885,793 A | 3/1999 | Griffiths et al. ............ 435/69.1 |
| 6,150,584 A | 11/2000 | Kucherlapati et al. ......... 800/18 |

FOREIGN PATENT DOCUMENTS

| WO | WO 93/06213 | 4/1993 |
| WO | WO 93/11236 | 6/1993 |
| WO | WO 97/00271 | 1/1997 |

OTHER PUBLICATIONS

Amin and Carter, "Immunogenicity issues with therapeutic protein," Curr Drug Disc, Nov. 20- 24, 2004.

Dermer, "Another anniversary for the war on cancer," Bio/Technology, 12:320, 1994.
Duenas et al., "In vitro immunization of naïve human B cells yeilds high affinity immunoglublin G antibodies as illustrated by phage display," Immunology, 89:1-7, 1996.
Figini et al., "In Vitro Assembly of Repertoires of Antibody Chains on the Surface of Phage Renaturation," J. Mol. Biol., 269:68-78, 1994.
Freshney, Culture of animal cells: a manual of basic technique, Alan R. Liss, Inc., New York p. 4, 1983.
Gottlinger et al., "The epithelial cell surface antigen 17-1A, a target for antibody-medicated tumor therapy: its biochemical nature, tissue distribution and recognition by different monoclonal antibodies," Intl. Journ. Cancer, 38:47-53, 1986.
Gura, "Systems for identifying new drugs are often faulty," Science, 278:1041-1042, 1997.
Herlyn and Koprowski, "IgG2a monoclonal antibodies inhibit human tumor growth through interaction with effector cells," Proc Natl Acad Sci USA, 79:4761-4765, 1982.
Herlyn et al., "Colorectal carcinoma-specific antigen: detection by means of monoclonal antibodies," Proc Natl Acad Sci USA,76(3):1438-1442, 1979.
Hoess et al., "Generation of human antibodies that selectively recognize diseased cells overexpressing surface bound antigens," Proc. Americ. Ass. Canc. Re., 38:30, 1997.
Jain, "Barriers to drug delivery in solid tumors," Sci Am, 271(1):58-65, 1994.
Krebber et al., "Reliable cloning of functional antibody variable domains from hybridomas and spleen cell repertoire employing a reengineered phage display system," Journ. Immunological Methods, 201:35-35, 1997.
Litvinov et al., "Ep-CAM: a human epithelial antigen is a homophilic cell-cell adhesion molecule," J Cell Biol, 125(2):437-446, 1994.
LoBuglio et al., "Mouse/human chimeric monoclonal antibody antibody in man: Kinetic and immune response," Proc. Natl. Acad. Sci. USA, 86:4220-4224, 1989.
Marks et al., "By-passing Immunization Human Antibodies from V-gene Libraries Displayed on Phage," J. Mol. Biol., 222:581-597, 1991.
Rudikoff et al., "Single amino acid substitution altering antigen-binding specificity," Proc. Natl. Acad. Sci. USA, 79:1979-1983, 1982.
Sun et al., "Chimeric antibody with human constant regions and mouse variable regions directed against carcinoma-associated antigen 17-1A," Proc. Natl. Acad. Sci. 84:214-218, 1987.
Szala et al., "Molecular cloning of cDNA for the carcinoma-associated antigen GA733-2," Proc. Natl. Acad. Sci. USA, 87:3542-3546, 1990.
William, Fundamental Immunology, 3rd Edition, pp. 292-295, 1993.
Winter et al., "Making antibodies by phage display technology," Annu Rev Immunol, 12:433-455, 1994.

Primary Examiner—David J. Blanchard
(74) Attorney, Agent, or Firm—Fulbright & Jaworski

(57) ABSTRACT

The present invention provides an anti-human antibody or fragment thereof that is low or not immunogenic in humans. In particular, the antibodies or fragments are directed to human tumor antigens, preferably to the human tumor antigen 17-1A, also known as EpCAM, EGP or GA 733-2. Also provided are pharmaceutical compositions comprising the aforementioned antibodies or fragments thereto.

10 Claims, 35 Drawing Sheets

File Name : D4.5-k8-VL

Fig. 6

Figure 1:
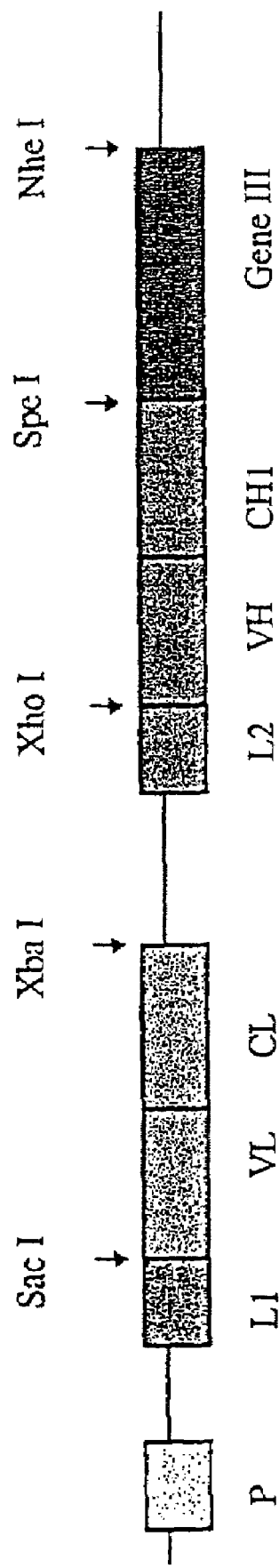

```
              9                 18                27                36                45                54
5' GAG CTC CAG ATG ACC CAG TCT CCA TCC TCC CTG TCT GCT TCT GTG GGA GAC AGA
   --- --- --- --- --- --- --- --- --- --- --- --- --- --- --- --- --- ---
    E   L   Q   M   T   Q   S   P   S   S   L   S   A   S   V   G   D   R 63                72                81                90                99               108
   GTC ACC ATC ACT TGT CGG ACA AGT CAG AGC ATT AGC AGC TAT TTA AAT TGG TAT
   --- --- --- --- --- --- --- --- --- --- --- --- --- --- --- --- --- ---
    V   T   I   T   C   R   T   S   Q   S   I   S   S   Y   L   N   W   Y 117               126               135               144               153               162
   CAG CAG AAA CCA GGA CAG CCT CCT AAG CTG CTC ATT TAC TGG GCA TCT ACC CGG
   --- --- --- --- --- --- --- --- --- --- --- --- --- --- --- --- --- ---
    Q   Q   K   P   G   Q   P   P   K   L   L   I   Y   W   A   S   T   R 171               180               189               198               207               216
   GAA TCC GGG GTC CCT GAC CGA TTC AGT GGC AGC GGG TCT GGG ACA GAT TTC ACT
   --- --- --- --- --- --- --- --- --- --- --- --- --- --- --- --- --- ---
    E   S   G   V   P   D   R   F   S   G   S   G   S   G   T   D   F   T 225               234               243               252               261               270
   CTC ACC ATC AGC AGT CTA CAA CCT GAA GAT TCT GCA ACT TAC TAC TGT CAG CAG
   --- --- --- --- --- --- --- --- --- --- --- --- --- --- --- --- --- ---
    L   T   I   S   S   L   Q   P   E   D   S   A   T   Y   Y   C   Q   Q 279               288               297               306               315
   AGT TAC GAC ATC CCG TAC ACT TTT GGC CAG GGG ACC AAG CTG GAG ATC AAA 3'
   --- --- --- --- --- --- --- --- --- --- --- --- --- --- --- --- ---
    S   Y   D   I   P   Y   T   F   G   Q   G   T   K   L   E   I   K
```

D4.5:
File Name : D4.5-k8-VH

Fig. 7

```
                9               18              27              36              45              54
5'  GAG GTG CAG CTG CTC GAG TCT GGG GGA GGC GTG GTC CAG CCT GGG AGG TCC CTG
    --- --- --- --- --- --- --- --- --- --- --- --- --- --- --- --- --- ---
     E   V   Q   L   L   E   S   G   G   G   V   V   Q   P   G   R   S   L 63              72              81              90              99             108
    AGA CTC TCC TGT GCA GCC TCT GGA TTC ACC TTC AGT AGC TAT GGC ATG CAC TGG
    --- --- --- --- --- --- --- --- --- --- --- --- --- --- --- --- --- ---
     R   L   S   C   A   A   S   G   F   T   F   S   S   Y   G   M   H   W 117             126             135             144             153             162
    GTC CGC CAG GCT CCA GGC AAG GGG CTG GAG TGG GTG GCA GTT ATA TCA TAT GAT
    --- --- --- --- --- --- --- --- --- --- --- --- --- --- --- --- --- ---
     V   R   Q   A   P   G   K   G   L   E   W   V   A   V   I   S   Y   D 171             180             189             198             207             216
    GGA AGT AAT AAA TAC TAT GCA GAC TCC GTG AAG GGC CGA TTC ACC ATC TCC AGA
    --- --- --- --- --- --- --- --- --- --- --- --- --- --- --- --- --- ---
     G   S   N   K   Y   Y   A   D   S   V   K   G   R   F   T   I   S   R 225             234             243             252             261             270
    GAC AAT TCC AAG AAC ACG CTG TAT CTG CAA ATG AAC AGC CTG AGA GCT GAG GAC
    --- --- --- --- --- --- --- --- --- --- --- --- --- --- --- --- --- ---
     D   N   S   K   N   T   L   Y   L   Q   M   N   S   L   R   A   E   D 279             288             297             306             315             324
    ACG GCT GTG TAT TAC TGT GCG AAA GAT ATG GGG TGG GGC AGT GGC TGG AGA CCC
    --- --- --- --- --- --- --- --- --- --- --- --- --- --- --- --- --- ---
     T   A   V   Y   Y   C   A   K   D   M   G   W   G   S   G   W   R   P 333             342             351             360             369             378
    TAC TAC TAC TAC GGT ATG GAC GTC TGG GGC CAA GGG ACC ACG GTC ACC GTC TCC
    --- --- --- --- --- --- --- --- --- --- --- --- --- --- --- --- --- ---
     Y   Y   Y   Y   G   M   D   V   W   G   Q   G   T   T   V   T   V   S 387             396             405             414
    TCA GCA CCC ACC AAG GCT CCG GAT GTG TTC CCT CTA 3'
    --- --- --- --- --- --- --- --- --- --- --- ---
     S   A   P   T   K   A   P   D   V   F   P   L
```

File Name : D7.2-k8-VH      Fig. 8

```
                9               18              27              36              45              54
5' GAG GTG CAG CTG CTC GAG TCT GGG GGA GTC GTG GTA CAG CCT GGG GGG TCC CTG
    E   V   Q   L   L   E   S   G   G   V   V   V   Q   P   G   G   S   L 63              72              81              90              99             108
   AGA CTC TCC TGT GCA GCC TCT GGA TTC ACC TTT GAT GAT TAT GCC ATG CAC TGG
    R   L   S   C   A   A   S   G   F   T   F   D   D   Y   A   M   H   W 117             126             135             144             153             162
   GTC CGC CAG GCT CCA GGC AAG GGG CTG GAG TGG GTG GCA GTT ATA TCA TAT GAT
    V   R   Q   A   P   G   K   G   L   E   W   V   A   V   I   S   Y   D 171             180             189             198             207             216
   GGA AGT AAT AAA TAC TAT GCA GAC TCC GTG AAG GGC CGA TTC ACC ATC TCC AGA
    G   S   N   K   Y   Y   A   D   S   V   K   G   R   F   T   I   S   R 225             234             243             252             261             270
   GAC AAT TCC AAG AAC ACG CTG TAT CTG CAA ATG AAC AGC CTG AGA GCT GAG GAC
    D   N   S   K   N   T   L   Y   L   Q   M   N   S   L   R   A   E   D 279             288             297             306             315             324
   ACG GCT GTG TAT TAC TGT GCG AAA AAG GAA GGC TAC TGG GGC CAG GGA ACC CTG
    T   A   V   Y   Y   C   A   K   K   E   G   Y   W   G   Q   G   T   L 333             342             351             360             369
   GTC ACC GTC TCC TCA GCA CCC ACC AAG GCT CCG GAT GTG TTC CCT CTA 3'
    V   T   V   S   S   A   P   T   K   A   P   D   V   F   P   L
```

Fig. 9 k5.1

File Name : kappa5.1/11.97

```
              9           18          27          36          45          54
5' GAG CTC CAG ATG ACC CAG TCT CCA TCC TCC CTG TCT GCA TCT GTA GGA GAC AGA
   --- --- --- --- --- --- --- --- --- --- --- --- --- --- --- --- --- ---
    E   L   Q   M   T   Q   S   P   S   S   L   S   A   S   V   G   D   R 63          72          81          90          99         108
   GTC ACC ATC ACT TGC CGG GCA AGT CAG AGC ATT AGC AGC TAT TTA AAT TGG TAT
   --- --- --- --- --- --- --- --- --- --- --- --- --- --- --- --- --- ---
    V   T   I   T   C   R   A   S   Q   S   I   S   S   Y   L   N   W   Y 117         126         135         144         153         162
   CAG CAG AAA CCA GGA CAG CCT CCT AAG CTG CTC ATT TAC TGG GCA TCT ACC CGG
   --- --- --- --- --- --- --- --- --- --- --- --- --- --- --- --- --- ---
    Q   Q   K   P   G   Q   P   P   K   L   L   I   Y   W   A   S   T   R 171         180         189         198         207         216
   GAA TCC GGG GTC CCT GAC CGA TTC AGC GGC AGT GAA TCT GGG ACA AAT TAC ACT
   --- --- --- --- --- --- --- --- --- --- --- --- --- --- --- --- --- ---
    E   S   G   V   P   D   R   F   S   G   S   E   S   G   T   N   Y   T 225         234         243         252         261         270
   CTC ACC ATC AGC AGC CTG CAG CCT GAA GAT TTT GCT ACT TAC TTT TGT CAA CAG
   --- --- --- --- --- --- --- --- --- --- --- --- --- --- --- --- --- ---
    L   T   I   S   S   L   Q   P   E   D   F   A   T   Y   F   C   Q   Q 279         288         297         306         315         324
   TCT GAC AGT TTG CCG ATC ACC TTC GGC CAA GGG ACA CGA CTG GAC ATT CAA 3'
   --- --- --- --- --- --- --- --- --- --- --- --- --- --- --- --- ---
    S   D   S   L   P   I   T   F   G   Q   G   T   R   L   D   I   Q
```

FIG. 16
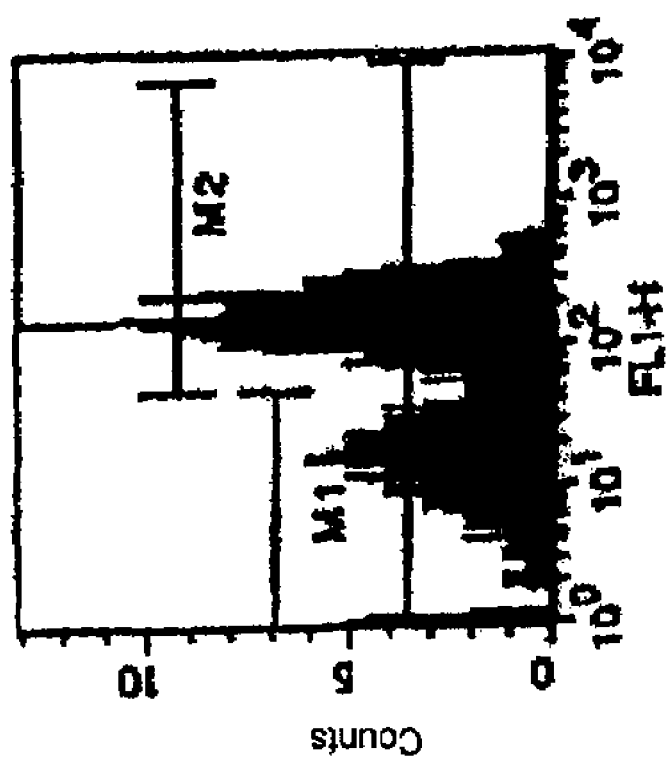
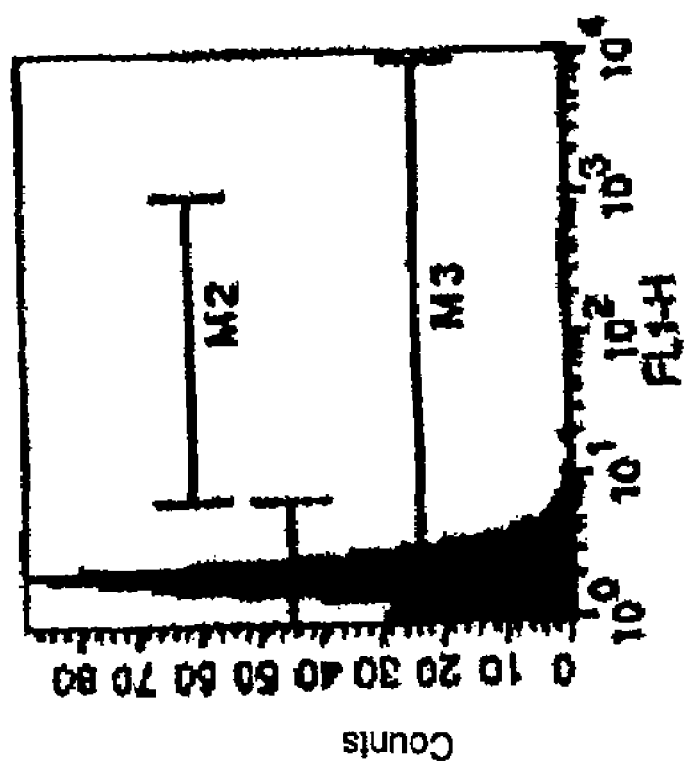

FIG. 16 (cont.)
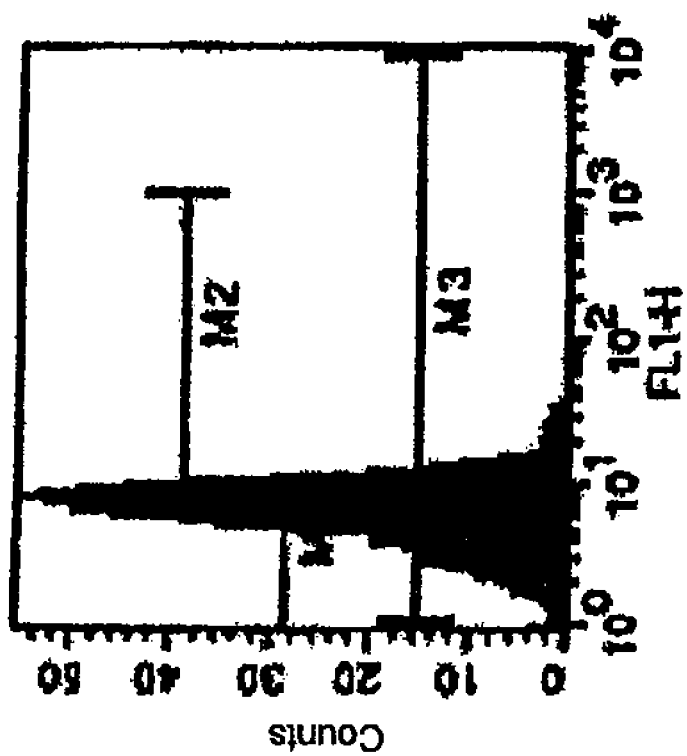
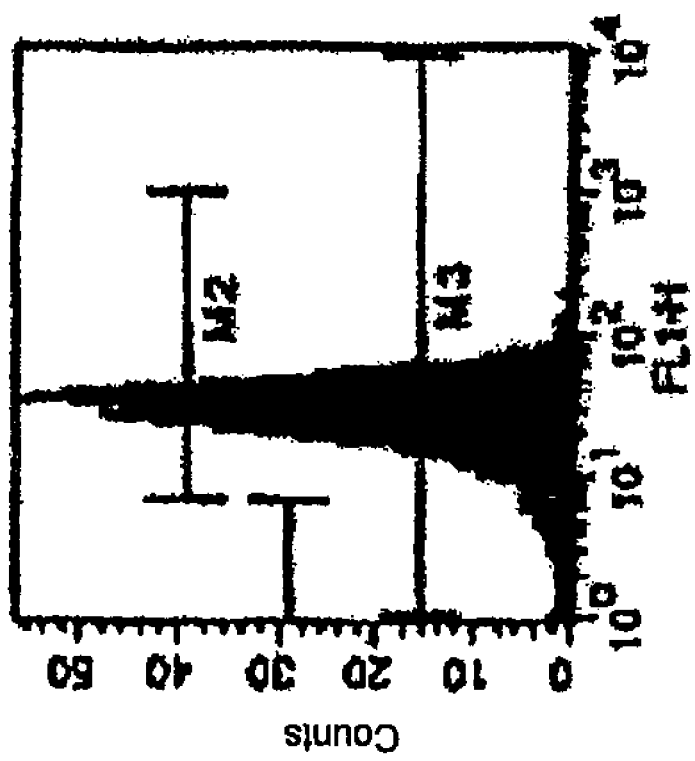

FIG. 16 (cont.)
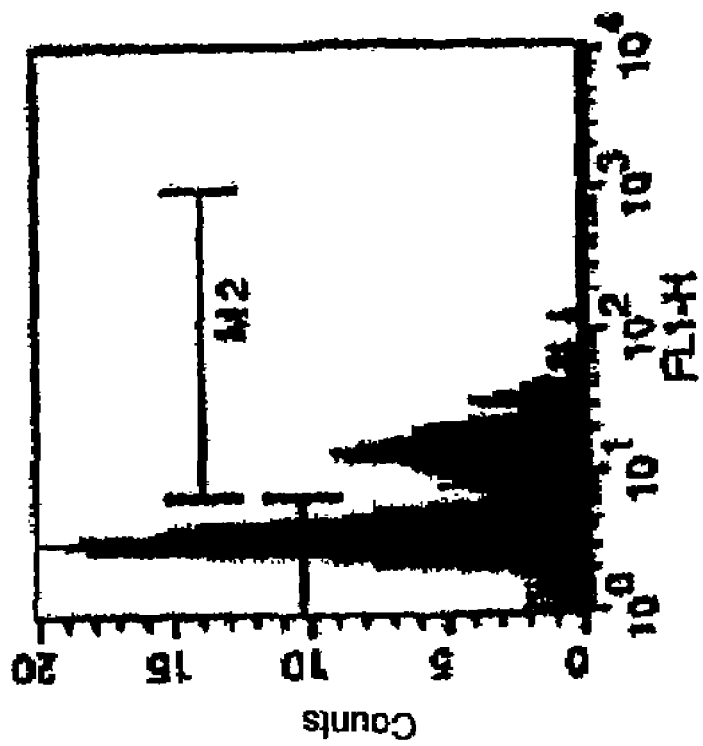
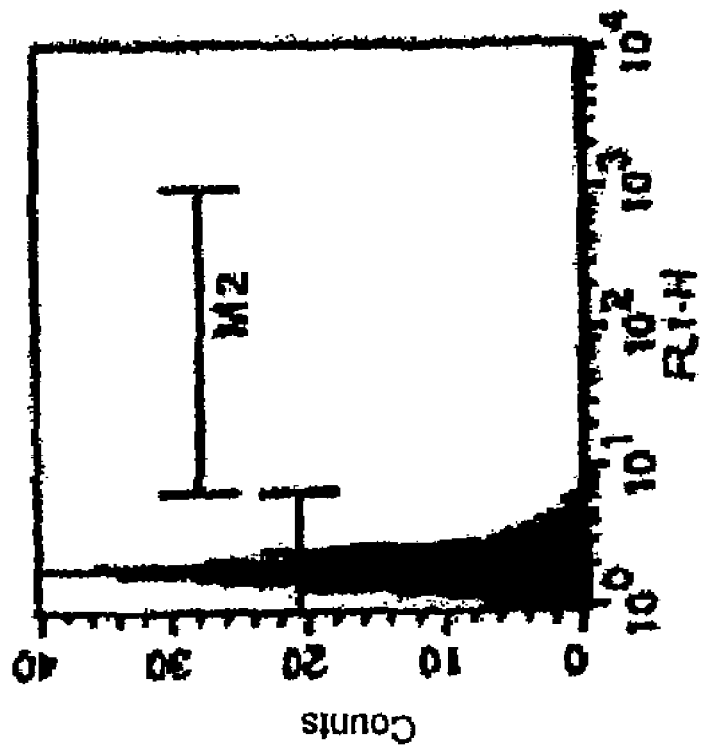

FIG. 16 (cont.)
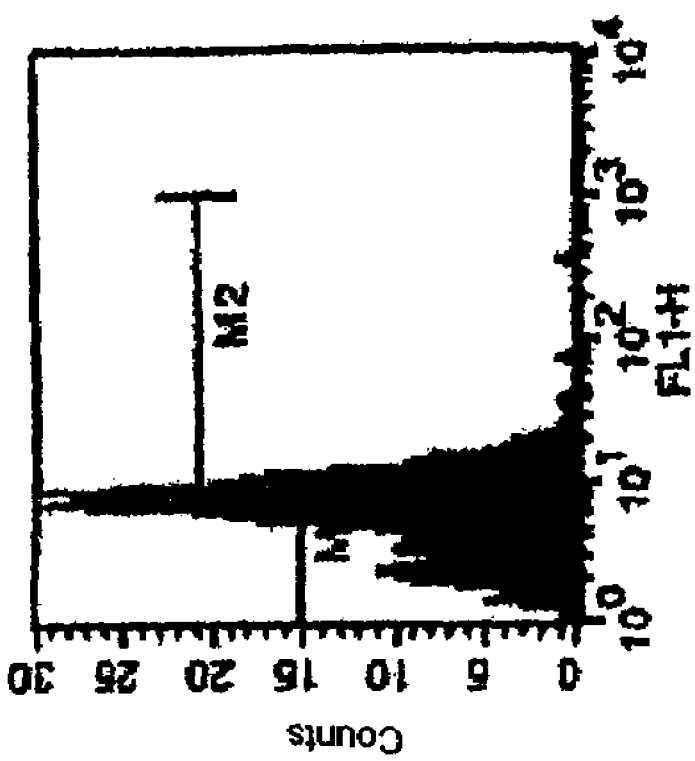
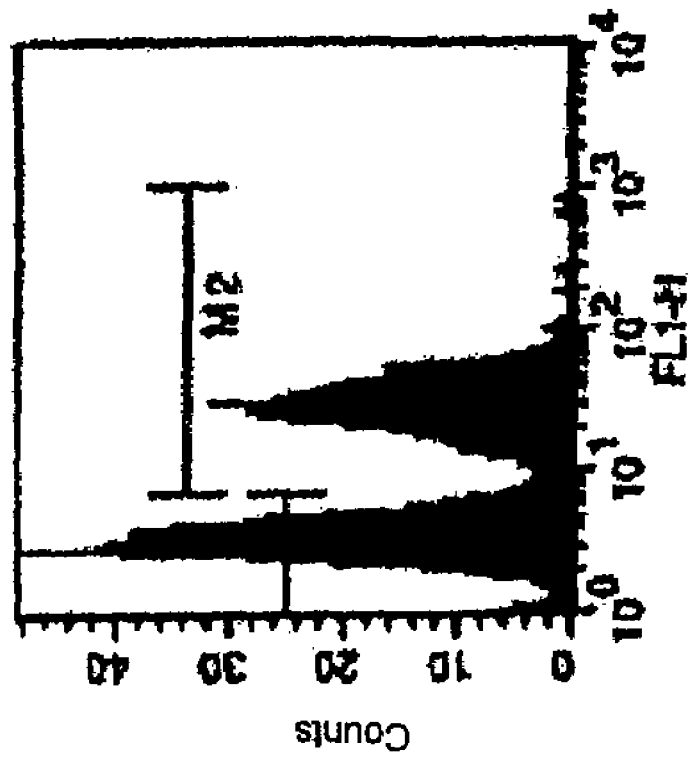

FIG. 17
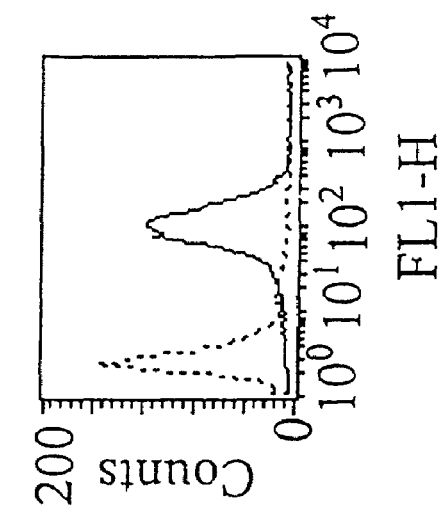
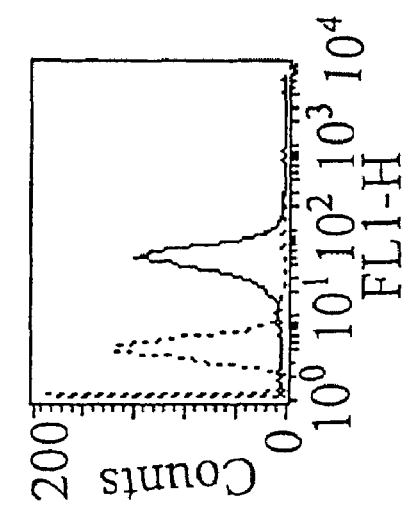
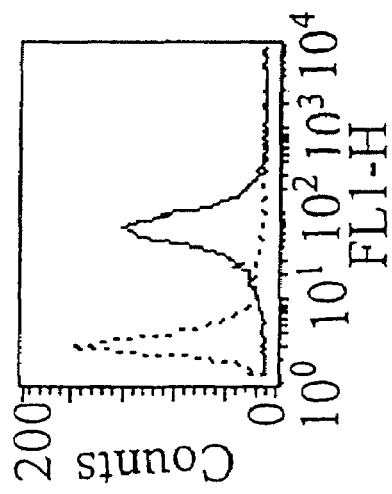

FIG. 17 (cont.)
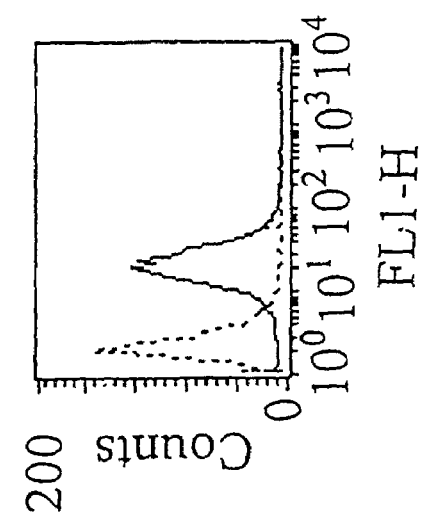
IV)
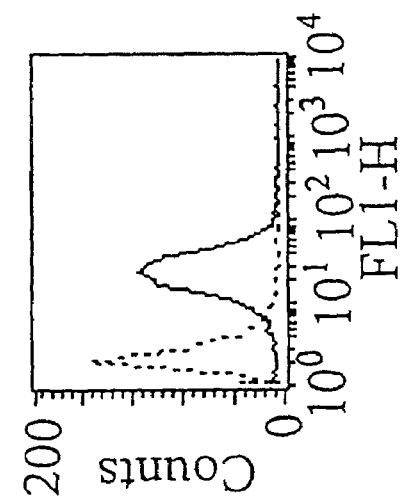
V)
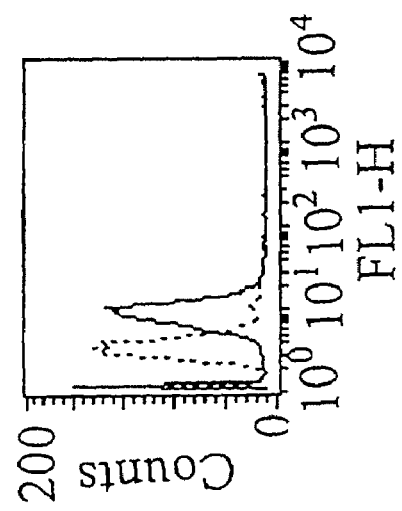
VI)

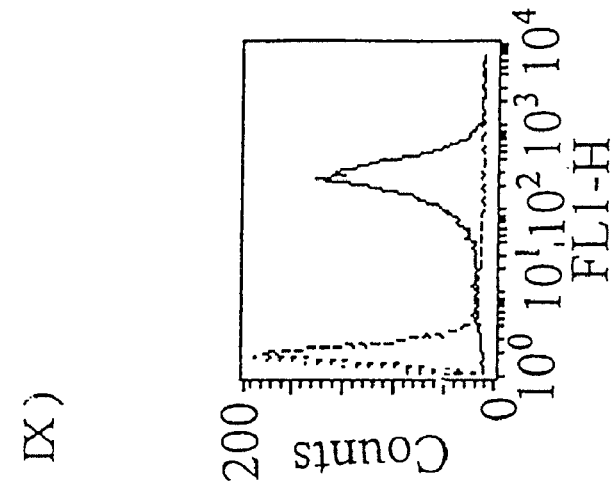
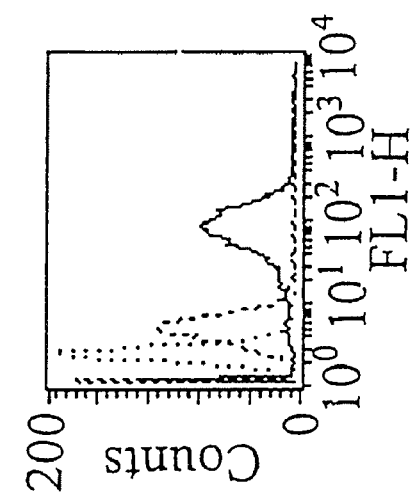
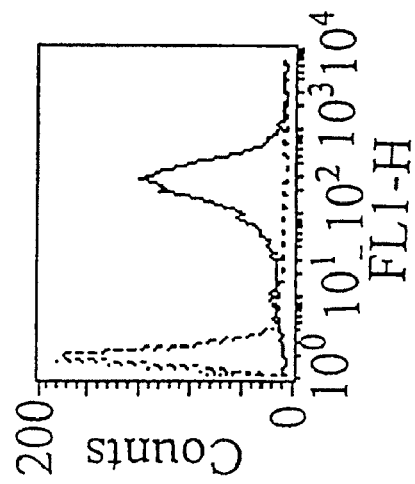
FIG. 17 (cont.)

FIG. 17 (cont.)
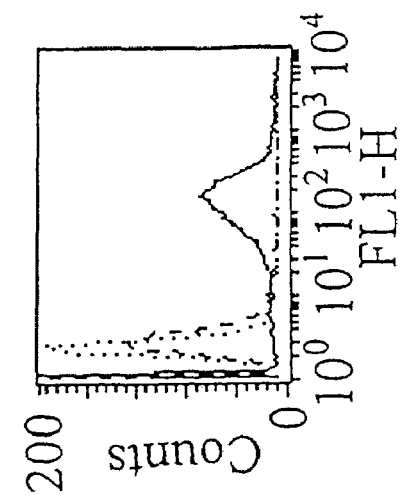
XII)
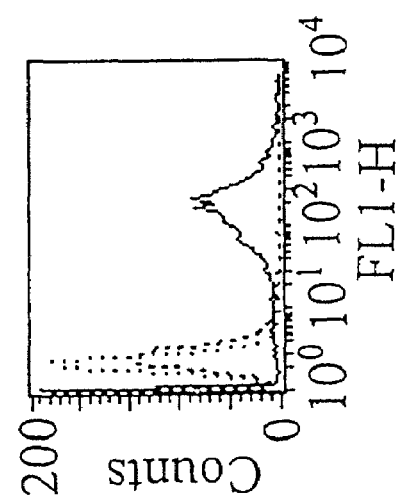
XI)
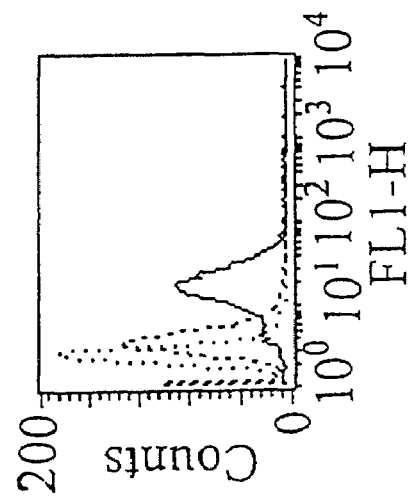
X)

Fig. 18: ADCC

M79:
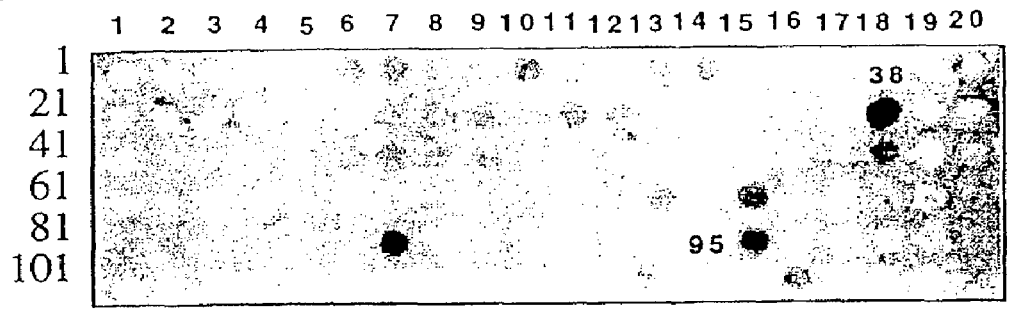
HRP-conjugated anti murine immunoglobulin secondary antibody:
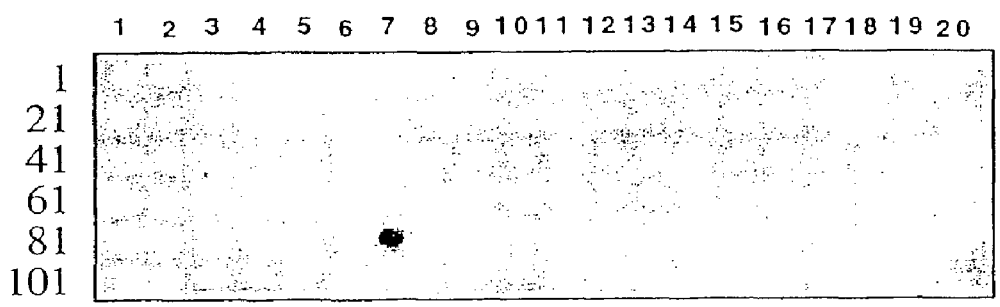
H79:
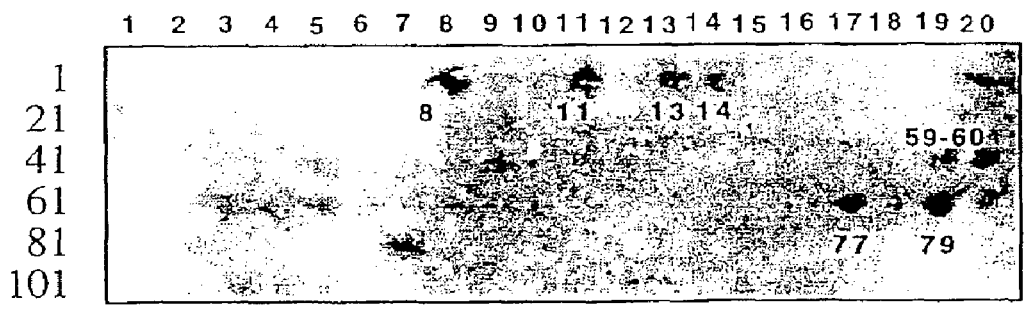
HD70:
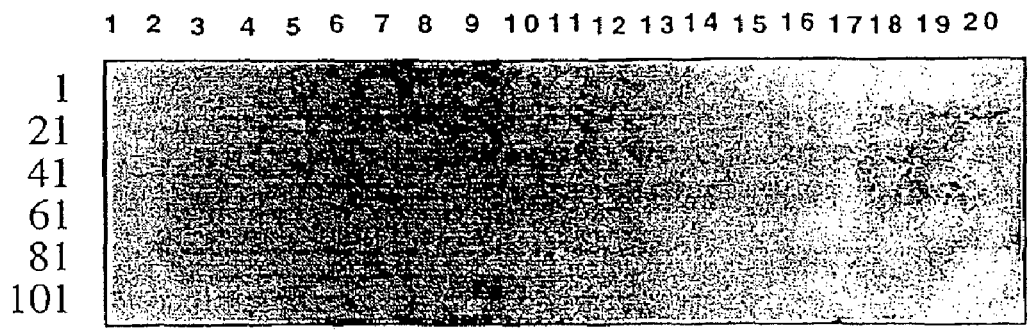
Fig. 27

ANTIBODIES THAT BIND HUMAN 17-A1/EPCAM TUMOR ANTIGEN

This application is a continuation of U.S. Ser. No. 10/325,694, filed Dec. 19, 2002, now abandoned, which is a divisional of U.S. Ser. No. 09/403,107, filed Oct. 14, 1999, now U.S. Pat. No. 7,227,002, which is a national stage application 37C.F.R. §371 of PCT/EP98/02180, filed on Apr. 14, 1998, which claims priority to EP 97106109.8, filed Apr. 14, 1997. The entire text of each of the above-referenced applications are specifically incorporated herein by reference without disclaimer.

The present invention relates to a method for the production of an anti-human antigen receptor that is low or not immunogenic in humans comprising the steps of selecting a combination of functionally rearranged VH and VL immunoglobulin chains wherein at least said VH chain is derived from essentially unprimed mature human B-lymphocytes or from essentially anergic human B cells and said VL chain is derived from a naturally occurring human B cell repertoire, said chains being expressed from a recombinant vector and using an in vitro display system for binding to a human antigen.

The present invention further relates to receptors that are low or not immunogenic in humans and directed to human antigens, said receptors being obtainable by the method of the invention. Said receptors are preferably antibodies or fragments thereof or immunoconjugates comprising the VH/VL chains of said antibody. In particular, the receptors of the invention are directed to human tumor antigens, preferably to the human tumor antigen 17-1A, also known as EpCAM, EGP-40 or GA 733-2. Finally, the present invention relates to kits useful for carrying out the method of the invention.

The mammalian immune systems such as the human immune system select against immune competent cells and molecules that are specific for self-antigens. Dysregulation of the immune system in this regard may result in auto-immune diseases such as rheumatoid arthritis. In general, the surveillance of the immune system with regard to the autoreactive antibodies or T cells is therefore highly beneficial. However, there may be cases where it would be advantageous to have autoreactive antibodies that are directed to antigens expressed in the mammalian, and in particular, the human body. Such antigens are, for example, tumor associated antigens. For example, the human 17-1A or EpCAM antigen, a surface glycoprotein expressed by cells of simple epithelia and malignant tumors derived thereof, has been shown to be a rewarding target for monoclonal antibody therapy of cancer, especially in patients with minimal residual disease suffering from disseminated tumor cells that may cause later solid metastasis and thus impairs patients' prognosis. In patients with minimal residual colorectal cancer, a murine monoclonal antibody specific for the human 17-1A-antigen decreased the 5-year mortality rate by 30% compared to untreated patients, when applied systemically in five doses within four months after surgery of the primary tumor; in total each patient was treated with 900 mg of antibody (Riethmüiller, Lancet 343 (1994), 1177-1183). However, during the course of antibody treatment patients developed a strong antibody response against the murine immunoglobulin. These human anti-mouse antibodies (HAMAs) severely limit the continuous application of antibody therapies and increasingly reduce their efficacy. Moreover, preformed HAMAs induced by former antibody treatment or another contact with murine immunoglobulin can severely interfere with later antibody therapies.

To prevent these problems, therapeutic antibodies with minimal immunogenicity would be preferable. To achieve this goal, it might be, for example, envisaged that therapeutic antibodies or antibody derivatives are completely human by their amino acid sequence and the immunogenic profile of the human antibody idiotype is minimized by using human Ig-variable regions likely to be tolerated by the human immune system.

However, the generation of human antibodies against human antigens faces two major problems:
(1) Hybridoma or other cell immortalisation techniques proved to be quite inefficient in generating human antibody producing cell lines compared to the murine hybridoma technology.
(2) Auto-reactive antibodies are relatively efficiently depleted of naturally occurring antibody repertoires due to the mechanisms mediating self-tolerance.

Human antibodies in general have become much more accessible since the availability of transgenic mice expressing human antibodies (Bruggemann, Immunol. Today 17 (1996), 391-397) and of the combinatorial antibody library and phage display technology allowing the in vitro combination of variable regions of Ig-heavy and light chains (VH and VL) and the in vitro selection of their antigen binding specificity (Winter, Annu. Rev. Immunol. 12 (1994), 433-455). By using the phage display method, rare events like one specific binding entity out of $10^7$ to $10^9$ different VL/VH- or VH/VL-pairs can easily be isolated; this is especially true when the repertoire of variable regions has been enriched for specific binding entities by using B-lymphocytes from immunized hosts as a source for repertoire cloning.

Often, however, the frequency of specific binding entities is substantially lowered in naturally occurring antibody repertoires. This is particularly true for cases of antibodies binding to self-antigens. Random combinations of VL- and VH-regions: from a self-tolerant host resulting in a combinatorial antibody library of conventional size ($10^7$ to $10^9$ independent clones) most often are not sufficient for the successful in vitro selection of auto-reactive antibodies by the phage display method.

One strategy to circumvent this problem is the use of very large combinatorial antibody libraries that compensate by the library size for the low frequency of auto-reactive antibodies in naturally occurring repertoires. Combinatorial antibody libraries exceeding a size of 109 independent clones, however, are difficult to obtain because of the current technical limit of the transformation efficiency for plasmid-DNA into *E. coli*-cells.

To avoid the self-tolerance mediated bias in naturally occurring antibody repertoires, that underrepresents auto-reactive antibodies and markedly decreases the chances of isolating antibodies specifically recognizing self-antigens, approaches using semisynthetic or fully synthetic VH- and/or VL-chain repertoires have been developed. For example, almost the complete repertoire of unrearranged human V-gene-segments has been cloned from genomic DNA and used for in vitro recombination of functional variable region genes, resembling V-J- or V-D-J-recombination in vivo (Hoogenboom, J. Mol. Biol. 227 (1992), 381-388; Nissim, EMBO J. 13 (1994) 692-698; Griffiths, EMBO J. 13 (1994), 3245-3260). Usually, the V-D-/D-J functional and the D-segment diversity mainly responsible for the extraordinary length and sequence variability of heavy chain CDR3 as well as the V-J functional diversity contributing to the sequence variability of light chain CDR3 is imitated by random sequences using degenerated oligonucleotides in fully synthetic and semisynthetic approaches (Hoogenboom (1994), supra; Nissim, supra; Griffiths, supra; Barbas, Proc. Natl. Acad. Sci. U.S.A. 89 (1992), 4457-4461). However, VL/VH- or VH/VL-pairs selected for binding to a human antigen from such semisynthetic or fully synthetic repertoires based on human V-gene sequences are at risk of forming immunogenic epitopes that may induce an undesired immune response in humans (Hoogenboom, TIBTECH 15 (1997), 62-70); especially the CDR3-regions derived from completely randomized sequence repertoires are predestined to form potentially immunogenic epitopes as they have never had to stand the human immune surveillance without being recognized as a foreign antigen resulting in subsequent elimination. This is equally true for human antibodies from transgenic mice expressing human antibodies as these immunoglobulin molecules have been selected for being tolerated by the murine but not the human immune system.

Accordingly, the technical problem underlying the present invention was to provide a method that allows the production of receptors that are low or not immunogenic in humans and that can be used for targeting antigens in the human body. The solution to said technical problem is achieved by providing the embodiments characterized in the claims.

Thus, the present invention relates to a method for the production of an anti-human antigen receptor that is low or not immunogenic in humans comprising the steps of selecting a combination of functionally rearranged VH and VL immunoglobulin chains wherein at least said VH chain is derived from essentially unprimed mature human B-lymphocytes or from essentially anergic human B cells and said VL chain is derived from a naturally occurring B cell repertoire, said chains being expressed from a recombinant vector and using an in vitro display system for binding to a human antigen.

The method of the present invention is highly advantageous for providing receptors that can be used for targeting antigens in humans without being at all or to any significant extent immunogenic themselves. Such receptors can advantageously be used for treating a variety of diseases such as tumors or auto-immune diseases, graft rejection after transplantation, infectious diseases by targeting cellular receptors as well as allergic, inflammatory, endocrine and degenerative diseases by targeting key molecules involved in the pathological process.

The VH/VL immunoglobulin chains of the receptors of the present invention can, of course, be further investigated with regard to their nucleic acid and amino acid sequences using techniques well-known in the art, see e.g. Sambrook (Molecular Cloning; A Laboratory Manual, 2nd Edition, Cold Spring Harbour Laboratory Press, Cold Spring Harbor, N.Y. (1989)). Once the nucleic acid sequence or the amino acid sequence have been determined, the receptors of the invention can also be produced by other methods, such as by synthetic or semi-synthetic methods yielding synthetic or semi-synthetic receptors, or in transgenic mice expressing human immunoglobulin receptors; carrying the features recited herein above and produced by such synthetic or semi-synthetic methods or in said transgenic mice are also included within the scope of the present invention.

After binding of the receptor to the human antigen, the receptor can be further purified. For example, non-bound receptors which do not carry the antigen specificity may be removed by washing steps. The bound receptor may be eluted from the human antigen and further purified, wherein additional rounds of expression, binding and selection of the desired receptor may be used until the desired receptor and/or the corresponding recombinant vector have been isolated in pure form.

The method of the present invention thus makes use of the preselection of Ig-variable regions by the human immune system. The receptors are derived from a repertoire selected in vitro from human combinatorial antibody libraries exclusively or preferentially made of the naturally occurring antibody repertoire expressed by essentially unprimed mature human B-lymphocytes or from essentially anergic human B-cells.

However, the Ig variable domains may also be derived from a variety of other sources that represent these preselected populations of B cells.

The scientific background with regard to the origin of the B cells functioning as a source of said VH or VL chains, may be explained as follows:

Mature unprimed B-lymphocytes, expressing IgD and IgM as membrane antigen receptors enter primary follicles during their traffic to and between secondary lymphoid organs unless they have encountered multivalent self antigen resulting in clonal deletion or soluble monovalent self antigen rendering them anergic and short-lived due to exclusion from primary follicles.

Contact of immature B-cells, that exclusively express IgM, with self antigen in the bone marrow results in clonal deletion or anergy depending on the antigen valency. Anergic B-cells, although expressing surface IgD, are unable to respond to the antigen through this receptor; without access to primary follicles and in the absence of T-cell help, these cells have a short half-life of only a few days.

In contrast, mature unprimed B-lymphocytes that have not encountered self antigen and therefore have access to primary follicles have a long half-life of several weeks. Despite the described mechanisms mediating self-tolerance, these populations of long-lived mature unprimed B-lymphocytes still contain potentially self-reactive B-cells, that are, however, unlikely to find specific T-cell help due to T-cell tolerance and thus kept from proliferation and antibody secretion. It appears that B-cell non-responsiveness to many self-antigens that are present at low levels is of this type, affecting the helper T-cells but not the B-cells. In the present invention these long-lived, non-responsive, potentially self-reactive mature unprimed B-lymphocytes have been identified as the most promising naturally occurring human antibody repertoire for constructing combinatorial antibody libraries especially suited to select human antibodies to human antigens by, for example, the phage display method.

This highly selected antibody repertoire used as a basis for the present invention mainly derived from B-cells with a long in vivo half-life and thus exposed to the human immune system for prolonged periods of time is expected to be markedly depleted of antibody molecules forming epitopes especially within the highly variable CDR3-regions, that are immunogenic for the human immune system. Therefore, human antibodies selected from this antibody repertoire are expected to have a lower immunogenic profile in humans than human antibodies selected from semisynthetic or fully synthetic human antibody libraries.

Mature unprimed B-cells that are activated by contact with foreign antigen stop to express IgD and start clonal proliferation and differentiation into plasma cells secreting soluble immunoglobulin; early stages of the antibody response are dominated by IgM-antibodies, while later, IgG and IgA are the predominant isotypes, with IgE contributing a small but biologically important part of the antibody response.

Unlike IgD-negative mature antigen-primed B-lymphocytes expressing IgM, IgG, IgA or IgE, IgD-positive mature unprimed B-cells have not yet undergone clonal proliferation, so that combinatorial IgD-libraries do not overrepresent antibody specificities that are currently or have been formerly involved in immune responses usually driven by foreign antigen, thus decreasing repertoire diversity and wasting library space for antibody candidates unlikely to bind self antigen. This is in clear contrast to the prior art recommending the use of human IgM combinatorial antibody libraries for the in vitro selection of human antibodies against human antigens from naturally occurring human antibody repertoires (Hoogenboom (1997), supra).

In a preferred embodiment of the method of the invention, said antigen receptor is an immunoglobulin or a fragment thereof.

The fragment of the immunoglobulin may be any fragment that is conventionally known in the art such as Fab or F(ab)2 fragments.

In a particularly preferred embodiment of the method of the invention, said immunoglobulin fragment is an Fv-fragment.

In a further preferred embodiment of the method of the invention, at least said VH and optionally said VL immunoglobulin chain are derived from a human IgD repertoire.

This receptor and preferably antibody repertoire selected for low immunogenicity has been concluded to be best represented in a human IgD-antibody library. IgD is expressed as membrane antigen receptor together with surface IgM on mature unprimed B-lymphocytes that enter primary follicles during their traffic to and between secondary lymphoid organs unless they have encountered multivalent self antigen resulting in clonal deletion or soluble monovalent self antigen rendering them anergic and short lived due to exclusion form primary follicles. In addition to the antibody repertoire of mature unprimed B-lymphocytes, human IgD-libraries only further represent that of short-lived B-cells that have been rendered anergic in contact with soluble monovalent self antigen but are unlikely to contribute specific binders to human cell surface molecules resembling multivalent self-antigens that induce clonal deletion instead of B-cell anergy.

In a further preferred embodiment of the method of the invention, said in vitro display system is a phage display system.

The phage display system has, in the past, conveniently been used for the selection of a variety of peptides and proteins that bind to specific targets. On the basis of this knowledge, the immunoglobulin VH and VL chains can conveniently be cloned into vectors that also comprise molecules useful for phage display systems. Such molecules and vectors, respectively, are well-known in the art (Winter, supra; Barbas, METHODS: A Companion to Methods in Enzymology 2 (1991), 119-124) and need not be explained here in more detail.

In a further preferred embodiment of the method of the invention, said combination of rearranged chains is expressed from one or more different libraries.

This embodiment is particularly preferred, if a VH or VL chain is known that binds to a specific target and the corresponding second V chain that reconstitutes or improves binding is selected.

In a further preferred embodiment of the method of the invention, said human antigen is a tumor antigen.

If the human antigen is a tumor antigen, said antigen is preferably expressed on the surface of said tumor. In this case, the VH and VL chains are advantageously coupled to a toxine. The coupling can be effected on the nucleic acid level by genetic engineering or at the protein level by, for example, chemical coupling.

It is particularly preferred that said tumor antigen is the 17-1A antigen. In a further particularly preferred embodiment of the method of the invention, said VH chain comprises one of the two sequences shown in FIG. 7 (nucleotides 1 to 381) and FIG. 8 (nucleotides 1 to 339) and/or said VL chain comprises one of the two following sequences shown in FIG. 6 (nucleotides 1 to 321) and FIG. 9 (nucleotides 1 to 321). Receptors with these specific VH and VL regions, wherein said VL region can be combined with both VH regions, are the first human antibodies that are specific for the human 17-1A antigen.

In a further preferred embodiment of the method of the invention, said selection step involves
    (i) binding of the display vehicle expressing an antigen receptor
        (a) on immobilized target antigen or fragments thereof;
        (b) on optionally labeled cells expressing the target antigen or fragments thereof; or
        (c) to soluble, preferably labeled target antigen or fragments thereof,
    (ii) washing off non-specifically binding display vehicle (a and b) and subsequent elution of specifically binding display vehicle by non-specific (e.g. low pH buffer) or specific means (e.g. target antigen specific antibody) or
    (iii) positive enrichment of target antigen bound display vehicle (b and c) from target antigen solution or from suspensions of cells expressing the target antigen for example using magnetic beads binding to labeled target antigen or labeled cells expressing the target antigen respectively; thus isolated display vehicles including their antigen receptors optionally being multiplied by replication and subjected to further rounds of in vitro selection as described.

In a further preferred embodiment of the method of the invention, prior to said selection step either said VH or said VL chain is selected for binding to said antigen together with a surrogate V chain.

This two-step procedure can be employed using a target antigen specific template antibody from a different species, for example a murine monoclonal antibody against the human target antigen. First, a human VL- or VH-repertoire is combined with a single surrogate VH- or VL-chain from the murine template antibody, displayed, e.g., on filamentous phage and selected in vitro for antigen binding. Thus, the complete library size is available exclusively for the human VL- or VH-repertoire and candidate human VL- or VH-chains can be isolated that are capable of contributing to specific binding of the human target antigen. In a second step, the surrogate variable region of the template antibody is replaced by the corresponding human variable region repertoire followed by a second round of in vitro selection; again, the complete library size is exclusively available for a single VH- or VL-region repertoire, thus enabling much more VL- and VH-region candidates to be screened for antigen binding under conditions of limited library size by the two-step procedure than by a single-step procedure.

For cloning of DNA-sequences encoding the variable regions of human antibodies that specifically bind to the human 17-1A-antigen, this two-step selection procedure for screening human IgD-combinatorial antibody libraries by the phage display method was advantageously employed. First, the Fd-heavy chain segment (VH+CH1) of the murine monoclonal antibody M79 (Gottlinger, Int. J. Cancer 38 (1986), 47-53) that specifically binds to the human 17-1A-antigen was combined with a human kappa- and lambda-light chain repertoire respectively. The resulting libraries were displayed on filamentous phage and selected in vitro by several rounds of panning on immobilized recombinant human 17-1A-antigen. Soluble Fab-fragments were expressed from several clones after each round of panning and screened by ELISA for antigen binding. Each of the strong binding entities enriched during the panning procedure proved to contain the same human kappa-light chain as confirmed by sequence analysis. This human light chain further on called K8 was then combined with a human IgD-heavy chain library, that was again displayed on filamentous phage and selected in vitro by several rounds of panning on immobilized recombinant human 17-1A-antigen. Several Fab-fragments were expressed from several clones after each round of panning and again screened by ELISA for antigen binding. Sequence analysis of the binding entities enriched during the panning procedure revealed two different heavy chain-variable regions called D4.5 and D7.2 each of which combines with the K8-light chain to form different human antigen binding sites with specificity for the human 17-1A-antigen. The human light and heavy chain repertoires were cloned from several preparations of total RNA isolated from human blood and bone marrow samples of several donors by using kappa or lambda light chain specific as well as IgD-heavy chain specific RT-PCR. As it is impossible to selectively amplify the light chain repertoire that is combined with IgD-heavy chains in vivo, unless IgD-positive B-cells are purified for RNA-preparation, the light chain libraries used are not limited to the antibody repertoire of mature unprimed or anergic B-lymphocytes. However, due to the predominance of the heavy chain in antigen recognition, this does not substantially undermine the advantages of the IgD-repertoire for selecting human antibodies to self-antigens. Further and most importantly due to the exposure to the human immune system selection of such light chains still guarantees a low immunogenic profile in humans.

In a further particularly preferred embodiment of the method of the invention, said surrogate chain is a mouse VH or VL chain.

In a further preferred embodiment of the method of the invention, said selection of a suitable combination involves (a) testing one and the same VH chain in combination with a variety of different VL chains for binding to said human antigen; or (b) testing one and the same VL chain in combination with a variety of different VH chains for binding to said human antigen.

This embodiment is advantageously employed again, if either the VL or the VH chains are known to specifically interact with the human target molecule. Then, an appropriate second chain can be selected on the basis of preferably an improved binding to the target molecule.

In a further preferred embodiment of the method of the invention, said method comprises the steps of obtaining, after selection, the human VH and VL chains or the corresponding nucleic acids and fusing said chains to the same or other VH or VL chains, to immunoglobulin constant regions of heavy (CH) or light chains (CL) or parts thereof or to other biologically active molecules such as peptides, proteins, nucleic acids, small organic compounds, hormones, neural transmitters, peptidomimics, PNAs (Milner, Nature Medicine 1 (1995), 879-880; Hupp, Cell 83 (1995), 237-245; Gibbs and Oliff, Cell 79 (1994), 193-198). The other functional molecule may be either physically linked by, e.g., chemical means to VH and VL chains or may be fused by recombinant DNA techniques well known in the art. This embodiment of the invention is particularly useful for developing specific drugs that may be used to target desired antigens in the human body. For example, if tumor antigens are targeted, the VH and VL chains may, at the nucleic acid or amino acid level, be fused to a toxin moiety, thus resulting in an immunotoxin, to the extracellular portion of a cellular receptor or a soluble cytokine or parts thereof respectively, thus resulting in constructs enhancing the anti-tumor immune response or to an antibody-Fv-fragment thus resulting in a bispecific antibody derivative.

In a further particularly preferred embodiment of the method of the invention, said constant region chains are derived from human IgG1 or IgG3.

The constant region chains of human IgG1 or IgG3 are preferentially used if cells expressing the target antigen should be destroyed in the human body. It is well-known in the art that these IgG-subclasses efficiently mediate antibody dependent cellular cytotoxicity (ADCC) and contribute to the destruction of cells recognized and bound by these antibody subclasses.

In a further preferred embodiment of the method of the invention, said VH and/or VL chains are coupled with non-proteinous pharmaceuticals preferably of low molecular weight such as radioisotopes or substances used for chemotherapy, thus resulting in a more specific in vivo targeting of said pharmaceuticals.

In a further preferred embodiment of the method of the invention, said VH or VL chains are expressed from nucleic acid sequences that are the result of the RT-PCR amplification of mRNA derived from essentially unprimed mature human 13-lymphocytes or essentially anergic human B-cells.

It is preferred to amplify the VH or VL chains by RT-PCR once the suitable source thereof has been identified and isolated. It is preferred to use the mRNA of nucleated cells from human bone marrow or more preferable from human blood for amplifying VH or VL chains by RT-PCR as these two tissue compartments are the most easily accessible B-cell sources in humans. It is further preferred to isolate anergic B-cells or more preferable mature unprimed B-lymphocytes from the nucleated cells of said tissue compartments by using e.g. magnetic beads or flow cytometry based cell sorting prior to RNA-preparation. This procedure guarantees that both, VH and VL chains amplified by RT-PCR, are derived from the preferred B-cell population. Alternatively, if mRNA of the whole fraction of nucleated cells from said tissue compartments is used to amplify VH or VL chains by RT-PCR, it is preferable to amplify the VH-region as half of the heavy chain Fd-segment (VH-CHI) of human IgD by using an IgD-specific 3' PCR-primer e.g. that enlisted in table 1 which exclusively gives raise to PCR-products from the human IgD-heavy chain, only expressed in mature unprimed human B-lymphocytes and in anergic human B-cells.

In a further preferred embodiment of the method of the invention, the anti-human antigen receptor which is low or not immunogenic in humans, comprises a combination of functionally rearranged VH and VL chains preferably from essentially unprimed mature human B-lymphocytes or essentially anergic human 13-cells and obtainable by the method according to the invention described above. The advantages of the antibody of the invention have been outlined herein above. It has to be emphasized that corresponding antibodies directed against human antigens and derived from human sources, said antibodies having thus a low or no immunogenicity in humans, have so far not been isolated in the art. Accordingly, the antibodies of the invention are the starting point of a whole new development of antibodies that may be used in various fields of medicine and pharmacy.

In an additional preferred embodiment of the method of the invention, the receptor is an antibody or a fragment thereof.

In another preferred embodiment of the method of the invention, the receptor is specific for a human tumor antigen, most preferably for the human 17-1A antigen.

The invention furthermore relates to a receptor wherein said VH chain comprises one of the sequences shown in FIG.

7 (nucleotides 1 to 381) and FIG. 8 (nucleotides 1 to 339) and/or said VL chain comprises one of the two following sequences shown in FIG. 6 (nucleotides 1 to 321) and FIG. 9 (nucleotides 1 to 321).

Furthermore, the invention relates to a VH chain or a part thereof comprised in the receptor of the invention.

The invention also relates to a VL chain or a part thereof comprised in the receptor of the invention.

In a further particularly preferred embodiment of the method of the invention, said part of said VH chain is the CDR3 domain.

Furthermore, the invention relates to a kit comprising a combination of functionally rearranged VH and VL immunoglobulin chains wherein at least one of the VH and VL chains are derived from essentially unprimed mature human B lymphocytes or from essentially anergic human B cells, said chains being expressible from recombinant vectors of an in vitro display system.

Said kit is advantageously used in carrying out the method of the invention and thus obtaining receptors of desired specificity.

Preferably, in said kit, said in vitro display system is a phage display system.

The invention relates further to an antibody characterized in that it is derived from human sequences and is specific for the human 17-1A antigen.

With the method of the invention, for the first time a human antibody which is specific for the human 17-1A antigen has been developed. As has been pointed out before, this development was no trivial task, since human antibodies against human tumor associated antigens are usually subjected to mechanisms mediating self tolerance of the immune system, thus resulting in the elimination of B-lymphocytes expressing autoreactive antibodies in vivo. Among the known tumor associated antigens 17-1A is by far more ubiquitously expressed on a broad range of normal epithelial tissues than other tumor antigens, in addition to its expression on epithelial tumors. Therefore, the 17-1A-antigen is currently regarded to represent a pan-epithelial antigen rather than a tumor antigen, which it was thought to be at the time of its first description. In comparison, other so called tumor antigens found on epithelial tumors, like erb-B2 (Her 2/neu), Muc-1 (PEM) or the Thompson-Friedreich-antigen usually show a much more restricted expression pattern on normal epithelial tissues. Thus, the selective force of self tolerance against 13-lymphocytes expressing 17-1A reactive antibodies even with low affinity is expected to be exceptionally high, since it appears nearly impossible for such 13-cells to avoid encounters with the 17-1A antigen for longer periods of time, due to the ubiquity of this antigen. Therefore, it was surprisingly found in accordance with the present invention, that 17-1A specific antibodies or at least the corresponding heavy chains can be isolated from the antibody repertoire of human B-cells such as e.g. mature unprimed B-lymphocytes. These B-cells are known to have a long in vivo half life and have already managed to avoid depletion prior to their maturation despite the presence of the 17-1A antigen even at the site of maturation; B-cell anergy does not occur in case of the 17-1A antigen as this type of B-cell tolerance is only induced by soluble self antigen. Only long-lived B-cells that managed to survive in spite of their potential 17-1A reactivity represent a repertoire of human immunoglobulin variable regions, that is likely to be well tolerated by the human immune system when used for the construction of human antibodies and antibody derivatives designed to be repeatedly administered systemically to human beings since it has already been screened for and subsequently eliminated from immunogenic sequences by the surveillance function of the immune system.

Therefore, the present invention also relates to human antibodies specific for the 17-1A antigen and suited for repeated in vivo application regardless of the method by which they are obtained as human antibody sequences with said high in vivo compatibility are highly expected to be also found in the B-cell repertoire of healthy human beings, for example, by the method of the invention. Accordingly, for the first time now a human antibody has been developed that can advantageously be used in the monitoring and/or destruction of tumor cells carrying the 17-1A antigen. Thus, the antibody of the invention is advantageously low or non-immunogenic in humans. In a preferred embodiment, said antibody which is obtainable according to a method as described hereinabove. In another preferred embodiment, the antibody of the invention recognizes an epitope of the extracellulary domain of the 17-1A antigen preferably comprising at least one amino acid sequence of peptide Nos. 8, 11, 13, 14, 59, 60, 77 and 79. Preferably, the VH chain of the antibody of the invention comprises at least one CDR of one of the following two sequences shown in FIG. 7 (nucleotides 1 to 381) and FIG. 8 (nucleotides 1 to 339) and/or the VL chain comprises at least one CDR of the following two sequences shown in FIG. 6 (nucleotides 1 to 321) and FIG. 9 (nucleotides 1 to 321). Particularly preferred is an antibody, wherein said VH chain comprises one of the two following sequences shown in FIG. 7 (nucleotides 1 to 381) and FIG. 8 (nucleotides 1 to 339) and/or said VL chain comprises one of the following two sequences shown in FIG. 6 (nucleotides 1 to 321) and FIG. 9 (nucleotides 1 to 321).

This receptor and preferably antibody repertoire selected for low immunogenicity has been concluded to be best represented in a human IgD-antibody library. IgD is expressed as membrane antigen receptor together with surface IgM on mature unprimed B-lymphocytes that enter primary follicles during their traffic to and between secondary lymphoid organs unless they have encountered multivalent self antigen resulting in clonal deletion or soluble monovalent self antigen rendering them anergic and short lived due to exclusion form primary follicles. Except mature unprimed B-lymphocytes human IgD-libraries only represent the antibody repertoire of short-lived B-cells that have been rendered anergic in contact with soluble monovalent self antigen but are unlikely to contribute specific binding entities to human cell surface molecules resembling multivalent self-antigens that induce clonal deletion instead of B-cell anergy.

Moreover, the present invention relates to a pharmaceutical composition comprising at least one of the aforementioned receptors or parts thereof of the invention, either alone or in combination, and optionally a pharmaceutically acceptable carrier or excipient. Examples of suitable pharmaceutical carriers are well known in the art and include phosphate buffered saline solutions, water, emulsions, such as oil/water emulsions, various types of wetting agents, sterile solutions etc. Compositions comprising such carriers can be formulated by well known conventional methods. These pharmaceutical compositions can be administered to the subject at a suitable dose. Administration of the suitable compositions may be effected by different ways, e.g. by intravenous, intraperitoneal, subcutaneous, intramuscular, topical or intradermal administration.

Thus, the invention also relates to the use of a receptor or parts thereof produced according to the method of the invention for the preparation of a pharmaceutical composition for treating, preventing and/or delaying of a tumor, in a subject, preferably wherein the tumor is of epithelial origin.

The figures show:

FIG. 1. Cloning site of pComb3H with important restriction sites. The following abbreviations were used: P, promotor; VL, variable light chain domain; CL, constant light chain domain; VH, variable heavy chain domain; CHI, constant heavy chain domain 1; L1/2, procaryotic leader sequences. The domain designated as gene III in pComb3H encodes for the noninfectious part of the gene III-product of filamentous phages as e.g. VCSM13.

Figure 2:
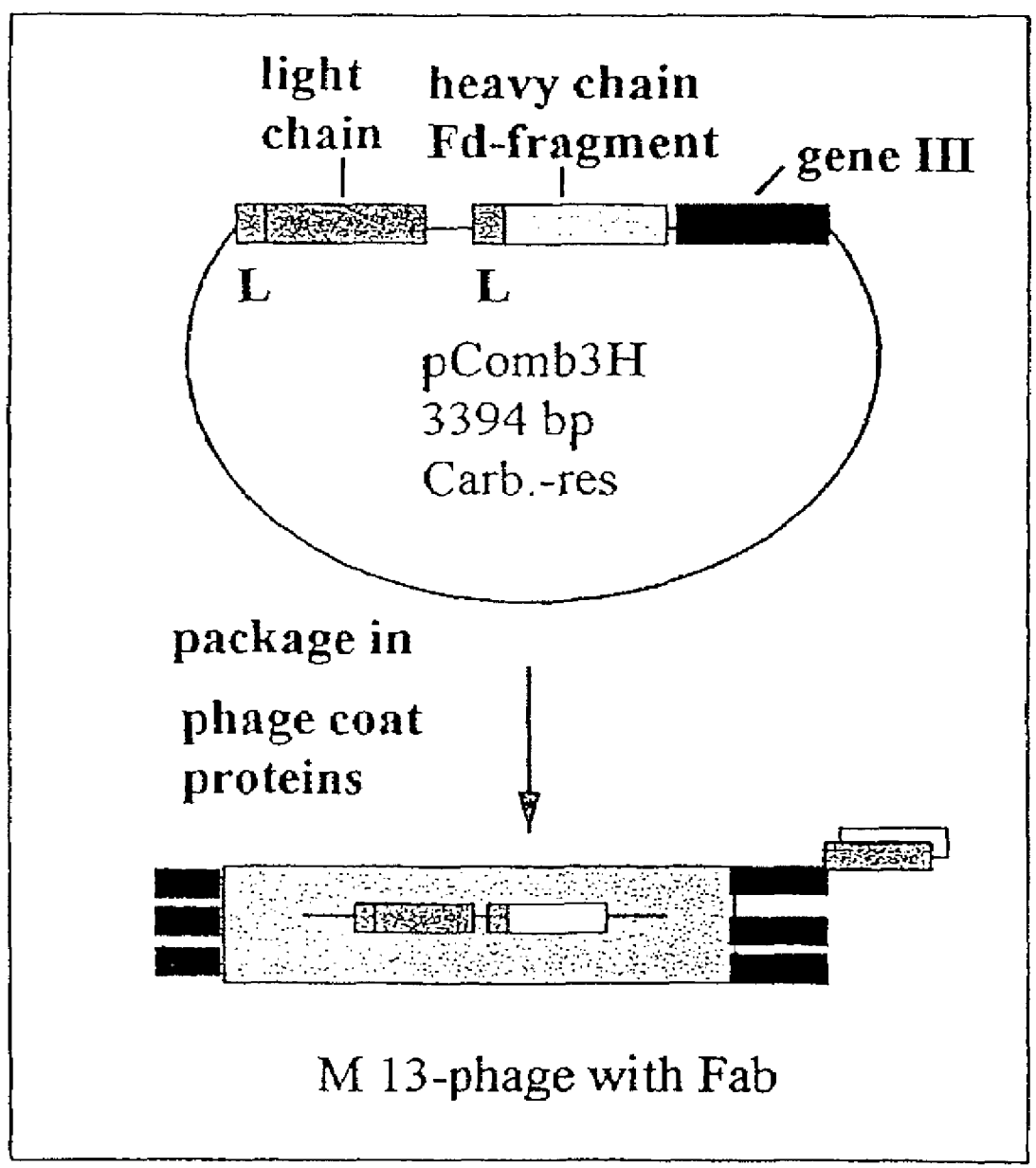

FIG. 2. Scheme of the pComb3H-plasmid and the fully expressed M 13-phage. On pComb3H the organization of leader (L) ompA, light chain, leader (L) pelB, heavy chain and gene III is shown. The fully expressed M13-phage displays on its surface the phenotype of a certain Fab antibody-fragment consisting of a light chain and the Fd-segment (VH+CHI) of a heavy chain linked to the non-infectious part of the gene III product and contains the corresponding genotype as single-stranded DNA encoding the heavy and light chain of the displayed Fab-fragment. The infectious gene 111-protein is provided by the helper phage VCSM13.

Figure 3:
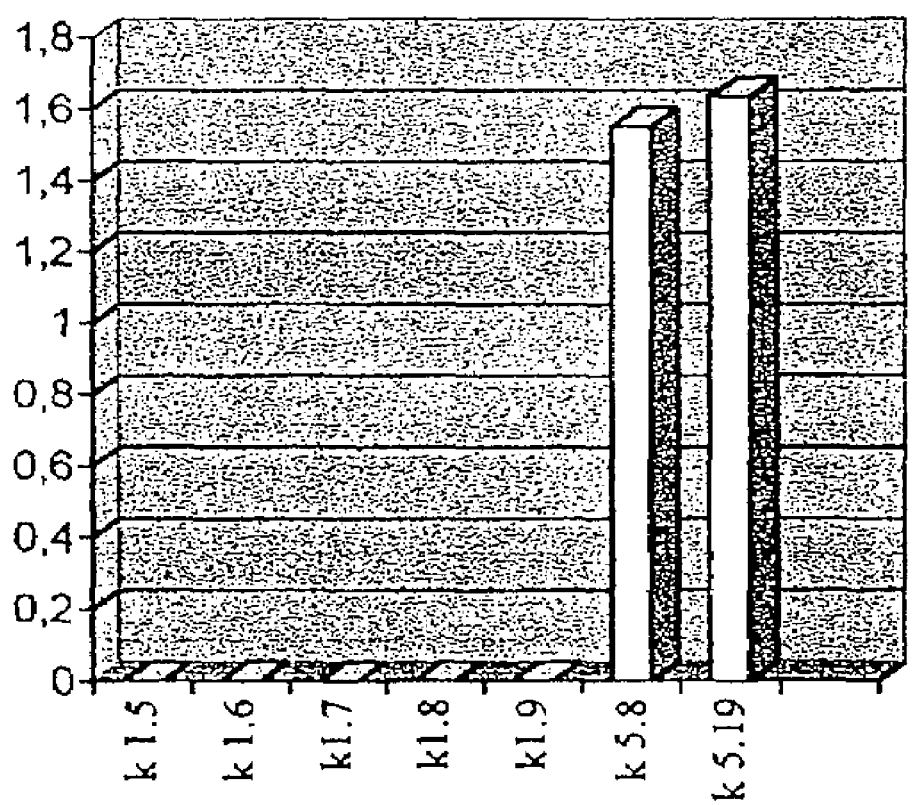

FIG. 3. ELISA of soluble Fab fragments. Periplasma preparations of soluble Fab fragments each containing the I'd segment of chimerized M79 and a single human kappa chain per clone. ELISA plates were incubated overnight with soluble 17-1A-antigen. Detection of bound Fab-antibody fragments was carried out with a peroxidase-conjugated polyclonal anti-human immunoglobulin antibody. The ELISA was finally developed by adding an ABTS-substrate solution (ABTS=2,2 Azino-bis(3-Ethylbenzthiazoline-6-Sulfonic Acid)) and the substrate turnover measured at a wavelength of 405 nm (y-axis). Clones are presented on the x-axis, the first number indicates the round of panning, the second one is the clone number. Clones 1.5-9 have a combination of chimeric M79 I'd segment with one random kappa chain and represent negative controls.

Figure 4:
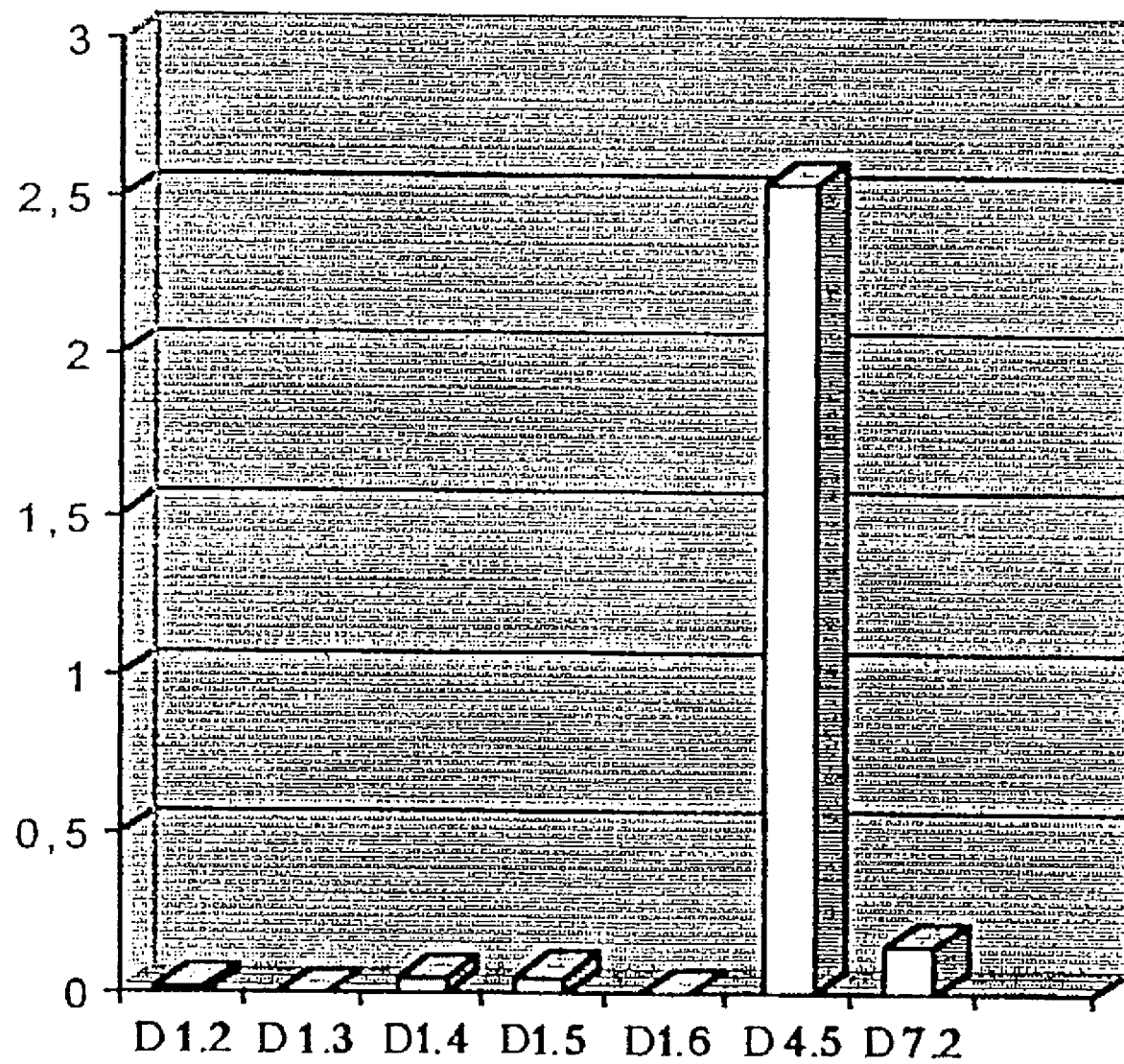

FIG. 4. ELISA of soluble Fab fragments. Periplasma preparations of soluble Fab fragments each containing the k8 light chain and a single human Ig delta chain Fd-segment. ELISA plates were incubated overnight with soluble 17-1A-antigen. Detection of bound Fab-antibody fragments was carried out with a biotinylated polyclonal anti-human kappa light chain antibody followed by peroxidase-conjugated streptavidine. The ELISA was finally developed by adding an ABTS-substrate solution (ABTS=2,2 Azino-bis(3-Ethylbenzthiazoline-6-Sulfonic Acid)) and the substrate turnover measured at a wavelength of 405 nm (y-axis). Clones are presented on the x-axis, the first number indicates the round of panning, the second one is the clone number. Clones 1.2-6 have a combination of k8 light chain with one random Ig delta heavy chain I'd-segment and represent negative controls.

Figure 5:
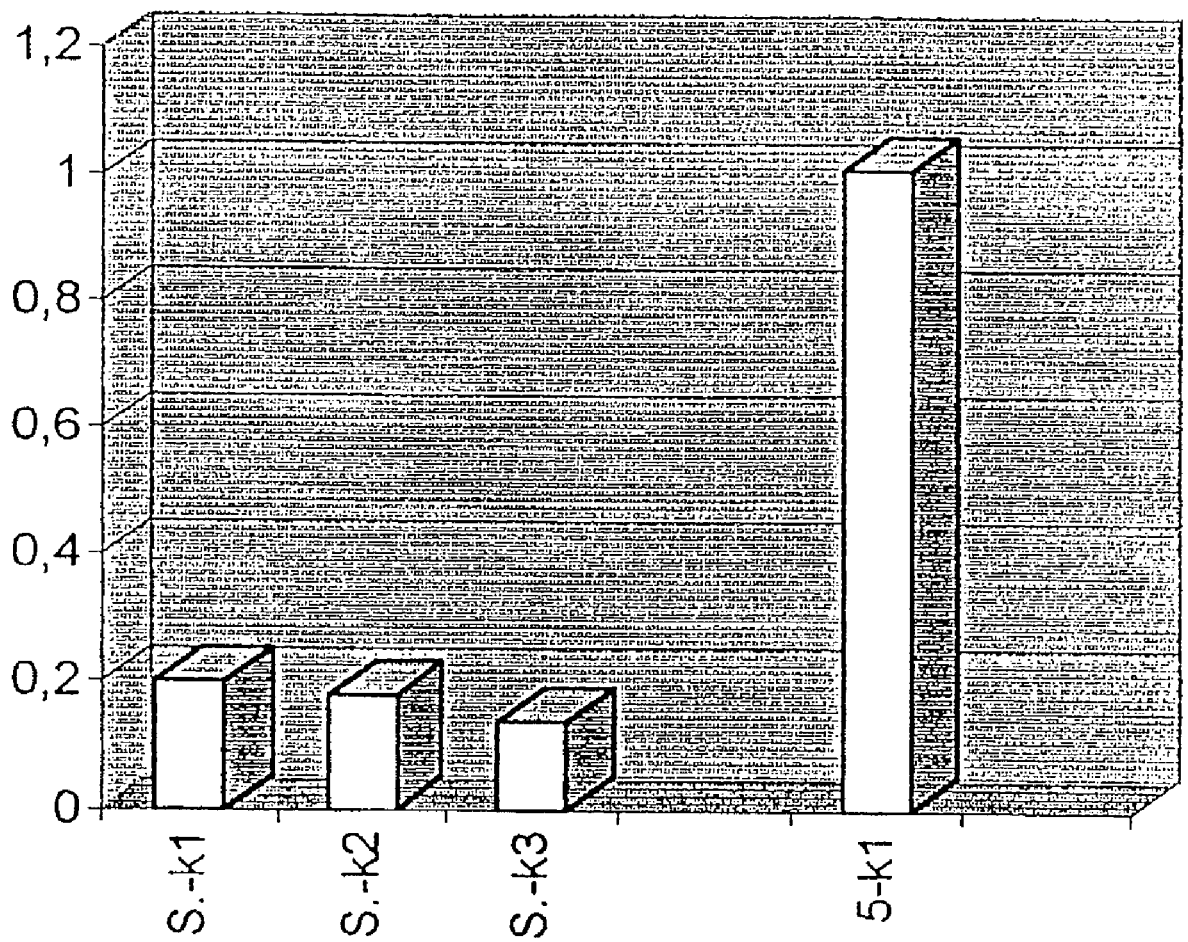

FIG. 5. ELISA of soluble Fab fragments. Periplasma preparations of soluble Fab fragments each containing the D4.5 Fd segment and a single human kappa chain per clone. ELISA plates were incubated overnight with soluble 17-1A-antigen. Detection of bound Fab-antibody fragments was carried out with a biotinylated polyclonal anti-human kappa light chain antibody followed by peroxidase-conjugated streptavidine. The ELISA was finally developed by adding an ABTS-substrate solution (ABTS=2,2 Azino-bis(3-Ethylbenzthiazoline-6-Sulfonic Acid)) and the substrate turnover measured at a wavelength of 405 nm (y-axis). Clones are presented on the x-axis, the first number indicates the round of panning, the second one is the clone number; S. is the abbreviation for clones prior to the first round of selection. Clones S.1-3 have a combination of k8 light chain with one random Ig delta heavy chain Id-segment and represent negative controls.

FIG. 6. DNA- and protein-sequence of the human kappa 8 light chain variable region. Numbers indicate the nucleotide (nt) positions, amino acids are presented in single letter code CDR1 includes nt 70 to nt 102, CDR2 nt 148 to nt 168, CDR3 nt 265 to nt 294 (SEQ ID NO:141).

FIG. 7. DNA-sequence of the human D4.5 heavy chain variable region. Numbers indicate the nucleotide (nt) positions, amino acids are presented in the single letter code. CDR1 includes nt 91 to nt 105, CDR2 nt 148 to nt 198, CDR3 nt 292 to nt 351. The border between the heavy chain variable region and the CH1 domain of the Ig delta constant region is located between nt 382 and nt 383 with the delta constant region protein sequence starting at nt 384 (SEQ ID NO:143).

FIG. 8. DNA-sequence of the human D7.2 heavy chain variable region. Numbers indicate the nucleotide (nt) positions, amino acids are presented in the single letter code. CDR1 includes nt 91 to nt 105, CDR2 nt 148 to nt 198, CDR3 nt 292 to nt 309. The border between the heavy chain variable region and the CH1 domain of the Ig delta constant region is located between nt 340 and nt 31 with the delta constant region protein sequence starting at nt 343 (SEQ ID NO:145).

FIG. 9. DNA- and protein-sequence of the human kappa 5.1 light chain variable region. Numbers indicate the nucleotide (nt) positions, amino acids are presented in single letter code CDR1 includes nt 70 to nt 102, CDR2 nt 148 to nt 168, CDR3 nt 265 to nt 294 (SEQ ID NO:147).

Figure 10:
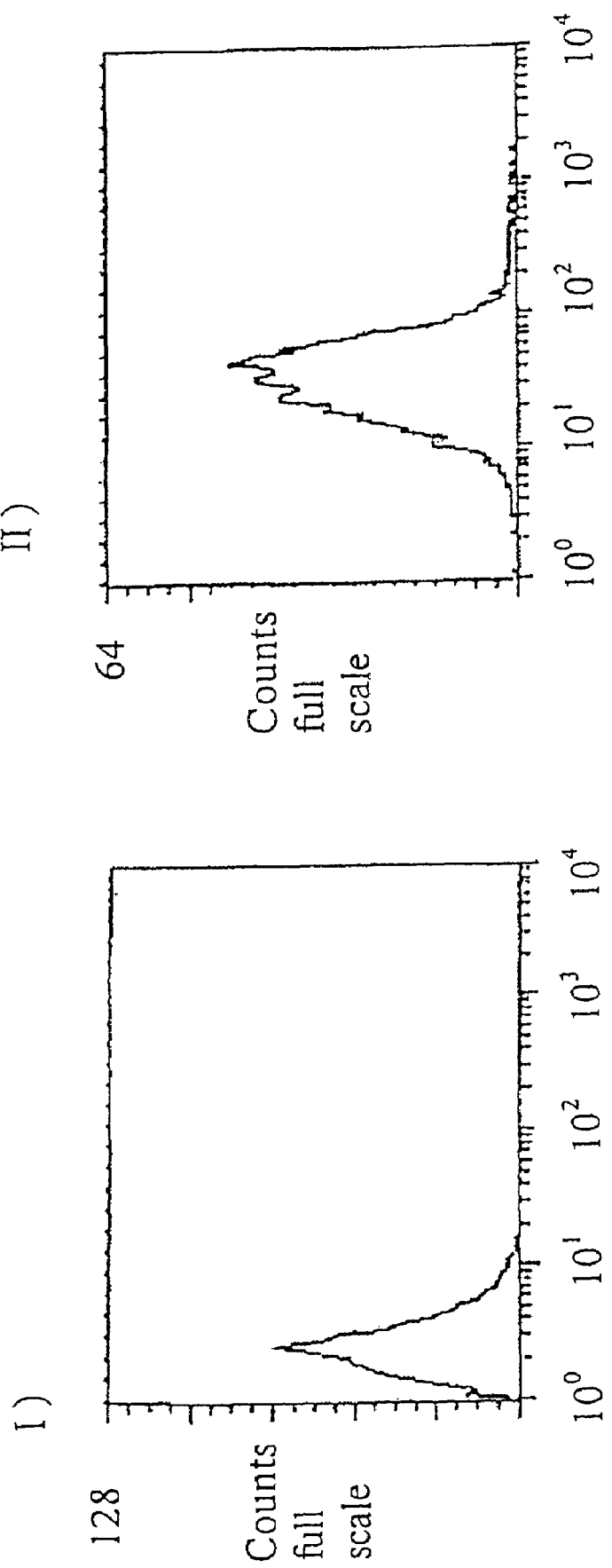
Figure 10:
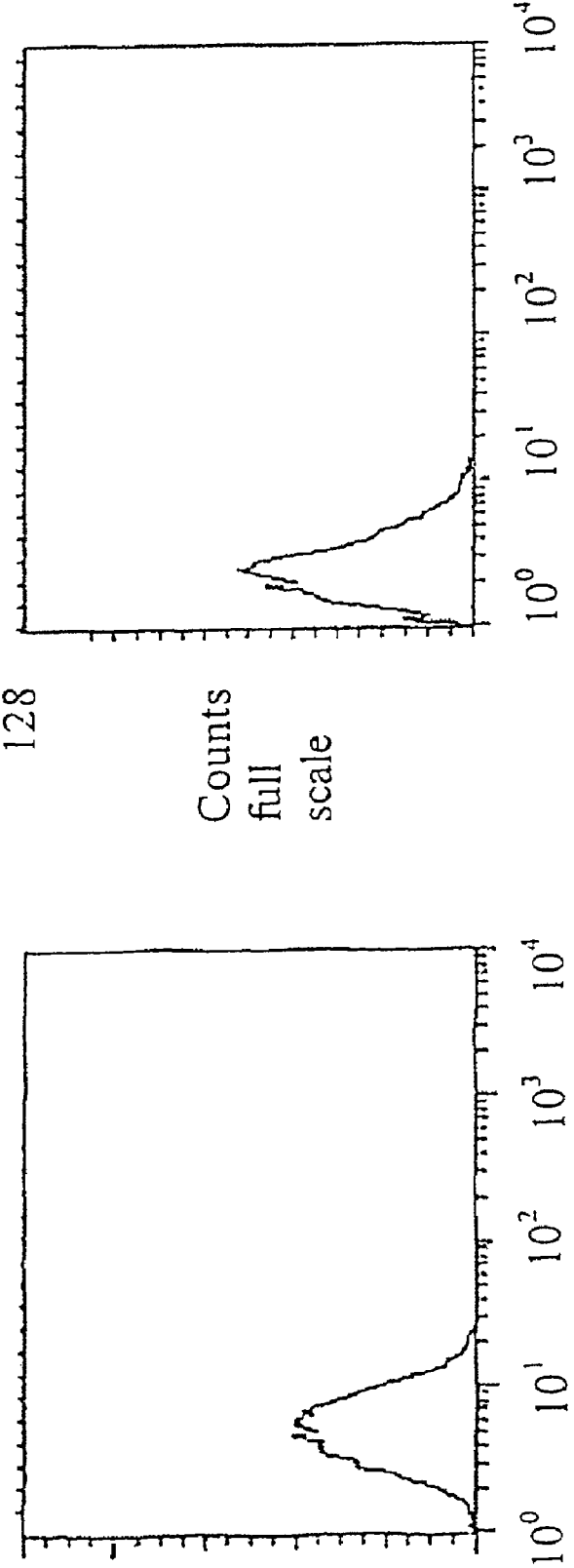

FIG. 10. Flow cytometry analysis of Fab antibody-fragments and control antibody M79 on 17-1A positive Kato cells for testing binding activity of a periplasma preparation containing the k8-D4.5-Fab fragment. Kato-cells were incubated with I) irrelevant periplasma preparation, 11) 10 µg/ml chimeric (bivalent !) M79, III) k8-D4.5 periplasma preparation and IV) 1:10 dilution of K8-D4.5 periplasma preparation. Relative cell numbers are shown on the y-axis, relative fluorescense intensity is shown on the x-axis.

Figure 11:
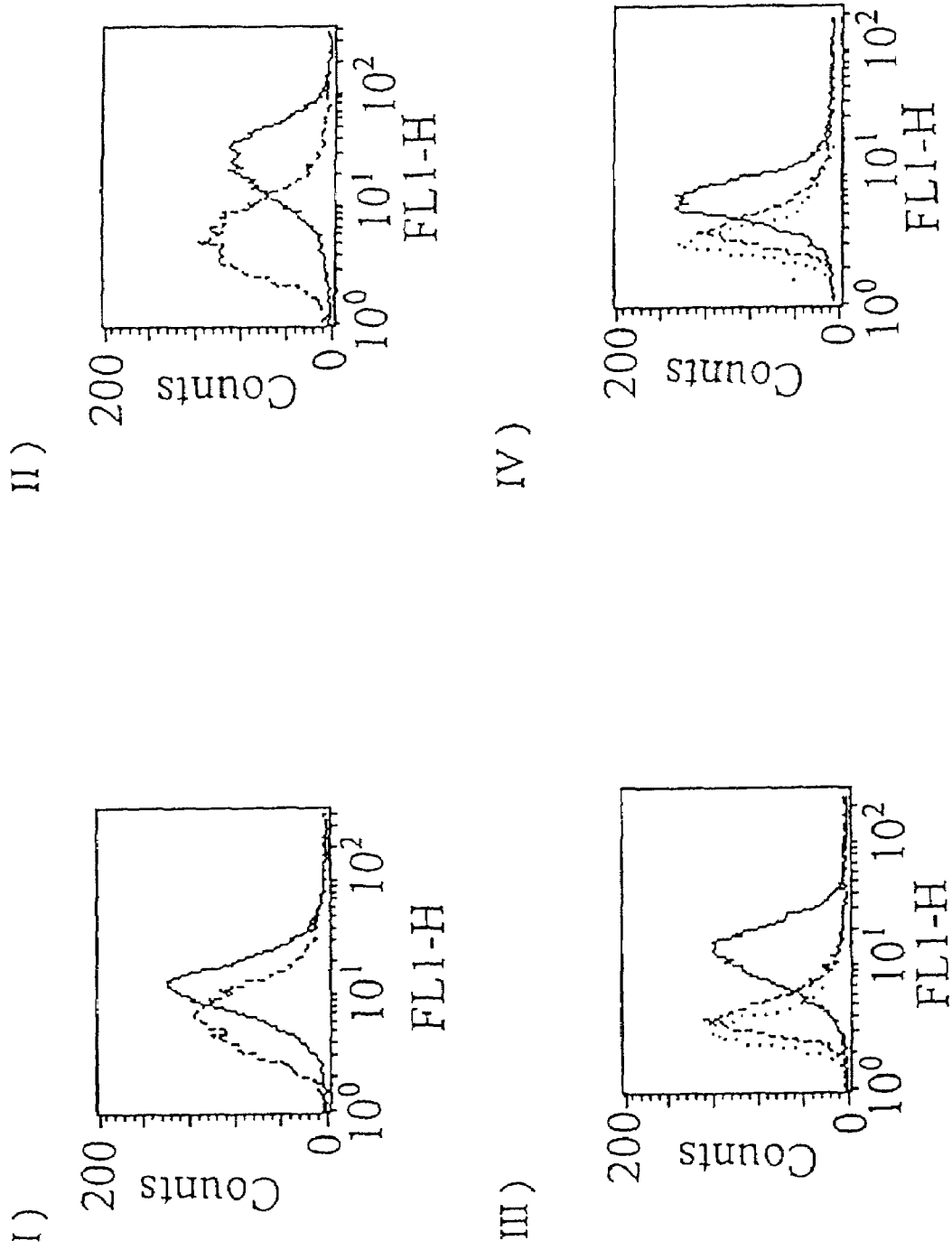
Figure 11:
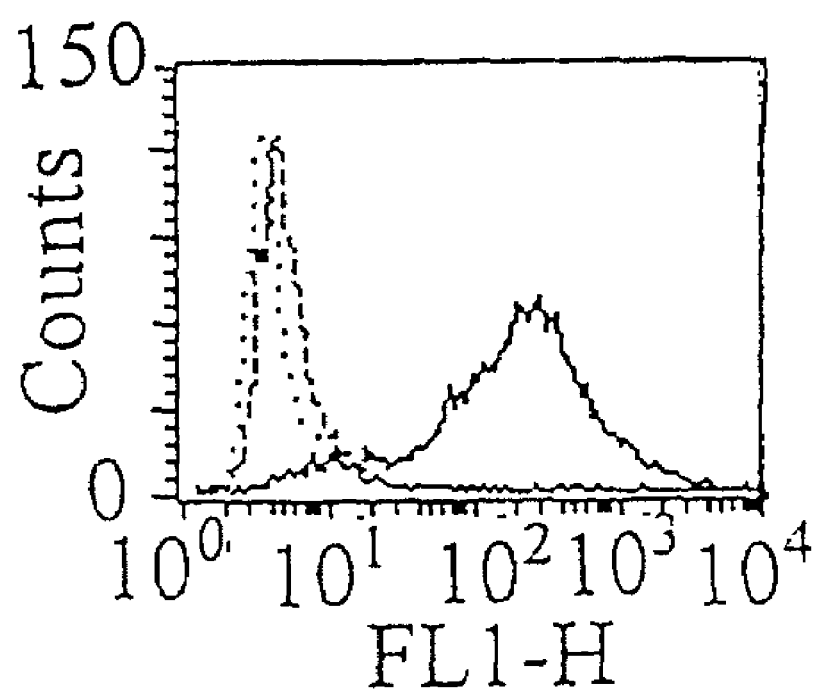

FIG. 11. Flow cytometry analysis of Fab antibody-fragments and complete antibodies on 17-1A positive Kato cells, 17-A transfected and untransfected CHO-cells, respectively, for testing binding activity of periplasma preparations (pp) containing the k8-D4.5-, the k5.1-D4.5- or an irrelevant k-D4.5-Fab-fragment. Kato-cells were incubated I) with irrelevant pp (broken line) or k5.1-D4.5-pp (solid line), or II) with 20 µg/ml M79-antibody (solid line) or the corresponding murine IgG2a isotype control (broken line). 17-1A-transfected CHO-cells were incubated III) with irrelevant pp (broken line) or k5.1-D4.5-pp (solid line), IV) with irrelevant pp (broken line) or k8-D4.5-pp (solid line), or V) with 20 jig/ml M79-antibody (solid line) or the corresponding murine IgG2a isotype control (broken line). In III), IV) and V) incubation and detection of relevant pp (k5.1-D4.5Fab-pp and k8-D4.5-Fab-pp, respectively) and the murine antibody M79 was also carried out on untransfected CHO-cells (dotted lines). Relative cell numbers are shown on the y-axis, relative fluorescense intensity is shown on the x-axis.

Figure 12:
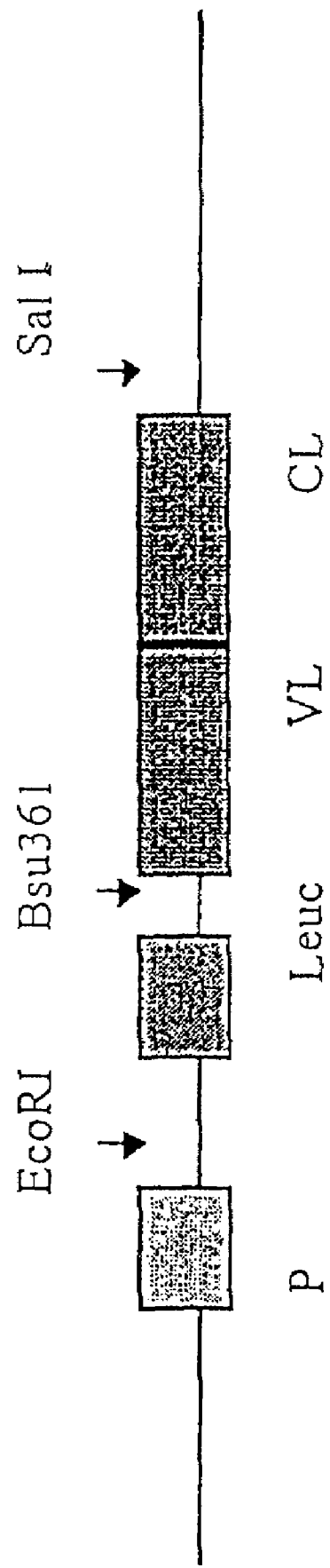

FIG. 12. Cloning site of pEF-ADA with important restriction sites. The following abbreviations were used: P, promotor; VL, variable light chain domain; CL, constant light chain; Leuc, eucaryotic leader sequence.

Figure 13:
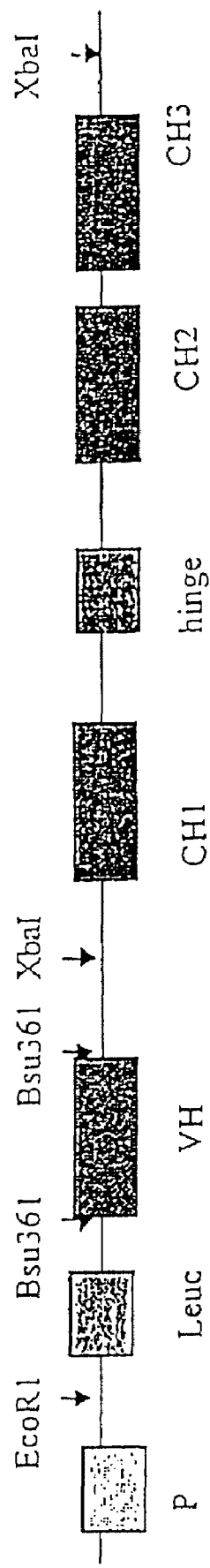

FIG. 13. Cloning site of pEF-DHFR with important restriction sites. The following abbreviations were used: P, promotor; VH, variable heavy chain domain; CH 1/2/3, constant heavy chain domain 1/2/3; Leuc, eucaryotic leader sequence.

Figure 14:
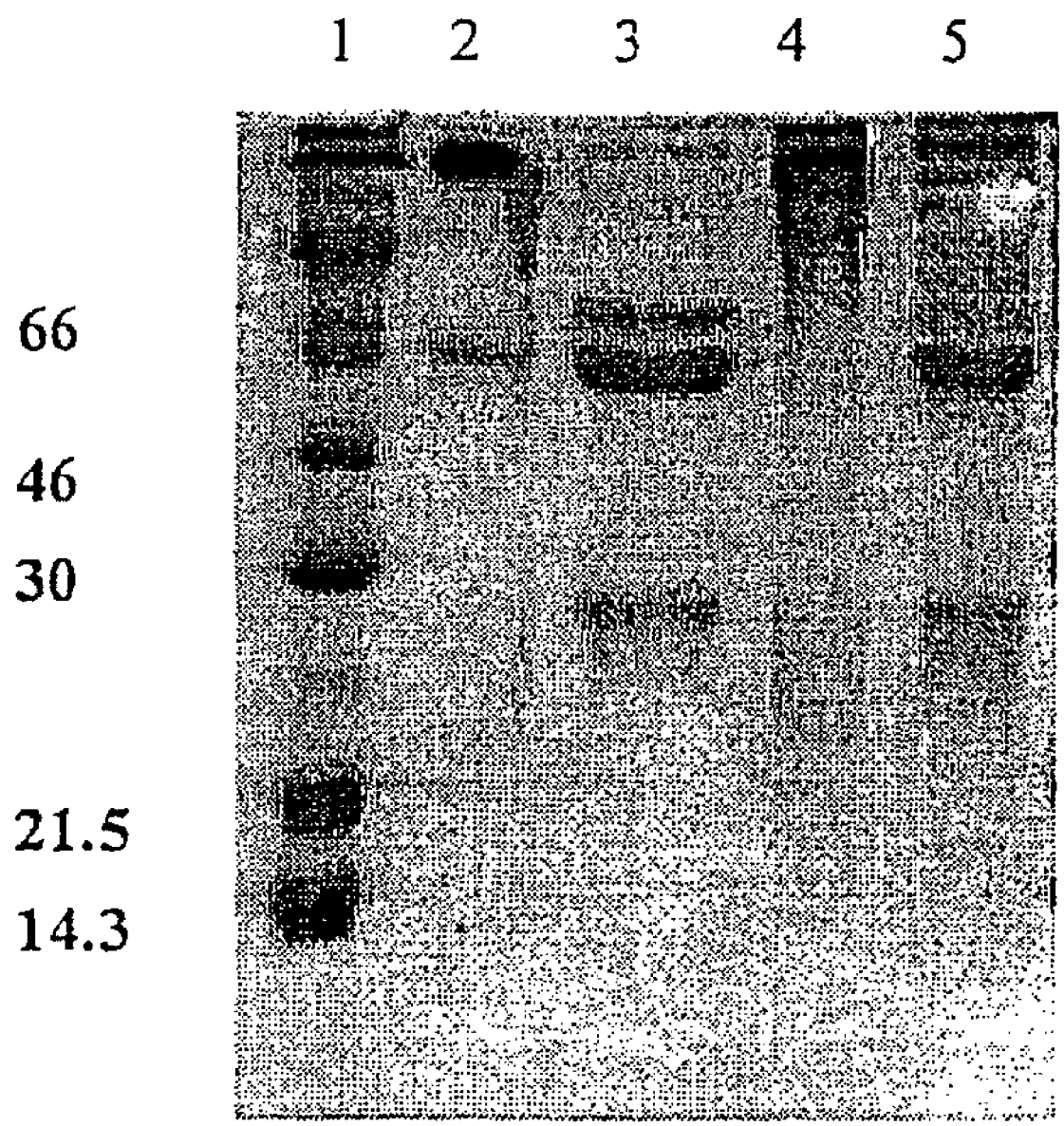

FIG. 14. DS-PAGE of preparations of the human antibody H79. Approx. 10 µG of each antibody were run on a 12.5 denaturating Polyacrylamid-gel under reducing and non-reducing conditions and stained with coomassie blue.

Lane 1: Marker (MW [kDa] of single bands marked on the left side of the gel)

Lane 2: H79 human IgG1-version (non-reducing)

Lane 3: H79 human IgG1-version under reducing conditions

Lane 4: H79 murine IgG1-version (non-reducing)

Lane 5: H79 murine IgG1-version under reducing conditions

Figure 15:
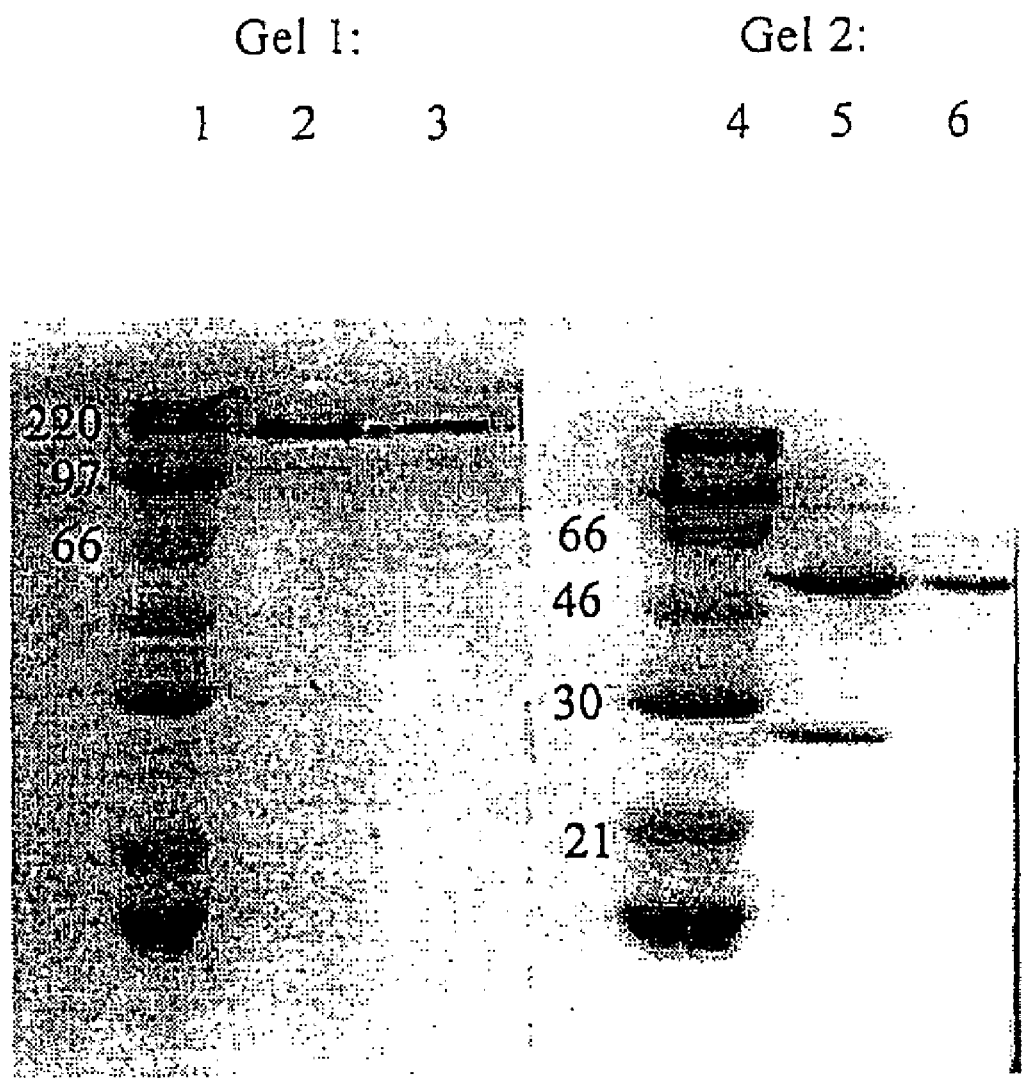

FIG. 15. SDS-PAGE of preparations of the human antibodies H79 and HD70. 10 μg of H79 and 3.5 μg HD70 were run on 12.5% denaturating Polyacrylamid-gel under non-reducing (gel 1) and reducing (gel 2) conditions and stained with coomassie blue.

Gel: Lane 1: Marker (MW [kDa] of single bands marked on the left side of the gel) Lane 2: H79 human IgG1-version (non-reducing)

Lane 3: HD70 human IgG1-version (non-reducing)

Gel 2: Lane 4: Marker (MW [kDa] of single bands marked on the left side of the gel) Lane 5: H79 human IgG1-version under reducing conditions Lane 6: HD70 human IgG1-version under reducing conditions FIG. 16. Flow cytometry analysis of 17-1A positive Kato cells for testing binding activity of purified H79 human IgG1 as well as purified H79 murine IgG1. Katocells were incubated with IgG isotype-controls (10 μg/ml human IgG1 and murine IgG1, respectively), positive controls (M79 and chimerized M74 at 10 μg/ml, respectively; (both 17-1A specific) and with H79 human IgG1 or H79 murine IgG1 (10 μg/ml and 1 μg/ml each). Relative cell numbers are shown on the y-axis, relative fluorescense intensity is shown on the x-axis.

FIG. 17. Flow cytometry analysis of antibodies (concentration: 20 μg/ml each) on 17-1A positive Kato cells, 17-1A-transfected and non-transfected CHO-cells for testing binding activity of the purified antibodies H79 human IgG1, H79 murine IgG1, HD70, D7.2, M79, Panorex and isotype controls (human IgG1, murine IgG1 and 2a). I) H79 human IgG1 (solid line) and human IgG1 isotype control (broken line) on Kato-cells, 11) H79 murine IgG1 (solid line) and murine IgG1 isotype control (broken line) on Kato-cells, III) HD70 (solid line) and human IgG1 isotype control (broken line) on Kato-cells, IV) D7.2 (solid line) and human IgG1 isotype control (broken line) on Kato-cells, V) M79 (solid line) and murine IgG2a isotype control (broken line) on Kato-cells, VI) Panorex (solid line) and murine IgG2a isotype control (broken line) on Kato-cells, VII) H79 human IgG1 (solid line) and human IgG1 isotype control (broken line) on 17-1A-transfected CHO cells, VIII) H79 murine IgG1 (solid line) and murine IgG1 isotype control (broken line) on 17-1A-transfected CHO-cells, IX) HD70 (solid line) and human IgG1 isotype control (broken line) on 17-1A-transfected CHO-cells, X) D7.2 (solid line) and human IgG1 isotype control (broken line) on 17-1A-transfected CHO-cells, XI) M79 (solid line) and murine IgG2a isotype control (broken line) on 17-1A-transfected CHO-cells, XII) Panorex (solid line) and murine IgG2a isotype control (broken line) on 17-1A-transfected CHO-cells. Figures VII-XII also show the results of incubation and detection of the relevant antibodies on non-transfected CHO-cells (dotted line).

Figure 18:
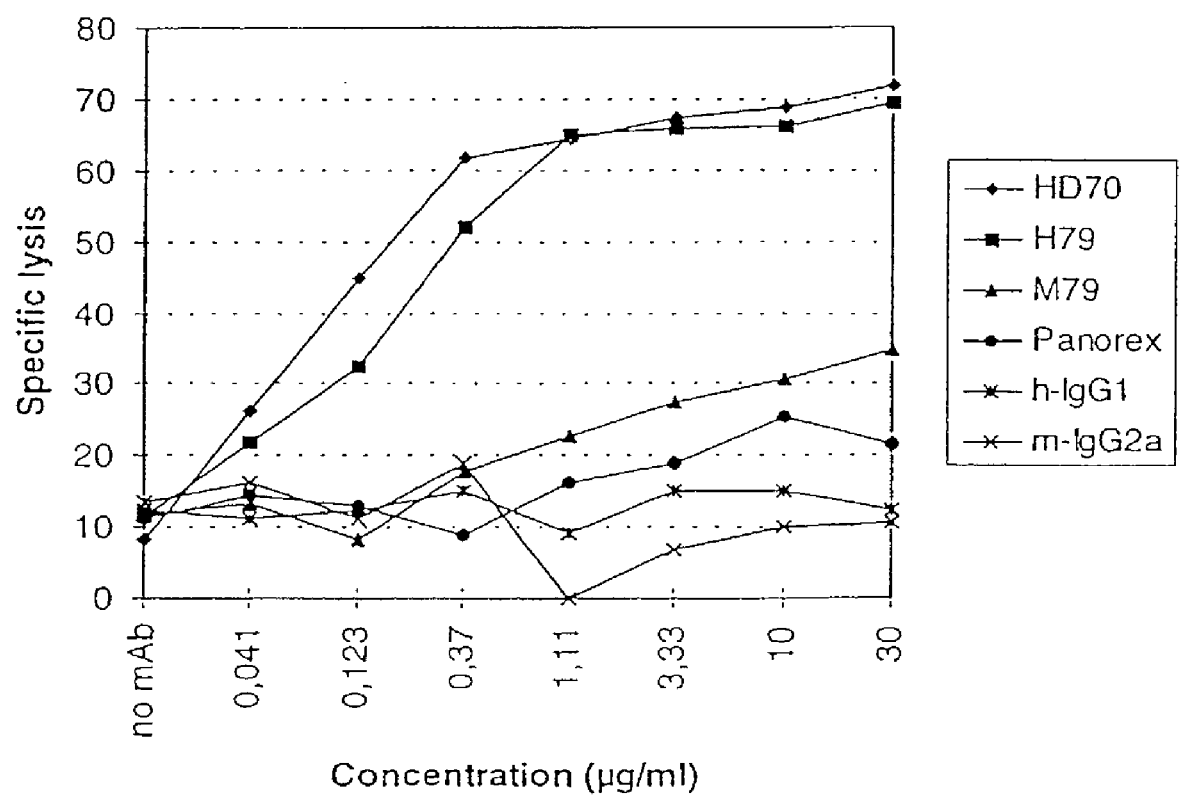

FIG. 18. $^{51}$Cr antibody dependent cellular cytotoxicity assay. For 51Cr release unstimulated human peripheral blood mononuclear cells (PBMCs, 5×105 cells) as effector cells were incubated with labelled target cells (Kato-cells labelled for 2 h with 51Cr) and antibodies in different concentrations for 4 h or 20 h at 37° C. Corresponding non-binding isotypes (h-IgG=human IgG1; m-IgG2a=murine IgG2a) were used as negative controls (H79=H79huIgG1). Specific lysis was calculated as ((cpm, experimental release)−(cpm, spontaneous release))/((cpm, maximal release)−(cpm, spontaneous release)).

Figure 19:
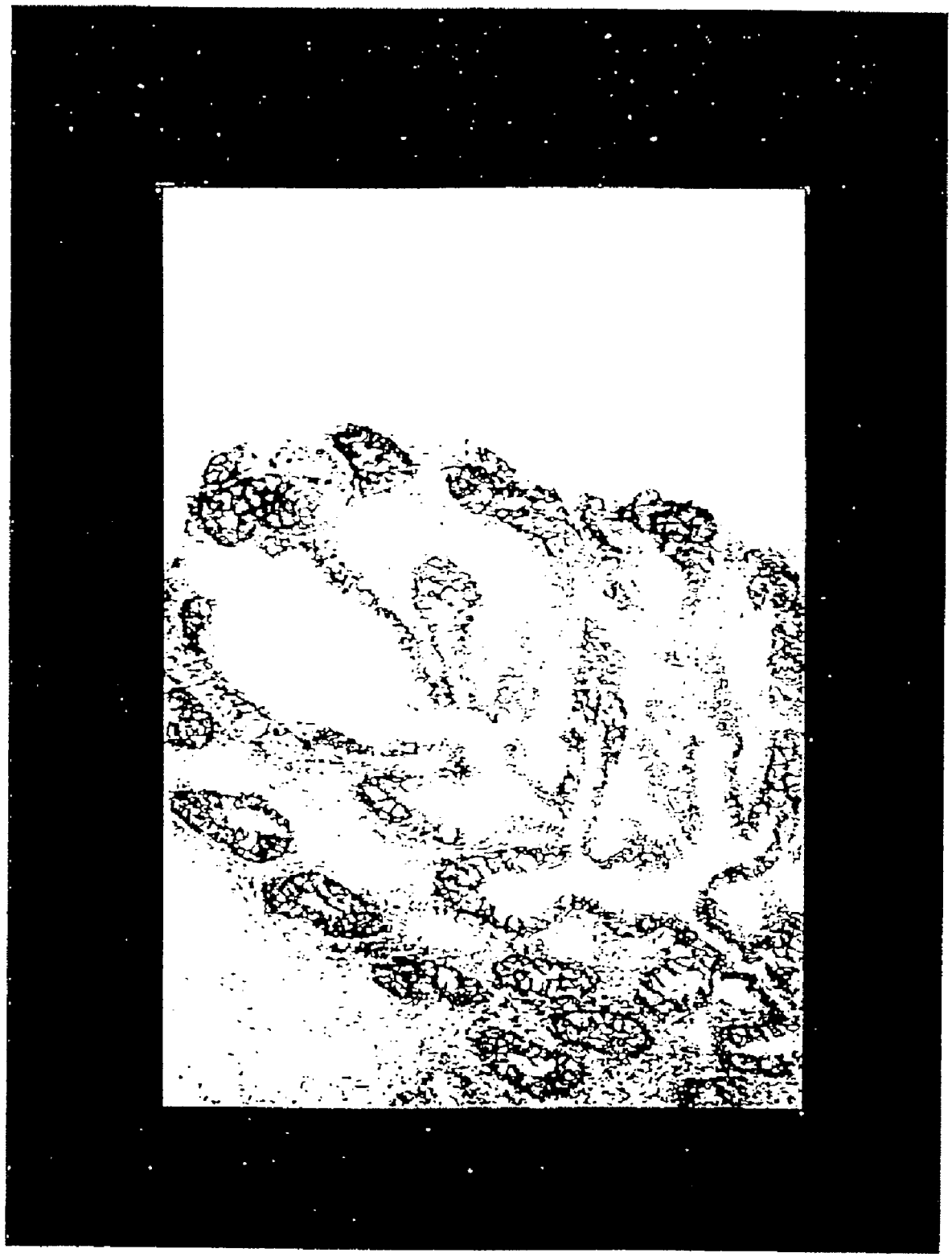

FIG. 19. Light microscopic photo of healthy human colon tissue stained with M79 (positive) control. 5 nm cryosections of normal mucosa tissue were incubated with the murine M79 antibody (IgG2a) as positive control (10 μg/ml). Detection of bound murine antibodies was carried out with a peroxidase conjugated polyclonal anti-mouse-Ig antibody and stained with carbazole (brown). Counter staining was carried out with hemalaun (blue).

Figure 20:
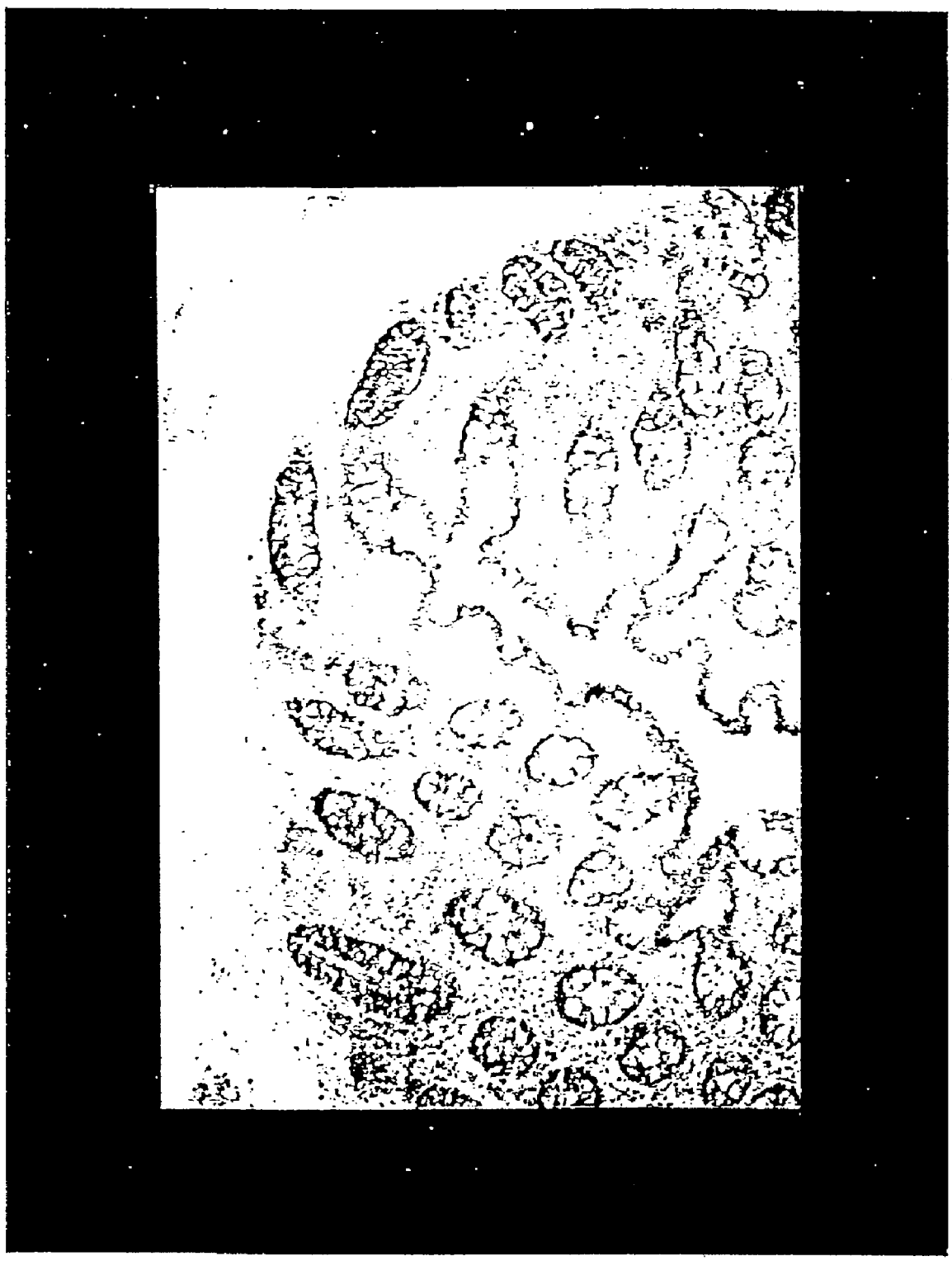

FIG. 20. Light microscopic photo of healthy human colon tissue stained with H79 murine IgG1. 5 nm cryosections of normal mucosa tissue were incubated with the murine IgG version of the H79 antibody (10 μg/ml). Detection of bound murine IgG1 antibodies was carried out with a peroxidase conjugated polyclonal anti-mouse-Ig antibody and stained with carbazole (brown). Counter staining was carried out with hemalaun (blue).

Figure 21:
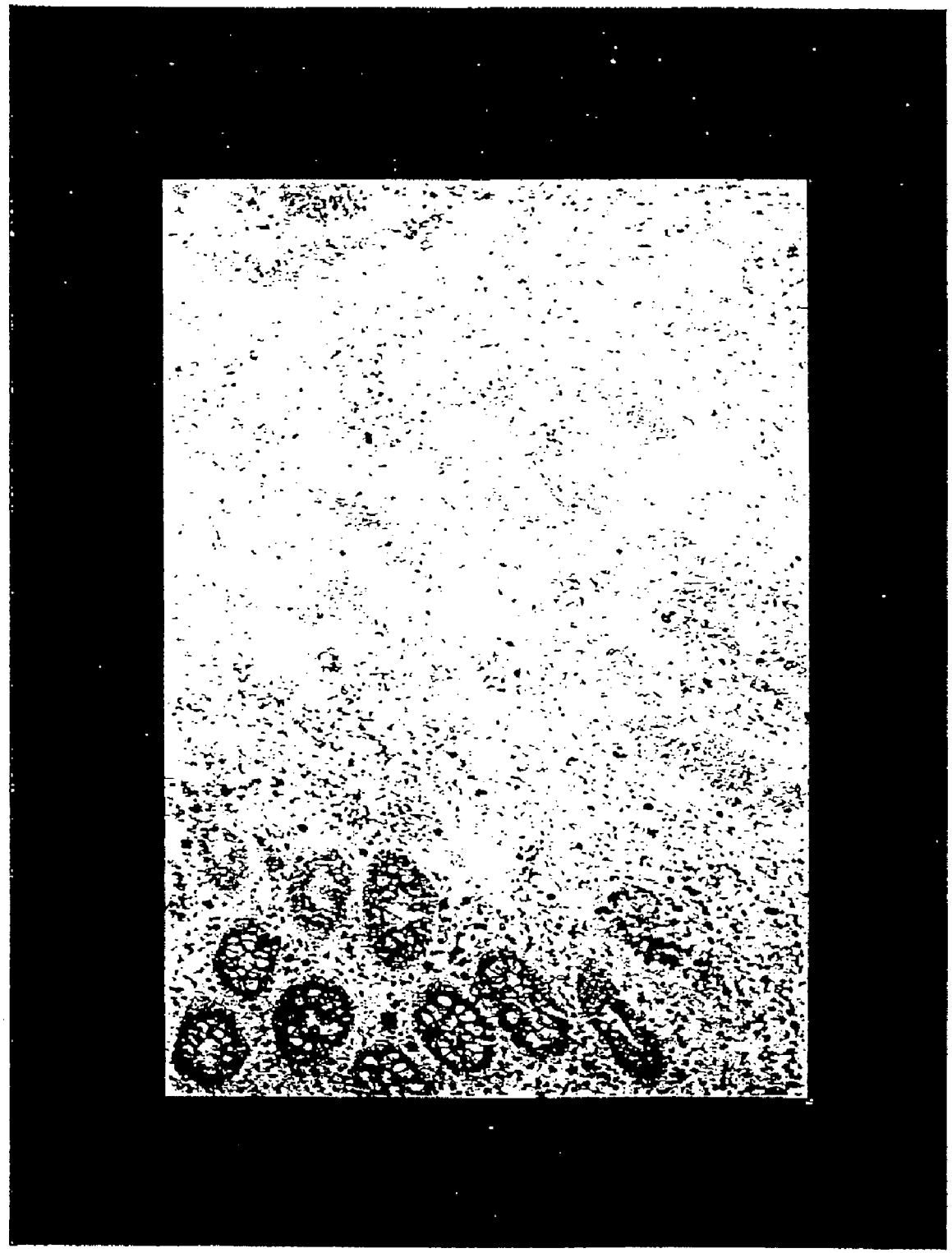

FIG. 21. Light microscopic photo of colon carcinoma stained with M79 (positive control). 5 nm cryosections colon carcinoma were incubated with the murine M79 antibody (IgG2a) as positive control (10 μg/ml). Detection of bound murine antibodies was carried out with a peroxidase conjugated polyclonal anti-mouseIg antibody and stained with carbazole (brown). Counter staining was carried out with hemalaun (blue).

Figure 22:
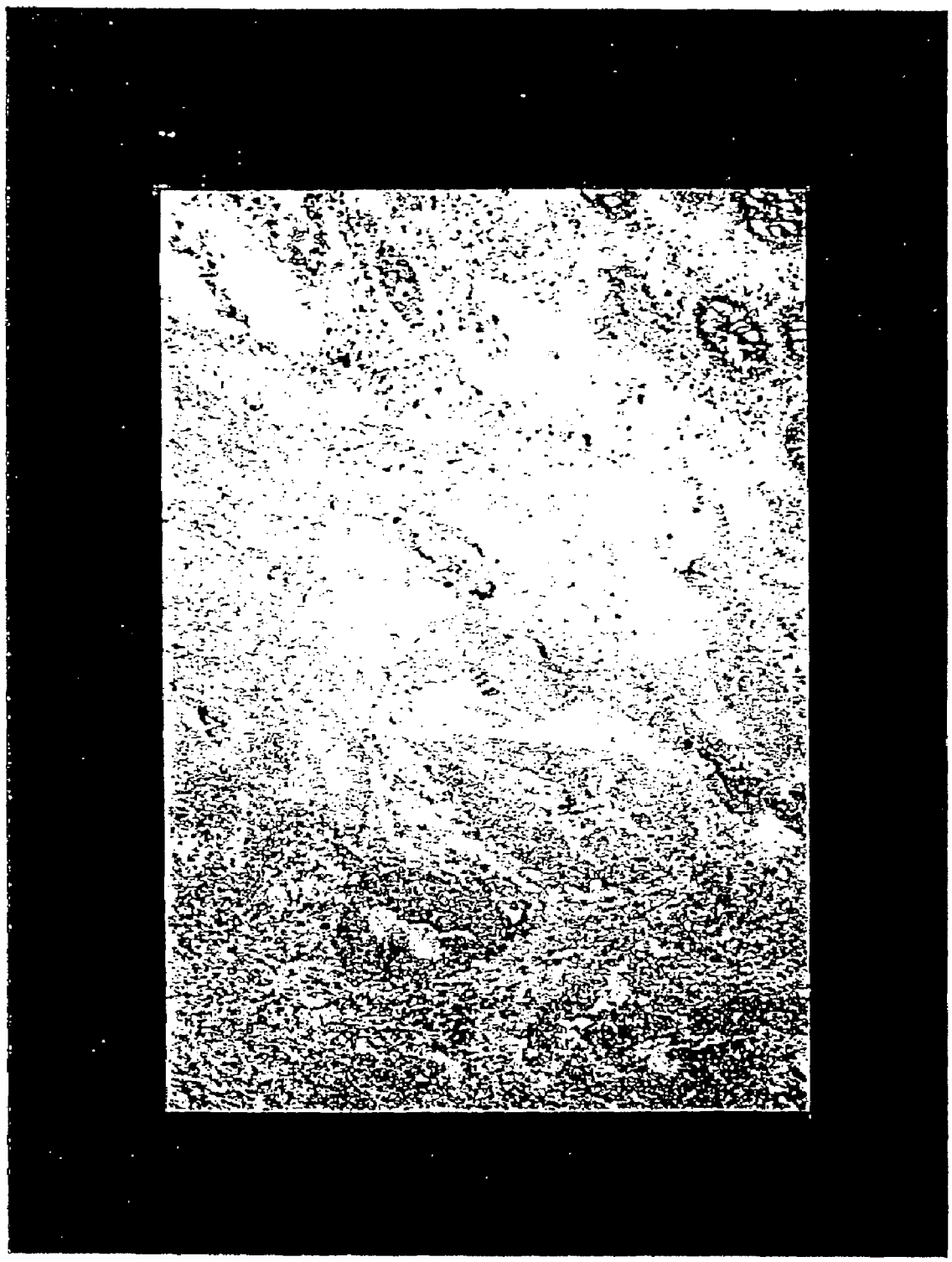

FIG. 22. Light microscopic photo of colon carcinoma stained with H79 murine IgG1. 5 run cryosections of colon carcinoma tissue were incubated with the murine IgG1 version of the H79 antibody (10 μg/ml). Detection of bound murine IgG1 antibodies was carried out with a peroxidase conjugated polyclonal anti-mouse-Ig antibody and stained with carbazole (brown). Counter staining was carried out with hemalaun (blue).

Figure 23:
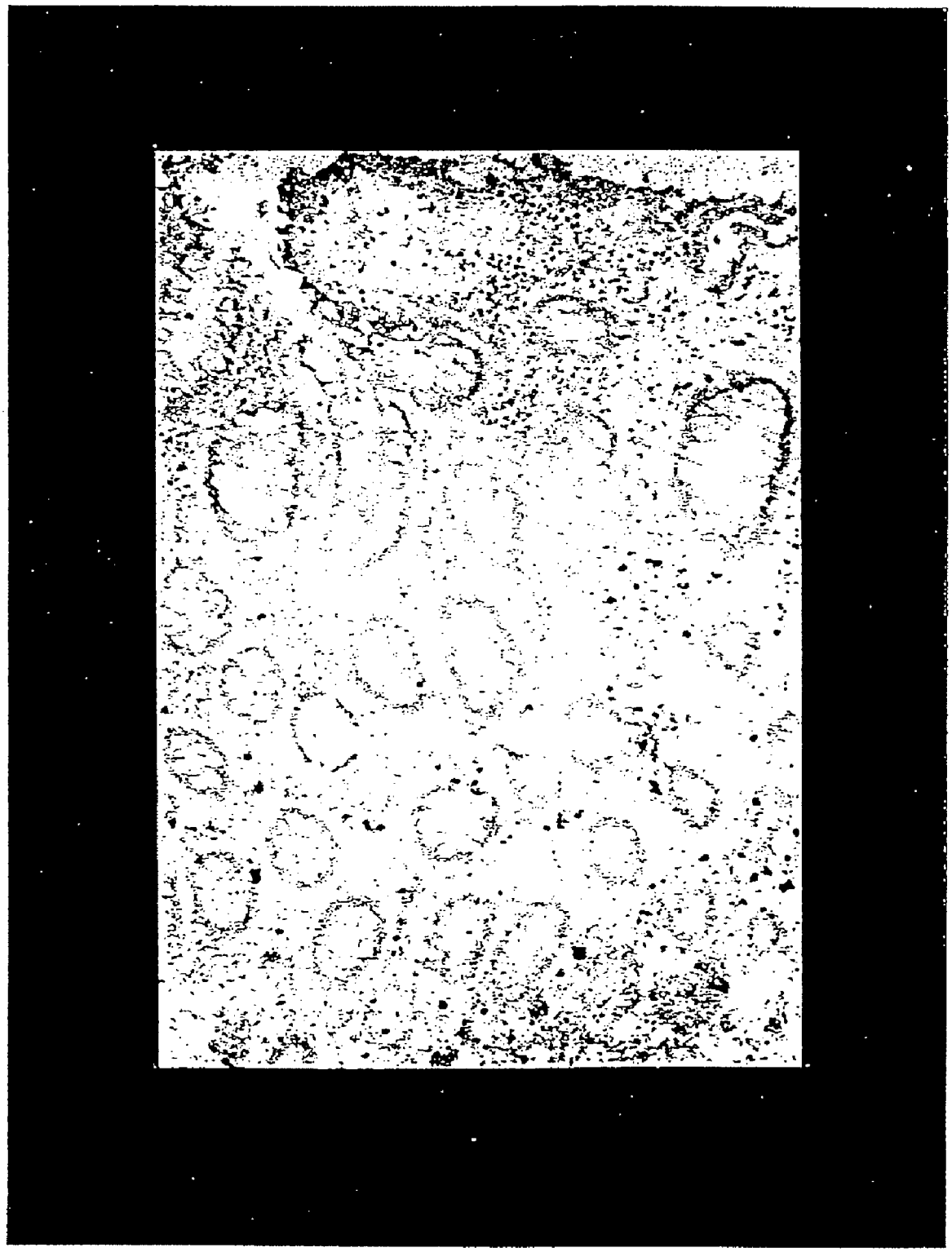

FIG. 23. Light microscopic photo of healthy human colon tissue stained with murine IgG2a isotype control 5 nm cryosections of normal mucosa tissue were incubated with irrelevante murine IgG2a antibody as negative control (10 μg/ml). Detection of bound murine antibodies was carried out with a peroxidase conjugated polyclonal anti-mouse-Ig antibody and stained with carbazole (brown). Counter staining was carried out with hemalaun (blue).

Figure 24:
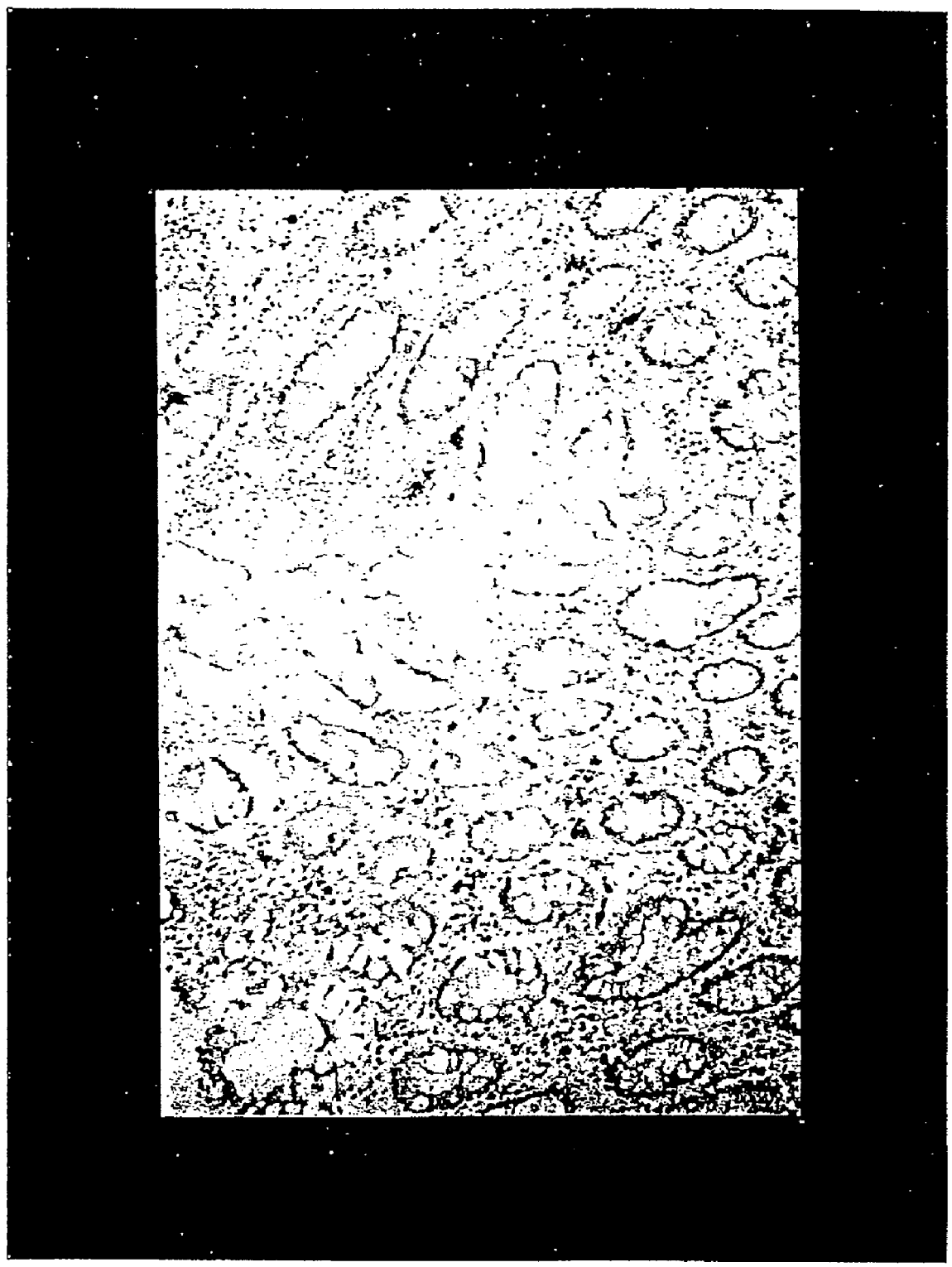

FIG. 24. Light microscopic photo of healthy human colon tissue stained with IgG1 isotype control 5 nm cryosections of normal mucosa tissue were incubated with irrelevante murine IgG1 antibody as negative control (10 μg/ml). Detection of bound murine antibodies was carried out with a peroxidase conjugated polyclonal anti-mouse-Ig antibody and stained with carbazole (brown). Counter staining was carried out with hemalaun (blue).

Figure 25:
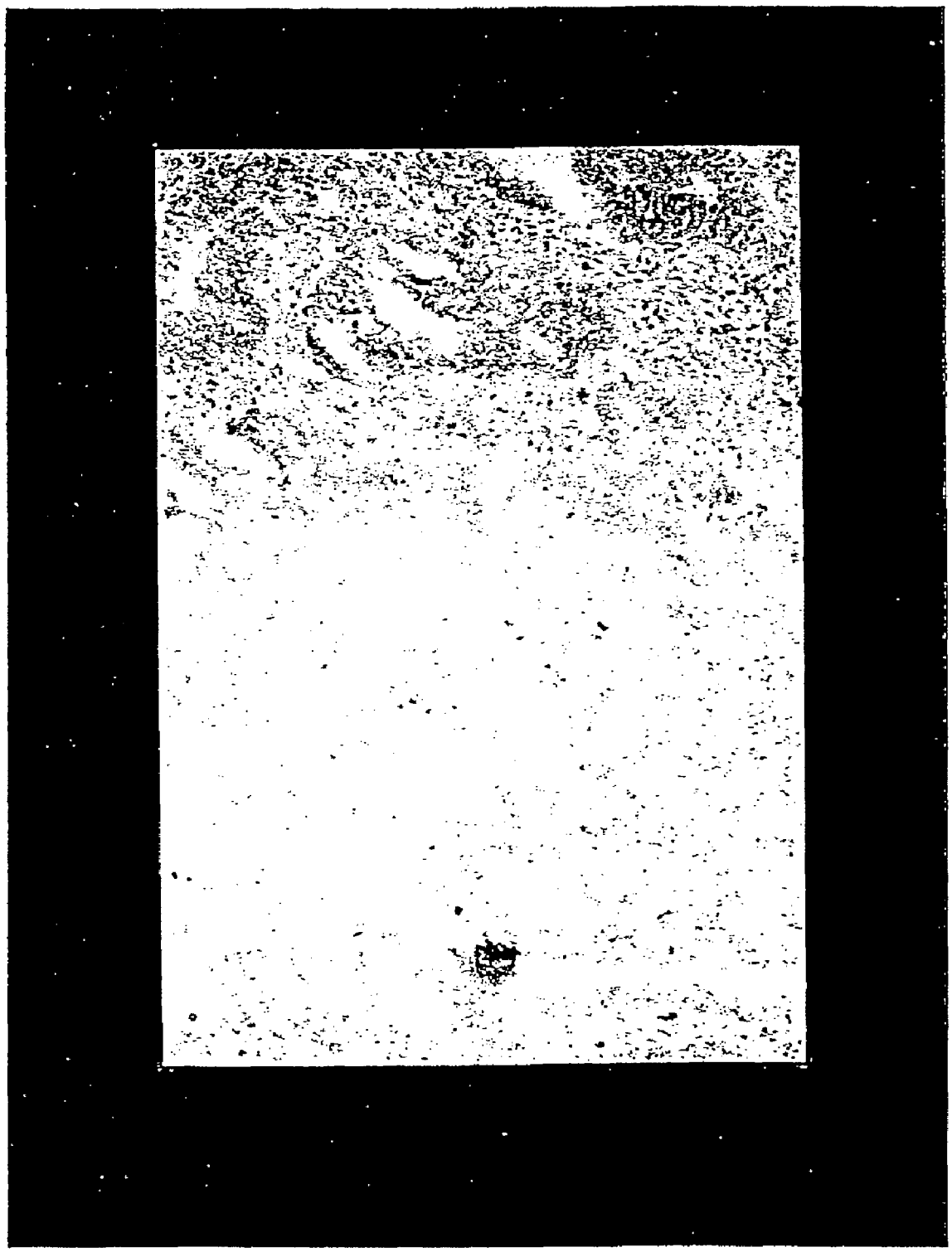

FIG. 25. Light microscopic photo of human colon carcinoma tissue stained with murine IgG2a isotype control 5 nm cryosections of normal mucosa tissue were incubated with irrelevante murine IgG2a antibody as negative control (10 μg/ml). Detection of bound murine antibodies was carried out with a peroxidase conjugated polyclonal anti-mouse-Ig antibody and stained with carbazole (brown). Counter staining was carried out with hemalaun (blue).

Figure 26:
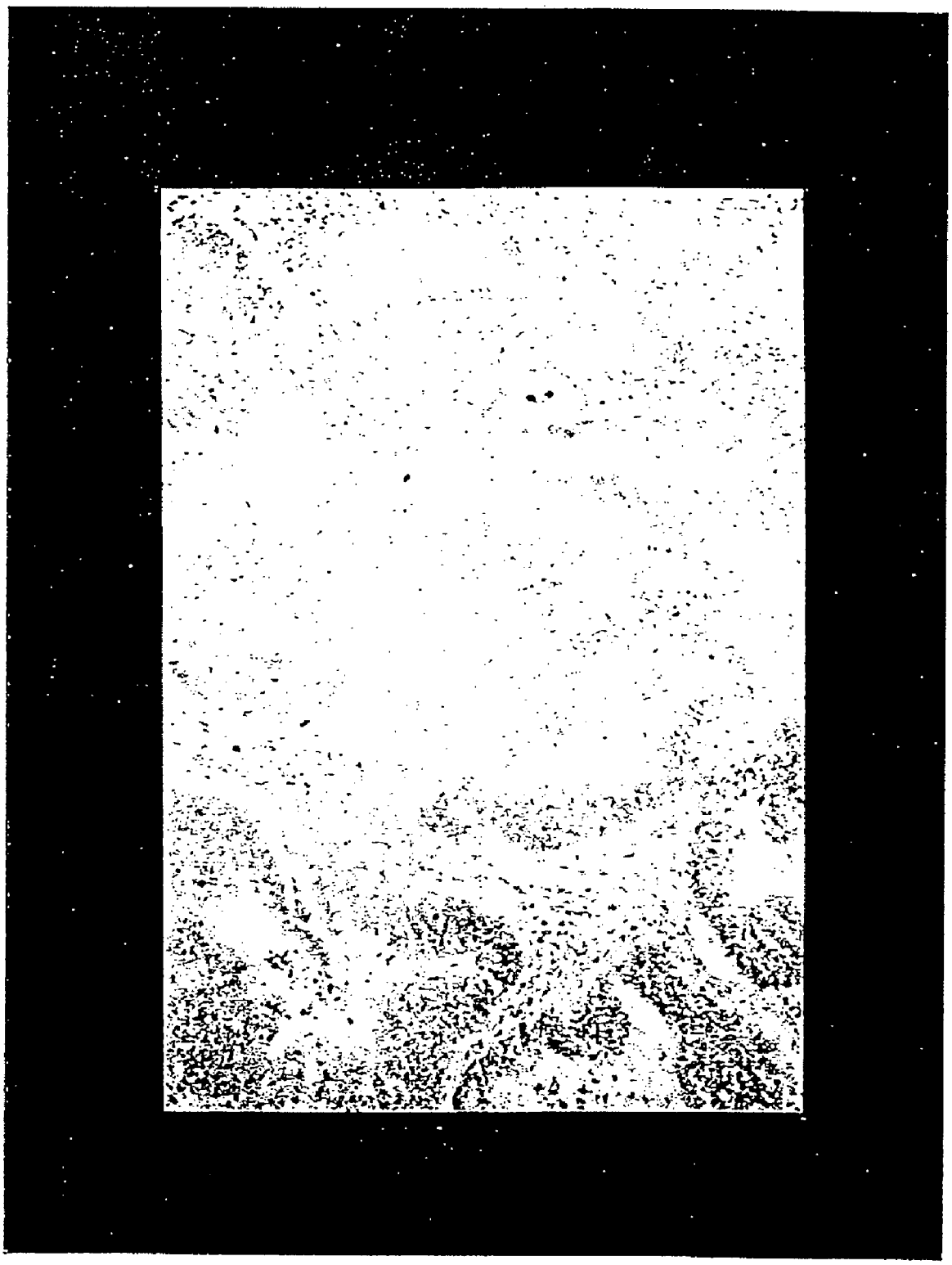

FIG. 26. Light microscopic photo of human colon carcinoma tissue stained with IgG1 isotype control 5 nm cryosections of normal mucosa tissue were incubated with irrelevante murine IgG1 antibody as negative control (10 μg/ml). Detection of bound murine antibodies was carried out with a peroxidase conjugated polyclonal anti-mouse-Ig antibody and stained with carbazole (brown). Counter staining was carried out with hemalaun (blue).

FIG. 27. Epitope analysis of murine antibody M79 and human antibodies H79 and HD70, each of which is specific for the human 17-1A antigen. Antibodies were incubated with a gridded array of peptides comprising 119 polypeptides of 13 amino acids, shifted by two amino acids and covering the entire extracellular amino acid sequence of the human 17-1A-antigen. The peptides were covalently attached at their C-termini to a Pep Spots Membrane (Jerini Biotools, Berlin) as individual spots. Bound murine M79 antibody was directly detected on the Pep Spots Membrane by an anti-murine immunoglobulin antibody coupled to horse radish peroxidase (HRP) followed by chemoluminescence. Signals that are due to the reactivity of the secondary antibody alone with single peptide spots are shown in the corresponding control staining of the Pep Spots Membrane. By subtracting the main background staining at peptide spot 87, peptide spots 38 and 95 turn out to represent specific binding of murine antibody M79. Due to a higher degree of crossreactivity of the secondary HRP-conjugated anti-human immunoglobulin antibody with several peptide spots, bound human antibodies H79 and HD70 were transferred from the Pep Spots Membrane to a blotting membrane, respectively, by means of electrotransfer and subsequently detected by said anti human secondary antibody and chemoluminescence. Specific binding of human antibody H79 could be detected mainly at peptide spots 8, 11, 13, 14, 59-60, 77 and 79; however, no binding was detectable in case of human antibody HD70. The Examples illustrate the invention:

EXAMPLE I

Construction of the Combinatorial Antibody Libraries and Phage Display

A library of human immunoglobuline (Ig) light chain and Ig heavy chain Fd-DNA-fragments was constructed by RT-PCR with kappa-, lambda- and Fd delta specific primer sets on the total RNA prepared from peripheral blood lymphocytes (PBL)- and bone marrow-samples of four and ten human donors, respectively according to Chomczynski, Analytical Biochemistry 162 (1987) 156-159. cDNA was synthesized according to standard methods (Sambrook, Cold Spring Harbor Laboratory Press 1989, second edition).

The following primer sets were chosen, giving rise to a 5'-XhoI and a 3'-SpeI recognition site for the heavy chain fragments and a 5'-SacI and a 3'-XbaI recognition site for light chains:

For the PCR-amplification of the delta Fd cDNA-fragments five different 5'-VH-family specific primers were each combined with one 3'-CH 1 delta primer; for the PCR-amplification of the kappa (K) light chain fragments five different 5'-VK-family specific primers were each combined with one 3'-CK primer and for the amplification of the lambda (L) light chain fragments, eight different 5'-VL-family specific primers were combined with one 3'-CL-primer.

Primer sets for the amplification of the Fab DNA-fragments (5' to 3') are shown in Table I below.

The following PCR-program was used for amplification:

Denaturation at 94° C. for 15 seconds, primer annealing at 52° C. for 50 seconds and primer extension at 72° C. for 90 seconds for 40 cycles, followed by a 10 minutes final extension at 72° C.

TABLE 1

PRIMER SETS

| | | SEQ ID NO: |
|---|---|---|
| VH1,3,5,7: | Aggtgcagctgctcgagtctgg | 149 |
| VH2: | Cagagtcaccttgctcgagtctgg | 150 |
| VH4: | Caggtgcagctgctcgagtcggg | 151 |
| VH4B: | Caggtgcagctactcgagtgggg | 152 |
| VH6: | Caggtacagctgctcgagtcagg | 153 |
| 3'-primer | | |
| CD 1: | Tgccttactgtctctggccagcggaagat | 154 |
| Kappa chain fragment 5'-primer: | | |
| VK1: | Gagccgcacgagcccgagctccagatgacccagtctcc | 155 |
| VK3: | Gagccgcacgagcccgagctcgtgattgacagcagtctcc | 156 |
| VK2/4: | Gagccgcacgagcccgagctcgtgatgacctcagtctcc | 156 |
| VK5: | Gagccgcacgagcccgagctcacactcacgcagtctcc | 157 |
| VK6: | Gagccgcacgagcccgagctcgtgctgactcagtctcc | 158 |
| 3'-primer | | |
| CK1D: | Gcgccgtctagaattaacactctcccctgttgaagctctttgtgacgggcgaactcag | 159 |
| Lambda chain fragment: 5'-primer: | | |
| VL1: | Aattttgagctcactcagccccac | 160 |
| VL2: | Tctgccgagctccagcctgcctccgtg | 161 |
| VL3: | Tctgtggagctccagccgccctcagtg | 162 |
| VL4: | Tctgaagagctccaggaccctgttgtgtctgtg | 163 |
| VL5: | Cagtctgagctcacgcagccgccc | 164 |
| VL6: | Cagactgagctcactcaggagccc | 165 |
| VL7: | Caggttgagctcactcaaccgccc | 165 |
| VL8: | Caggctgagctcactcagccgtcttcc | 166 |
| 3'-primer: | | |
| CL2: | Cgccgtctagaattatgaacattctgtagg | 167 |

450 ng of the kappa light chain fragments (digested with SacI and XbaI) were ligated with 1400 ng of the phagmid pComb3H (digested with SacI and XbaI; large DNA-fragment) derived from pComb3 (Barbas, Proc. Natl. Acad. Sci. U.S.A. 88 (1991) 7978-7982) wherein the heavy chain position was already occupied by the Fd fragment of the chimerized murine antibody M79 (containing a human IgG1 CH1)

directed against the extracellular part of the 17-1A protein (see FIG. 1 for pComb3H cloning site).

The resulting combinatorial antibody DNA library was then transformed into 300 μl of electrocompetent *Escherichia coli* XL1 Blue by electroporation (2.5 kV, 0.2 cm gap cuvette, 25 FD, 200 Ohm, Biorad gene-pulser) thus resulting in a library size of 4×107 independent clones. After one hour of phenotype expression, positive transformants were selected for carbenicilline resistance encoded by the pComb vector. After this adaption these clones were infected with an infectious dose of 1×10$^{12}$ phage particles of the helper phage VCSM13 resulting in the production and secretion of filamentous M13 phages, each of them containing single stranded pComb3H-DNA encoding a single human light chain and the Fd segment of chimeric M79 and displaying the corresponding Fab fragment on the phage surface as a translational fusion to the non-infectious part of phage coat protein III (phage display), see FIG. 2.

This phage library carrying the cloned Fab repertoire was harvested from the culture supernatant by PEG8000/NaCl precipitation and centrifugation, redissolved in TBS/1% BSA and incubated with recombinant s17-1A immobilized on 96 well ELISA plates. s17-1A was prepared as described (Mack, Proc. Natl. Sci. U.S.A. 92 (1995) 7021-7025). Fab phages that did not specifically bind to the target antigen were eliminated by up to ten washing steps with TBS/0.5% Tween. Binders were eluted by using HCl-Glycine pH 2.2 and after neutralization of the eluat with 2 M Tris pH 12, used for infection of a new uninfected *E. coli* XL1 Blue culture. Cells successfully transduced with a pComb phagmid copy, encoding an antigen binding Fab fragment, were again selected for carbenicilline resistance and subsequently infected with VCSM13 helper phage to start the second round of antibody display and in vitro selection.

After five rounds of production and selection of antigen-binding Fab phages, plasmid DNA containing the selected Fab repertoire was prepared.

For the production of soluble Fab proteins the gene III DNA fragment was excised from the plasmids thus destroying the translational fusion of the Fd heavy chain segment with the gene III protein. After religation, this pool of plasmid DNA was transformed into 100 μl heat shock competent *E. coli* XL1 Blue and plated on Carbenicilline (Garb) LB-Agar. Single colonies were grown in 10 ml LB-Carb-cultures/20 nM M9Cl$_2$ and Fab expression was induced after six hours by adding Isopropyl-(3-D-thiogalactosid (IPTG) to a final concentration of 1 mM. This in vitro selection as well as expression of soluble Fab-fragments was carried out according to Burton, Proc. Natl. Acad. Sci. U.S.A. 88 (1991), 10134-10137. The cells were harvested after 20 hours; periplasma preparation was carried out by four rounds of freezing (ethanol/dry ice) and thawing (37° C.) and tested by ELISA for Fab fragments binding to s17-1A. 23 of 27 clones showed binding activity. After sequencing, the two clones with the strongest signals (see FIG. 3) turned out to have identical kappa chains and were called k8; see FIG. 6.

This human kappa light chain k8 was now used as a binding partner for the human Ig delta heavy chain pool; 2250 ng of human delta heavy chain Fd DNA-fragments (digested with XhoI and SpeI) were ligated with 7000 ng of the phagmid vector pComb3H (digested with XhoI and SpeI; large DNA-fragment) containing the k8 DNA-fragment in the light chain position.

The choice of the human delta chain repertoire as source for heavy chain variable-regions that specifically bind to the 17-1A antigen, when combined with the k8 light chain, appeared to be most suitable. Delta chains are only produced in mature unprimed and in self-antigen specific anergic B-cells that have not yet or will not undergo proliferation; therefore the diversity of their heavy chain repertoire is higher and the number of each single specificity therein is lower compared to heavy chain repertoires of other immunoglobulin isotypes.

The transformation of the pComb-k8-delta Fd-fragment library into a total of 1500 pd *E. coli* XL1 Blue by five equal electroporations (2.5 kV, 0.2 cm gap cuvette, 25 FD, 200 Ohm) resulted in a final number of 1.1×10$^9$ independent clones. In vitro selection of this combinatorial antibody library was carried out as described above for the human light chain repertoire. After four rounds of panning soluble Fab fragments were prepared from eight clones.

The periplasma preparations were tested on ELISA. One of the clones showed strong antigen binding (see FIG. 4). This clone was called D4.5 and the DNA of the Fd delta fragment was sequenced with a reverse delta CHI-specific primer (see FIG. 7).

Another s17-1A binding Fab fragment was isolated after further rounds of panning first appearing in round seven with a markedly weaker ELISA signal compared to D4.5 (see FIG. 4). The clone was designated as D7.2 and the DNA sequence was determined again using the delta specific primer (see FIG. 8).

To identify further light chain partners that combine with the D4.5 delta heavy chain Fd segment to form a 17-1A specific Fab-fragment, a reshuffling experiment was carried out:

450 ng of human kappa light chain fragments and 450 ng of human lambda light chain fragments (both digested with SacI and XbaI) were each ligated with 1400 ng of the phagmid pComb3H (digested with SacI and XbaI; large DNA-fragment) wherein the heavy chain position was already occupied by the D4.5 Fd fragment. The resulting combinatorial antibody libraries (kappa and lambda) were then each transformed into 300 μl of electrocompetent *Escherichia coli* XLI Blue by electroporation (2.5 kV, 0.2 cm gap cuvette, 25 FD, 200 Ohm, Biorad gene-pulser) thus resulting in a library size of 0.5×107 independent clones for the kappa library and of 1.4×107 independent clones for the lambda library. After one hour of phenotype expression, positive transformants were selected for carbenicilline resistance encoded by the pComb vector. After this adaption these clones were infected with an infectious dose of 1×1012 phage particles of the helper phage VCSM13 resulting in the production and secretion of filamentous M13 phages, each of them containing single stranded pComb3H-DNA encoding a single human light chain and the D4.5 heavy chain Fd segment and displaying the corresponding Fab fragment on the phage surface as a translational fusion to the non-infectious part of phage coat protein III.

Both phage libraries carrying the cloned Fab repertoires (kappa and lambda) were harvested from the culture supernatant by PEG8000/NaCl precipitation and centrifugation, redissolved in TBS/1% BSA and incubated with recombinant s17-IA immobilized on 96 well ELISA plates. Fab phages that did not specifically bind to the target antigen were eliminated by up to ten washing steps with TBS/0.5% Tween. Binders of both libraries (kappa and lambda) were eluted by using HCl-Glycine pH 2.2 and after neutralization of the eluat with 2 M Tris pH 12, used for infection of new uninfected *E. coli* XL1 Blue cultures, one for the kappa and one for the lambda library. Cells successfully transduced with a pComb phagmid copy, encoding an antigen binding Fab fragment, were again selected for carbenicilline resistance and subsequently infected with VCSM13 helper phage to start the second round of antibody display and in vitro selection.

After five rounds of production and selection of antigen-binding Fab phages, preparations of plasmid DNA were carried out containing the selected Fab repertoire of each round of panning, respectively.

For the production of soluble Fab proteins the gene III DNA fragment was excised from the plasmids thus destroying the translational fusion of the I'd heavy chain segment with the gene III protein. After religation, this pool of plasmid DNA was transformed into 100 µl heat shock competent *E. coli* XL1 Blue and plated on Carbenicilline (Carb) LB-Agar. Single colonies were grown in 10 ml LB-Carb-cultures/20 MM $MgCl_2$ and Fab expression was induced after six hours by adding Isopropyl-R-D-thiogalactosid (IPTG) to a final concentration of 1 mM. The cells were harvested after 20 hours; periplasma preparation was carried out by freezing and thawing and tested by ELISA for Fab fragments binding to s17-1A.

In total, 45 clones of the kappa and 45 clones of the lambda library derived predominantly from the fifth round of panning but to a minor extend also from other rounds were tested for binding to the 17-1A antigen. Only one clone designated k5.1 (kappa library) that appeared in round Five showed binding activity (see FIG. 5). The DNA-sequence of the Kappa V-region of k5.1 was determined (see FIG. 9).

EXAMPLE II

Bacterial Expression in *E. coli* XL1 Blue

As previously mentioned in example I, *E. coli* X11 Blue transformed with pComb3H containing one light and the Fd-segment of one heavy chain produce soluble Fab in sufficient amounts after excision of the gene III fragment and induction with IPTG. The heavy chain Fd-segment and the light chain are exported into the periplasma where they assemble and form functional Fab-fragments.

For better periplasma preparations the cells were grown in SB-medium supplemented with 20 mM $MgCl_2$ and are redissolved in PBS after harvesting. By four rounds of freezing at −70° C. and thawing at 37° C., the outer membrane of the bacteria was destroyed by temperature shock and the soluble periplasmatic proteins including the Fab fragments were released into the supernatant. After elimination of intact cells and cell-debris by centrifugation, the supernatants containing the Fab-antibody-fragments were collected and used for further examination.

First, k8-D4.5-Fab and k5.1-D4.5-Fab periplasma preparations were tested for binding to immobilized s17-1A antigen, both showing strong ELISA signals (see example I).

Detection of k8-D4.5 and k5.1-D4.5-Fab-fragments bound to immobilized s17-1A antigen was carried out using a polyclonal biotinylated anti-human-kappa light chain antibody (1 µg/ml PBS) detected with horse raddish conjugated Avidine (1 µg/ml PBS). The signal was developed by adding a substrate solution, containing 2,2' Azino-bis(3-Ethylbenz-Thiazoline-6-Sulfonic Acid) and Na-perborate and detected at a wavelength of 405 nm.

The test for binding of the two 17-1A positive human Fab-fragments (k8-D4.5-Fab and k5.1-D4.5-Fab) on Kato-cells (17-1A expressing gastric cancer cell-line), 17-1A transfected CHO-cells (CHO/17-1A) and non-transfected CHO-cells was again carried out with the periplasma preparations. CHO transfected cell-lines were generated by subcloning of a DNA-fragment encoding the complete amino acid sequence of the 17-1A-antigen also known as GA733-2 (Szala, Proc. Natl. Acad. Sci. U.S.A. 87 (1990), 3542-3546), into the eucaryotic expression vector pEF-DHFR (Mack, Proc. Natl. Acad. Sci. U.S.A. 92 (1995) 7021-7025) according to standard procedures (Sambrook, Molecular Cloning; A Laboratory Manual, Second Edition, Cold Spring Harbour Laboratory Press, Cold Spring Harbour, N.Y. (1989)). The resulting plasmid was linearized with NdeI and transfected into DHFR-deficient CHO-cells for stable expression. The expression of transmembrane 17-1A was increased by stepwise gene amplification induced by subsequent addition of increasing concentrations of the DHFR-inhibitor Methotrexat (MTX) to a final concentration of 500 nM, with the concentration steps in between being 20 nM and 100 nM (Kaufinann, Methods Enzymol. 185 (1990), 537-566).

200 000 cells (Kato-, CHO/17-1A- or CHO-cells) were incubated with one of the periplasma preparations containing relevant or irrelevant Fab, followed by biotinylated polyclonale anti-human-kappa light chain antibody (20 µg/ml PBS) and FITC-conjugated Streptavidine. Labeled cells were then analyzed by flow cytometry. The periplasma preparations containing the k8-D4.5-Fab and the k5.1-D4.5-Fab, respectively showed distinct signals compared to irrelevant periplasma preparation (negative control), but no staining of untransfected CHO-cells thus demonstrating specificity for the 17-1A-antigen. The anti 17-1A antibody M79 (Gottlinger, Int. J. Cancer 38 (1986), 47-53) was used as a positive control for 17-1A-positive cells and a murine IgG2a antibody as isotype control (see FIG. 10 and FIG. 11).

EXAMPLE III

Eucaryotic Expression in CHO-cells

Bacteria are usually not capable of producing complete functional immunoglobulins although they express functional Fab fragments.

For the production of complete functional antibodies, mammalian cells have to be used and therefore the k8-light chain and the variable domain of D4.5 heavy chain were subcloned into mammalian expression vectors.

a.) light chains (k8 and k5.1): To generate suitable terminal restriction sites, the k8 and the k5.1 DNA fragments were reamplified by PCR, resulting in kappa fragments with a Bsu36I-site at the 5'-end as well as a SalI and a NotI-site at the 3'-end.

These fragments (k8 and k5.1) were subcloned into the plasmid BSPOLL by Bsu36I and Not I, thus adding a mammalian leader sequence and sequenced for preventing PCR-induced mutations.

Utilizing EcoRI and SalI, k8 and k5.1 were excised from BSPOLL and subcloned into the eucaryotic expression vector pEF-ADA (see FIG. 12) derived from the expression vector pEF-DHFR (Mack, Proc. Natl. Acad. Sci. U.S.A. 92 (1995) 7021 7025) by replacing the cDNA encoding murine dihydrofolate reductase (DHFR) by that encoding murine adenosine deaminase (ADA).

For each light chain species (k8 and k5.1), 107 CHO cells were transfected with 100 µg of linearized plasmid DNA, respectively and subsequently cultured under conditions selecting for adenosine desaminase (ADA) activity encoded by the expression vector.

Surviving ADA-positive cells were cultured for further transfection with heavy chains carrying the D4.5- or the D7.2-variable domain.

b.) heavy 4.5 variable domain: From the delta Fd-fragment D4.5, the variable region was reamplified by PCR generating Bsu36I restriction sites at both ends.

The resulting V-D4.5 DNA-fragment was then subcloned by using these restriction sites, into the eucaryotic expression vector pEF-DHFR already containing an eucaryotic leader sequence as well as a DNA-fragment encoding the human IgG1 heavy chain constant region (see FIG. 13). The D4.5 heavy chain variable region was thus inserted between the leader and the heavy chain constant region.

The variable region was sequenced and the complete clone was designated H79V-D4.5 hu IgG1.

For later tissue staining, the human IgG1 heavy chain constant region was replaced by the murine IgG1 heavy chain constant region using XbaI for subcloning. This plasmid was designated H79V-D4.5 MIgG1.

Both, the human and the murine IgG1-version of the D4.5 heavy chain were each transfected into 107 CHO-cells, already expressing the k8 light chain, respectively. The human IgG1-version was also transfected into CHO cells expressing the k5.1 light chain. 100 μg linearized plasmid DNA was used for heavy chain transfection, respectively.

The variable region of the D7.2 heavy chain Fd-fragment was also subcloned into pEF-DHFR resulting in a human IgG1 heavy chain expressing plasmid as described for VD4.5. This expression plasmid was then transfected into CHO-cells already expressing the k8 light chain as described above for H79V-D4.5 hu IgG1.

The transfected cells were subjected to selection for ADA- and DHFR-activity as described (Kaufman, Methods Enzymol. 185 (1990), 537-566).

The resulting cell lines were designated H79-huIgG1 (VD4.5huIgG1-k8), H79-MIgG1 (VD4.5MIgG1-k8), D7.2 (VD7.2huIgG1-k8) and HD70 (VD4.5huIgG1-k5.1).

Three days old culture supernatants from four different confluent 30 ml cell-cultures each producing one of the four anti-17-1A-antibodies (H79-huIgG1, H79-MIgG1, D7.2 and HD70) were tested by ELISA for binding to immobilized s17-1A. Except for D7.2 showing a weak ELISA-signal, the three other antibodies showed strong signals, estimated to represent a binding affinity in the range of the murine antibody M79.

Large scale antibody production was carried out in roller bottles using 500 ml medium.

The antibodies H79-huIgG1, D7.2 and HD70 were purified by using a protein A affinity column. The H79-MIgG1 antibody was purified by anti-mouse IgG affinity chromatography.

Purity and molecular weight of the recombinant antibodies were determined by SDS-PAGE under reducing and nonreducing conditions (FIG. 14 and FIG. 15). Protein purification and SDS-PAGE were carried out according to standard procedures.

EXAMPLE IV

Functional Analysis of the H79 Antibodies and HD70

IV. 1. Test on Immobilized Antigen

Three days old culture supernatant of a confluent 30 ml culture of human and murine IgG1-transfectants respectively as well as the corresponding preparations of purified antibody were tested for binding on immobilized s17-1A antigen by ELISA and compared to the murine M79 anti 17-1A antibody.

Detection was carried out as described in 11.

The antibodies H79 (huIgG1- and MIgG1 version) and HD70 were estimated to have very similar binding affinities in the range of the murine M79.

IV.2. Determination of Affinities

Surface plasmon resonance measurement was performed using the BIACORE 2000 device (Biacore AB, Freiburg, Freiburg, Germany). Immobilization of recombinant soluble 17-1A-antigen in each flow cell and analysis of the interaction was carried out with an automatic method in BIACORE 2000. The antigen was covalently coupled to sensor chip CM5 via primary amine groups. After activation of the carboxylated dextran matrix of CM5 sensor chip with a single injection of 80111 of 0.1 M N-hydroxisuccinimide/0.4 M N-ethyl-N'-(3-dimethylaminopropyl)-carbodiimide (NHS/EDC9) through all four flow cells, flow cells 1,2,3 and 4 were successively included into the flow path during injection of s17-1A-antigen (60 μg/ml in 10 mM sodium acetate, pH 4.7). Different contact times of 17-1A to the activated surface lead to approximately 2500 response units (RU9 in flow cell 1, 14000 RU in flow cell 2, 780 RU in flow cell 3 and 290 RU in flow cell 4). Excess activated esters were blocked by injection of 85 μl 1 M ethanolamine pH 5 over all four flow cells. Binding experiments were performed at 25° C. in buffer of pH 7.4 containing 10 mM Hepes, 150 mM NaCl, 3 mM EDTA and 0.005% surfactant P20. The binding kinetics of antibodies to immobilized recombinant 17-1A were determined by injecting antibody concentrations ranging from 0.5 to 2 11M. The sensor chip was regenerated between each run with 100 mM Glycin, 500 mM NaCl, 0.005% Tween pH3. The association and dissociation rate constants, Kon and Koff were analysed using BIA-evaluation software from Biacore AB as described (Karlsson, (1991) J Immunol Meth 145: 229-240).

Two sets of affinity determinations were carried out (1. set: M79, H79, D7.2, Panorex; 2. set: Panorex, HD70); the murine Panorex was also included in set 2 as internal reference.

The KD of D7.2 proved to be below the minimal detection value of 10-4 M and is therefore not shown in Tab 2.

TABLE. 2

KD, Kon and Koff-rates of human and relevant murine 17-1A antibodies

| Antibody | Kon (M − 1 s − 1) | Koff (s − 1) | KD (M) |
|---|---|---|---|
| 1. set: | | | |
| murine M79 | 6.0 × 104 | 4.5 × 10 − 2 | 7.5 × 10 − 7 |
| human H79 | 2.1 × 104 | 7.2 × 10 − 3 | 3.4 × 10 − 7 |
| murine Panorex | 1.1 × 105 | 2.2 × 10 − 2 | 2.0 × 10 − 7 |
| 2. set: | | | |
| human HD70 | 0.9 × 105 | 3.5 × 10 − 2 | 3.9 × 10 − 7 |
| murine Panorex | 1.0 × 105 | 2.7 × 10 − 2 | 2.7v10 − 7 |

IV.3. Flow Cytometry on 17-1A Expressing Eucaryotic Cells

Purified antibody preparations of H79 (human and murine IgG1 version), HD70 (human IgG1) and D7.2 (human IgG1) were tested by FACS analysis on 17-1A expressing Kato cells, 17-1A-transfected CHO-cells and untransfected CHO-cells. 2×105 cells were incubated with purified H79-huIgG1, H79-MIgG1, HD70, D7.2, M79, Panorex, M74ch (=human CHIgG1-human Ckappa-version of the murine anti-17-1A-antibody M74 (Gottlinger, Int. J. Cancer 38 (1986), 47-53)), murine IgG2a, murine IgG1, or human IgG1 (20 μg/ml antibody each), respectively. Detection of cell-bound antibodies was carried out with FITC labeled anti mouse IgG- or anti human IgG antibodies (20 μg/ml each). Incubation was carved out for 45-60 min. on ice.

H79 human IgG1, H79 murine IgG1 and HD70 showed distinct binding to the 17-1A positive cells as well as M79 and Panorex. D7.2 showed weak but significant binding to 17-1A positive cells. None of the antibodies showed binding to untransfected CHO cells and IgG-controls were negative on Kato-cells, CHO/17-1A-cells and untransfected CHO cells (see FIG. 16 and FIG. 17).

IVA. Antibody Dependent Cellular Cytotoxicity (51Cr Release)

For 51 Cr release, human peripheral blood mononuclear cells (PBMCs) as effector cells were isolated from the fresh buffy coat of healthy donors. The PBMCs were separated by Ficoll density gradient centrifugation with a subsequent 100×g centrifugation step. Unstimulated PBMCs (5×105 cells) were added in a volume of 100 ml of RPMI 1640 medium with 10% FCS to each well of a flat bottomed microtiter plate and incubated overnight at 37° C. Target cells were labelled for 2 h with 51Cr. Labeled target cells (100 μl) and antibodies in different concentrations (50 μl) were added to the PBMCs and incubated for 18 h at 37° C. Corresponding non-binding isotypes were used as negative controls. Specific lysis was calculated as ((cpm, experimental release)−(cpm, spontaneous release))/((cpm, maximal release)−(cpm, spontaneous release)).

The human anti 17-1A antibodies H79 and HD70 proved to mediate high cytotoxicity for the 17-1A positive gastric cancer cell line KATO in this 51Cr release assay. The murine anti 17-1A antibodies M79 and Panorex proved to mediate cell killing to a distinctly lower level (FIG. 18).

IV.5. Test on Human Tissue 5 nm cryosections of a colon carcinoma and normal colon tissue respectively were incubated with the murine IgG-version of the antibody H79 (10 μg/ml). In this experiment the murine IgG1 version of H79 was used to avoid unspecific staining due to the presence of human immunoglobulin in human tissue. Detection of bound H79MIgG1 was carried out with a peroxidase conjugated polyclonal anti mouse Ig antibody and stained with carbazole. Counter staining was carried out with hemalaun.

Results were evaluated by light microscopy.

H79MIgG1 as well as the murine monoclonal antibody M79 (positive control) showed strong staining on normal colon mucosa (M79, FIG. 19; H79-MIgG1, FIG. 20) and weaker staining on colon carcinoma cells (M79, FIG. 21; H79-MIgG1, FIG. 22). In contrast, Isotype controls showed no staining on colon mucosa and colon carcinoma tissues (for M79; FIGS. 23 and 25 and for H79-MIgG1, FIG. 24 and FIG. 26).

EXAMPLE V

Epitope Analysis of H79 and HD70

To compare the 17-1A-epitopes recognized by the human antibodies H79 and HD70, and by the murine template antibody M79, 13 mer peptides derived from the amino acid sequence of the extracellular part of the 17-1A-antigen were synthesized as single spots on a Pep Spots Membrane. These peptides cover the whole extracellular amino acid sequence of the 17-1 A-antigen (as defined by Szala, Proc. Natl. Acad. Sci. U.S.A. 87 (1990), 3542-3546) by having an overlap of 11 amino acids with each of the neighboring peptides with the first amino acid of peptide 1 being identical with the N-terminal amino acid of the 17-1A antigen and the last amino acid of peptide 119 being identical with the C-terminal amino acid of the extracellular part of the 17-1A-antigen (Tab. 3).

TABLE 3

Synthesized peptides (numbers correspond to the numbers of peptide spots)

| | SEQ ID NO: | | SEQ ID NO: |
|---|---|---|---|
| TATFAAAQEECVC | 22 | TFAAAQEECVCEN | 23 |
| AAAQEECVCENYK | 24 | AQEECVCENYKLA | 25 |
| EECVCENYKLAVN | 26 | CVCENYKLAVNCF | 27 |
| CENYKLAVNCFVN | 28 | NYKLAVNCGVNNN | 29 |
| KLAVNCFVNNNRQ | 30 | AVNCFVNNNRQCQ | 31 |
| NCFVNNNRQCQCT | 32 | FVNNNRQCQCTSV | 33 |
| NNNRQCQCTSVGA | 34 | NRQCQCTSVGAQN | 35 |
| QCQCTSVGAQNTV | 36 | QCTSVGAQNTVIC | 37 |
| TSVGAQNTVICSK | 38 | VGAQNTVICSKLA | 39 |
| AQNTVICSKLAAK | 40 | NTVICSKLAAKCL | 41 |
| VICSKLAAKCLVM | 42 | CSKLAAKCLVMKA | 43 |
| KLAAKCLVMKAEM | 44 | AAKCLVMKAEMNG | 45 |
| CKLVMKAEMNGSK | 46 | LVMKAEMNGSKLG | 47 |
| MKAEMNGSKLGRR | 48 | AEMNGSKLGRRAK | 49 |
| MNGSKLGRRAKPE | 50 | GSKLGRRAKPEGA | 51 |
| KLGRRAKPEGALQ | 52 | GRRAKPEGALQNN | 53 |
| RAKPEGALQNNDG | 54 | KPEGALQNNDGLY | 55 |
| EGALQNNDGLYDP | 56 | ALQNNDGLYDPDC | 57 |
| QNNDGLYDPDCDE | 58 | NPGLYDPDCDESG | 59 |
| GLYDPDCDESGLF | 60 | YDPDCDESGLFKA | 61 |
| PDCDESGLFKAKQ | 62 | CDESGLFKAKQCN | 63 |
| ESGLFKAKQCNGT | 64 | GLFKAKQCNGTST | 65 |
| FKAKQCNGTSTCW | 66 | AKQCNGTSTCWCV | 67 |
| QCNGTSTCWCVNT | 68 | NGTSTCWCVNTAG | 69 |
| TSTCWCVNTAGVR | 70 | TCWCVNTAGVRRT | 71 |
| WCVNTAGVRRTDK | 72 | VNTAGVRRTDKDT | 73 |
| TAGVRRTDKDTEI | 74 | GVRRTDKDTEITC | 75 |
| RRTDKDTEITCSE | 76 | TDKDTEITCSERV | 77 |
| KDTEITCSERVRT | 78 | TEITCSERVRTYW | 79 |
| ITCSERVRTYWII | 80 | CSERVRTYWIIIE | 81 |
| ERVRTYWIIIELK | 82 | VRTYWIIIELKHK | 83 |
| TYWIIIELKHKAR | 84 | WIIIELKHKAREK | 85 |
| IIELKHKAREKPY | 86 | ELKHKAREKPYDS | 87 |
| KHKAREKPYDSKS | 88 | KAREKPYDSKSLR | 89 |
| REKPYDSKSLRTA | 90 | KPYDSKSLRTALQ | 91 |

TABLE 3-continued

Synthesized peptides (numbers correspond to the numbers of peptide spots)

| | SEQ ID NO: | | SEQ ID NO: |
|---|---|---|---|
| YDSKSLRTALQKE | 92 | SKSLRTALQKEIT | 93 |
| SLRTALQKEITTR | 94 | RTALQKEITTRYQ | 95 |
| ALQKEITTRYQLD | 96 | QKEITTRYQLDPK | 97 |
| EITTRYQLDPKFI | 98 | TTRYQLDPKFITS | 99 |
| RYQLDPKFITSIL | 100 | QLDPKFITSILYE | 101 |
| DPKFITSILYENN | 102 | KFITSILYENNVI | 103 |
| ITSILYENNVITI | 104 | SILYENNVITIDL | 105 |
| LYENNVITIDLVQ | 106 | ENNVITIDLVQNS | 107 |
| NVITIDLVQNSSQ | 108 | ITIDLVQNSSQKT | 109 |
| IDLVQNSSQKTQN | 110 | LVQNSSQKTQNDV | 111 |
| QNSSQKTQNDVDI | 112 | SSQKTQNDVDIAD | 113 |
| QKTQNDVDIADVA | 114 | TQNDVDIADVAYY | 115 |
| NDVDIADVAYYFE | 116 | VDIADVAYYFEKD | 117 |
| IADVAYYFEKDVK | 118 | DVAYYFEKDVKGE | 119 |
| AYYFEKDVKGESL | 120 | YFEKDVKGESLFH | 121 |
| EKDVKGESLFHSK | 122 | DVKGESLFHSKKM | 123 |
| KGESLFHSKKMDL | 124 | ESLFHSKKMDLTV | 125 |
| LFHSKKMDLTVNG | 126 | HSKKMDLTVNGEQ | 127 |
| KKMDLTVNGEQLD | 128 | MDLTVNGEQLDLD | 129 |
| LTVNGEQLDLDPG | 130 | VNGEQLDLDPGQT | 131 |
| GEQLDLDPGQTLI | 132 | QLDLDPGQTLIYY | 133 |
| DLDPGQTLIYYVD | 134 | DPGQTLIYYVDEK | 135 |
| GQTLIYYVDEKAP | 136 | TLIYYVDEKAPEF | 137 |
| IYYVDEKAPEFSM | 138 | YVDEKAPEFSMQG | 139 |
| DEKAPEFSMQGLK | 140 | | |

The PepSpots Membrane with the synthesized peptides was shaken for ten minutes in methanol and then washed three times for ten minutes in TBS-buffer pH8. The membrane was then blocked in casein based blocking solution, containing 0.05 g/ml sucrose for one hour and then once shaken in TBS pH8/0.05% Tween 20 (TBS-T).

Each of the anti-17-1A antibodies was incubated at room temperature together with the membrane for three hours in blocking solution (1 μg antibody/ml). After three washes in TBS-T for ten minutes each, the horse radish peroxidase (HRP) conjugated secondary antibody (anti mouse/anti human; 1 μg/ml blocking solution) was incubated for two hours at room temperature together with the membrane. Then the membrane was washed for three times in TBS-T for ten minutes each. Detection of bound antibodies was performed directly on the Pep Spots Membrane in case of M79 according to the protocol of the chemoluminescence kit manufacturer (Boehringer). The developed films are shown in FIG. 27. The blot was regenerated after three washes with TBS-T (10 min.) in a solution containing 50 mM Tris-HCl pH 6.7, 100 mM 2-Mercaptoethanol and 2% (w/v) SDS for 30 min at 50° C. and subsequently reused for epitope mapping of the next antibody.

Due to the higher degree of unspecific binding of the anti-human immunoglobulin secondary antibody to the polypeptide-spots on the membrane, a fractionated electrotransfer to a second blotting-membrane followed by detection with the antihuman secondary antibody was carried out in case of HD70 and H79 according to Rudiger, EMBO 16 (1997) 1501-1507. Incubation with the secondary antibody and antibody detection on the blots was performed as described above. The developed films are presented in FIG. 27.

As shown in this figure (FIG. 27), the results of peptide based epitope mapping indicate, that the epitope recognized by the murine template antibody M79, mainly represented by peptide spots 38 and 95, profoundly differs from that recognized by the human antibody H79, mainly represented by peptide spots 8, 11, 13, 14, 59-60, 77 and 79. As the human antibody HD70 shows no detectable binding at all, it can 44 be further anticipated, that its epitope also differs from that of the murine antibody M79 and that the epitopes of the human antibodies H79 and HD70 are not identical, too.

The absence of detectable binding signals in case of the human antibody HD70 may be explained by its possible recognition either of a conformational, continuous or discontinuous epitope or of an epitope partially or entirely consisting of carbohydrate; in either case mimicking of such epitopes by short peptides can hardly be expected.

The invention claimed is:

1. An antibody or antibody fragment being low or not immunogenic in humans and recognizing the human 17-1A antigen as expressed on the surface of tumor cells, the antibody or antibody fragment comprising a human VH chain and a human VL chain, wherein at least said VH chain comprises three CDRs being encoded by nucleotides 91 to 105, 148 to 198 and 292 to 351 of SEQ ID NO: 143, and said VL chain comprises three CDRs encoded by nucleotides 70 to 102, 148 to 168 and 265 to 294 of SEQ ID NO: 147.

2. The antibody or antibody fragment according to claim 1, which is an antibody fragment.

3. An antibody or antibody fragment comprising a human VH chain and a human VL chain, said antibody or antibody fragment recognizing the human 17-1A antigen as expressed on the surface of tumor cells, wherein at least said VH chain comprises three CDRs being encoded by nucleotides 91 to 105, 148 to 198 and 292 to 351 of SEQ ID NO: 143, and said VL chain comprises three CDRs encoded by nucleotides 70 to 102, 148 to 168 and 265 to 294 of SEQ ID NO: 147.

4. The antibody or antibody fragment according to claim 3, said antibody or antibody fragment being low or not immunogenic in humans.

5. The antibody or antibody fragment according claim 3, recognizing an epitope of the extracellular domain of the 17-1A antigen.

6. The antibody or antibody fragment according to claim 1, further comprising, fused to said human VH and VL chains, immunoglobulin constant regions of heavy (CH) and light chains (CL), respectively, or non-immunoglobulin chains.

7. The antibody or antibody fragment according to claim 6, wherein said constant region chains are from human IgG1 or IgG3.

8. The antibody or antibody fragment according to claim 1, further comprising a radioisotope, a chemotherapeutic agent or a toxin linked to said human VH and VL chains.

9. The antibody or antibody fragment according to claim 1, dispersed in a pharmaceutically acceptable carrier.

10. The antibody or antibody fragment according to claim 3, dispersed in a pharmaceutically acceptable carrier.

* * * * *

SEQUENCE LISTING

<160> NUMBER OF SEQ ID NOS: 169

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: Synthetic Primer

<400> SEQUENCE: 1
aggtgcagct gctcgagtct gg                                              22

```
<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 2
cagagtcacc ttgctcgagt ctgg                                            24

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 3
caggtgcagc tgctcgagtc ggg                                             23

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 4
caggtgcagc tactcgagtg ggg                                             23

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 5
caggtacagc tgctcgagtc agg                                             23

<210> SEQ ID NO 6
<211> LENGTH: 29
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 6
tgccttactg tctctggcca gcggaagat                                       29

<210> SEQ ID NO 7
<211> LENGTH: 38
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 7
gagccgcacg agcccgagct ccagatgacc cagtctcc                             38
```

```
<210> SEQ ID NO 8
<211> LENGTH: 40
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 8
gagccgcacg agcccgagct cgtgattgac agcagtctcc                           40

<210> SEQ ID NO 9
<211> LENGTH: 39
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 9
gagccgcacg agcccgagct cgtgatgacc tcagtctcc                            39

<210> SEQ ID NO 10
<211> LENGTH: 38
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 10
gagccgcacg agcccgagct cacactcacg cagtctcc                             38

<210> SEQ ID NO 11
<211> LENGTH: 38
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 11
gagccgcacg agcccgagct cgtgctgact cagtctcc                             38

<210> SEQ ID NO 12
<211> LENGTH: 58
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 12
gcgccgtcta gaattaacac tctcccctgt tgaagctctt tgtgacgggc gaactcag       58

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 13
aattttgagc tcactcagcc ccac                                            24
```

<210> SEQ ID NO 14
<211> LENGTH: 27
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 14
tctgccgagc tccagcctgc ctccgtg                                          27

<210> SEQ ID NO 15
<211> LENGTH: 27
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 15
tctgtggagc tccagccgcc ctcagtg                                          27

<210> SEQ ID NO 16
<211> LENGTH: 33
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 16
tctgaagagc tccaggaccc tgttgtgtct gtg                                   33

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 17
cagtctgagc tcacgcagcc gccc                                             24

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 18
cagactgagc tcactcagga gccc                                             24

<210> SEQ ID NO 19
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 19
caggttgagc tcactcaacc gccc                                             24

<210> SEQ ID NO 20

```
<211> LENGTH: 27
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 20
caggctgagc tcactcagcc gtcttcc                                        27

<210> SEQ ID NO 21
<211> LENGTH: 30
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 21
cgccgtctag aattatgaac attctgtagg                                     30

<210> SEQ ID NO 22
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 22

Thr Ala Thr Phe Ala Ala Ala Gln Glu Glu Cys Val Cys
1               5                   10

<210> SEQ ID NO 23
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 23

Thr Phe Ala Ala Ala Gln Glu Glu Cys Val Cys Glu Asn
1               5                   10

<210> SEQ ID NO 24
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 24

Ala Ala Ala Gln Glu Glu Cys Val Cys Glu Asn Tyr Lys
1               5                   10

<210> SEQ ID NO 25
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 25

Ala Gln Glu Glu Cys Val Cys Glu Asn Tyr Lys Leu Ala
1               5                   10
```

```
<210> SEQ ID NO 26
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 26

Glu Glu Cys Val Cys Glu Asn Tyr Lys Leu Ala Val Asn
1               5                   10

<210> SEQ ID NO 27
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 27

Cys Val Cys Glu Asn Tyr Lys Leu Ala Val Asn Cys Phe
1               5                   10

<210> SEQ ID NO 28
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 28

Cys Glu Asn Tyr Lys Leu Ala Val Asn Cys Phe Val Asn
1               5                   10

<210> SEQ ID NO 29
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 29

Asn Tyr Lys Leu Ala Val Asn Cys Phe Val Asn Asn Asn
1               5                   10

<210> SEQ ID NO 30
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 30

Lys Leu Ala Val Asn Cys Phe Val Asn Asn Asn Arg Gln
1               5                   10

<210> SEQ ID NO 31
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide
```

<400> SEQUENCE: 31

Ala Val Asn Cys Phe Val Asn Asn Arg Gln Cys Gln
1               5                   10

<210> SEQ ID NO 32
<211> LENGTH: 13
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 32

Asn Cys Phe Val Asn Asn Arg Gln Cys Gln Cys Thr
1               5                   10

<210> SEQ ID NO 33
<211> LENGTH: 13
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 33

Phe Val Asn Asn Asn Arg Gln Cys Gln Cys Thr Ser Val
1               5                   10

<210> SEQ ID NO 34
<211> LENGTH: 13
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 34

Asn Asn Asn Arg Gln Cys Gln Cys Thr Ser Val Gly Ala
1               5                   10

<210> SEQ ID NO 35
<211> LENGTH: 13
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 35

Asn Arg Gln Cys Gln Cys Thr Ser Val Gly Ala Gln Asn
1               5                   10

<210> SEQ ID NO 36
<211> LENGTH: 13
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 36

Gln Cys Gln Cys Thr Ser Val Gly Ala Gln Asn Thr Val
1               5                   10

<210> SEQ ID NO 37
<211> LENGTH: 13

```
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 37

Gln Cys Thr Ser Val Gly Ala Gln Asn Thr Val Ile Cys
1               5                   10

<210> SEQ ID NO 38
<211> LENGTH: 13
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 38

Thr Ser Val Gly Ala Gln Asn Thr Val Ile Cys Ser Lys
1               5                   10

<210> SEQ ID NO 39
<211> LENGTH: 13
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 39

Val Gly Ala Gln Asn Thr Val Ile Cys Ser Lys Leu Ala
1               5                   10

<210> SEQ ID NO 40
<211> LENGTH: 13
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 40

Ala Gln Asn Thr Val Ile Cys Ser Lys Leu Ala Ala Lys
1               5                   10

<210> SEQ ID NO 41
<211> LENGTH: 13
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 41

Asn Thr Val Ile Cys Ser Lys Leu Ala Ala Lys Cys Leu
1               5                   10

<210> SEQ ID NO 42
<211> LENGTH: 13
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 42

Val Ile Cys Ser Lys Leu Ala Ala Lys Cys Leu Val Met
```

<210> SEQ ID NO 43
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 43

Cys Ser Lys Leu Ala Ala Lys Cys Leu Val Met Lys Ala
1               5                   10

<210> SEQ ID NO 44
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 44

Lys Leu Ala Ala Lys Cys Leu Val Met Lys Ala Glu Met
1               5                   10

<210> SEQ ID NO 45
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 45

Ala Ala Lys Cys Leu Val Met Lys Ala Glu Asn Gly
1               5                   10

<210> SEQ ID NO 46
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 46

Lys Cys Leu Val Met Lys Ala Glu Met Asn Gly Ser Lys
1               5                   10

<210> SEQ ID NO 47
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 47

Leu Val Met Lys Ala Glu Met Asn Gly Ser Lys Leu Gly
1               5                   10

<210> SEQ ID NO 48
<211> LENGTH: 13
<212> TYPE: PRT
<213> ORGANISM: Artificial Sequence
<220> FEATURE:
<223> OTHER INFORMATION: Description of Artificial Sequence: Synthetic

```
            Peptide

<400> SEQUENCE: 48

Met Lys Ala Glu Met Asn Gly Ser Lys Leu Gly Arg Arg
1               5                   10

<210> SEQ ID NO 49
<211> LENGTH: 13
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 49

Ala Glu Met Asn Gly Ser Lys Leu Gly Arg Arg Ala Lys
1               5                   10

<210> SEQ ID NO 50
<211> LENGTH: 13
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 50

Met Asn Gly Ser Lys Leu Gly Arg Arg Ala Lys Pro Glu
1               5                   10

<210> SEQ ID NO 51
<211> LENGTH: 13
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 51

Gly Ser Lys Leu Gly Arg Arg Ala Lys Pro Glu Gly Ala
1               5                   10

<210> SEQ ID NO 52
<211> LENGTH: 13
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 52

Lys Leu Gly Arg Arg Ala Lys Pro Glu Gly Ala Leu Gln
1               5                   10

<210> SEQ ID NO 53
<211> LENGTH: 13
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 53

Gly Arg Arg Ala Lys Pro Glu Gly Ala Leu Gln Asn Asn
1               5                   10

<210> SEQ ID NO 54
```

```
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 54

Arg Ala Lys Pro Glu Gly Ala Leu Gln Asn Asn Asp Gly
1               5                   10

<210> SEQ ID NO 55
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 55

Lys Pro Glu Gly Ala Leu Gln Asn Asn Asp Gly Leu Tyr
1               5                   10

<210> SEQ ID NO 56
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 56

Glu Gly Ala Leu Gln Asn Asn Asp Gly Leu Tyr Asp Pro
1               5                   10

<210> SEQ ID NO 57
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 57

Ala Leu Gln Asn Asn Asp Gly Leu Tyr Asp Pro Asp Cys
1               5                   10

<210> SEQ ID NO 58
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 58

Gln Asn Asn Asp Gly Leu Tyr Asp Pro Asp Cys Asp Glu
1               5                   10

<210> SEQ ID NO 59
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 59
```

Asn Asp Gly Leu Tyr Asp Pro Asp Cys Asp Glu Ser Gly
1               5                   10

<210> SEQ ID NO 60
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 60

Gly Leu Tyr Asp Pro Asp Cys Asp Glu Ser Gly Leu Phe
1               5                   10

<210> SEQ ID NO 61
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 61

Tyr Asp Pro Asp Cys Asp Glu Ser Gly Leu Phe Lys Ala
1               5                   10

<210> SEQ ID NO 62
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 62

Pro Asp Cys Asp Glu Ser Gly Leu Phe Lys Ala Lys Gln
1               5                   10

<210> SEQ ID NO 63
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 63

Cys Asp Glu Ser Gly Leu Phe Lys Ala Lys Gln Cys Asn
1               5                   10

<210> SEQ ID NO 64
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 64

Glu Ser Gly Leu Phe Lys Ala Lys Gln Cys Asn Gly Thr
1               5                   10

<210> SEQ ID NO 65
<211> LENGTH: 13
<212> TYPE: PRT
<213> ORGANISM: Artificial Sequence
<220> FEATURE:

```
<223> OTHER INFORMATION: Description of Artificial Sequence:  Synthetic
      Peptide

<400> SEQUENCE: 65

Gly Leu Phe Lys Ala Lys Gln Cys Asn Gly Thr Ser Thr
1               5                   10

<210> SEQ ID NO 66
<211> LENGTH: 13
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 66

Phe Lys Ala Lys Gln Cys Asn Gly Thr Ser Thr Cys Trp
1               5                   10

<210> SEQ ID NO 67
<211> LENGTH: 13
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 67

Ala Lys Gln Cys Asn Gly Thr Ser Thr Cys Trp Cys Val
1               5                   10

<210> SEQ ID NO 68
<211> LENGTH: 13
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 68

Gln Cys Asn Gly Thr Ser Thr Cys Trp Cys Val Asn Thr
1               5                   10

<210> SEQ ID NO 69
<211> LENGTH: 13
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 69

Asn Gly Thr Ser Thr Cys Trp Cys Val Asn Thr Ala Gly
1               5                   10

<210> SEQ ID NO 70
<211> LENGTH: 13
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 70

Thr Ser Thr Cys Trp Cys Val Asn Thr Ala Gly Val Arg
1               5                   10
```

```
<210> SEQ ID NO 71
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 71

Thr Cys Trp Cys Val Asn Thr Ala Gly Val Arg Arg Thr
1               5                   10

<210> SEQ ID NO 72
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 72

Trp Cys Val Asn Thr Ala Gly Val Arg Arg Thr Asp Lys
1               5                   10

<210> SEQ ID NO 73
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 73

Val Asn Thr Ala Gly Val Arg Arg Thr Asp Lys Asp Thr
1               5                   10

<210> SEQ ID NO 74
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 74

Thr Ala Gly Val Arg Arg Thr Asp Lys Asp Thr Glu Ile
1               5                   10

<210> SEQ ID NO 75
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 75

Gly Val Arg Arg Thr Asp Lys Asp Thr Glu Ile Thr Cys
1               5                   10

<210> SEQ ID NO 76
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 76
```

```
Arg Arg Thr Asp Lys Asp Thr Glu Ile Thr Cys Ser Glu
1               5                   10

<210> SEQ ID NO 77
<211> LENGTH: 13
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 77

Thr Asp Lys Asp Thr Glu Ile Thr Cys Ser Glu Arg Val
1               5                   10

<210> SEQ ID NO 78
<211> LENGTH: 13
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 78

Lys Asp Thr Glu Ile Thr Cys Ser Glu Arg Val Arg Thr
1               5                   10

<210> SEQ ID NO 79
<211> LENGTH: 13
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 79

Thr Glu Ile Thr Cys Ser Glu Arg Val Arg Thr Tyr Trp
1               5                   10

<210> SEQ ID NO 80
<211> LENGTH: 13
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 80

Ile Thr Cys Ser Glu Arg Val Arg Thr Tyr Trp Ile Ile
1               5                   10

<210> SEQ ID NO 81
<211> LENGTH: 13
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 81

Cys Ser Glu Arg Val Arg Thr Tyr Trp Ile Ile Ile Glu
1               5                   10

<210> SEQ ID NO 82
<211> LENGTH: 13
<212> TYPE: PRT
<213> ORGANISM: Artificial Sequence
```

```
<220> FEATURE:
<223> OTHER INFORMATION: Description of Artificial Sequence: Synthetic
      Peptide

<400> SEQUENCE: 82

Glu Arg Val Arg Thr Tyr Trp Ile Ile Ile Glu Leu Lys
1               5                   10

<210> SEQ ID NO 83
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 83

Val Arg Thr Tyr Trp Ile Ile Ile Glu Leu Lys His Lys
1               5                   10

<210> SEQ ID NO 84
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 84

Thr Tyr Trp Ile Ile Ile Glu Leu Lys His Lys Ala Arg
1               5                   10

<210> SEQ ID NO 85
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 85

Trp Ile Ile Ile Glu Leu Lys His Lys Ala Arg Glu Lys
1               5                   10

<210> SEQ ID NO 86
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 86

Ile Ile Glu Leu Lys His Lys Ala Arg Glu Lys Pro Tyr
1               5                   10

<210> SEQ ID NO 87
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 87

Glu Leu Lys His Lys Ala Arg Glu Lys Pro Tyr Asp Ser
1               5                   10
```

```
<210> SEQ ID NO 88
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 88

Lys His Lys Ala Arg Glu Lys Pro Tyr Asp Ser Lys Ser
1               5                   10

<210> SEQ ID NO 89
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 89

Lys Ala Arg Glu Lys Pro Tyr Asp Ser Lys Ser Leu Arg
1               5                   10

<210> SEQ ID NO 90
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 90

Arg Glu Lys Pro Tyr Asp Ser Lys Ser Leu Arg Thr Ala
1               5                   10

<210> SEQ ID NO 91
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 91

Lys Pro Tyr Asp Ser Lys Ser Leu Arg Thr Ala Leu Gln
1               5                   10

<210> SEQ ID NO 92
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 92

Tyr Asp Ser Lys Ser Leu Arg Thr Ala Leu Gln Lys Glu
1               5                   10

<210> SEQ ID NO 93
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide
```

```
<400> SEQUENCE: 93

Ser Lys Ser Leu Arg Thr Ala Leu Gln Lys Glu Ile Thr
1               5                   10

<210> SEQ ID NO 94
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 94

Ser Leu Arg Thr Ala Leu Gln Lys Glu Ile Thr Thr Arg
1               5                   10

<210> SEQ ID NO 95
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 95

Arg Thr Ala Leu Gln Lys Glu Ile Thr Thr Arg Tyr Gln
1               5                   10

<210> SEQ ID NO 96
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 96

Ala Leu Gln Lys Glu Ile Thr Thr Arg Tyr Gln Leu Asp
1               5                   10

<210> SEQ ID NO 97
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 97

Gln Lys Glu Ile Thr Thr Arg Tyr Gln Leu Asp Pro Lys
1               5                   10

<210> SEQ ID NO 98
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 98

Glu Ile Thr Thr Arg Tyr Gln Leu Asp Pro Lys Phe Ile
1               5                   10

<210> SEQ ID NO 99
<211> LENGTH: 13
<212> TYPE: PRT
```

```
<213> ORGANISM: Artificial Sequence
<220> FEATURE:
<223> OTHER INFORMATION: Description of Artificial Sequence: Synthetic
      Peptide

<400> SEQUENCE: 99

Thr Thr Arg Tyr Gln Leu Asp Pro Lys Phe Ile Thr Ser
1               5                   10

<210> SEQ ID NO 100
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 100

Arg Tyr Gln Leu Asp Pro Lys Phe Ile Thr Ser Ile Leu
1               5                   10

<210> SEQ ID NO 101
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 101

Gln Leu Asp Pro Lys Phe Ile Thr Ser Ile Leu Tyr Glu
1               5                   10

<210> SEQ ID NO 102
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 102

Asp Pro Lys Phe Ile Thr Ser Ile Leu Tyr Glu Asn Asn
1               5                   10

<210> SEQ ID NO 103
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 103

Lys Phe Ile Thr Ser Ile Leu Tyr Glu Asn Asn Val Ile
1               5                   10

<210> SEQ ID NO 104
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 104

Ile Thr Ser Ile Leu Tyr Glu Asn Asn Val Ile Thr Ile
1               5                   10
```

```
<210> SEQ ID NO 105
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 105

Ser Ile Leu Tyr Glu Asn Asn Val Ile Thr Ile Asp Leu
1               5                   10

<210> SEQ ID NO 106
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 106

Leu Tyr Glu Asn Asn Val Ile Thr Ile Asp Leu Val Gln
1               5                   10

<210> SEQ ID NO 107
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 107

Glu Asn Asn Val Ile Thr Ile Asp Leu Val Gln Asn Ser
1               5                   10

<210> SEQ ID NO 108
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 108

Asn Val Ile Thr Ile Asp Leu Val Gln Asn Ser Ser Gln
1               5                   10

<210> SEQ ID NO 109
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 109

Ile Thr Ile Asp Leu Val Gln Asn Ser Ser Gln Lys Thr
1               5                   10

<210> SEQ ID NO 110
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide
```

```
<400> SEQUENCE: 110

Ile Asp Leu Val Gln Asn Ser Ser Gln Lys Thr Gln Asn
1               5                   10

<210> SEQ ID NO 111
<211> LENGTH: 13
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 111

Leu Val Gln Asn Ser Ser Gln Lys Thr Gln Asn Asp Val
1               5                   10

<210> SEQ ID NO 112
<211> LENGTH: 13
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 112

Gln Asn Ser Ser Gln Lys Thr Gln Asn Asp Val Asp Ile
1               5                   10

<210> SEQ ID NO 113
<211> LENGTH: 13
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 113

Ser Ser Gln Lys Thr Gln Asn Asp Val Asp Ile Ala Asp
1               5                   10

<210> SEQ ID NO 114
<211> LENGTH: 13
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 114

Gln Lys Thr Gln Asn Asp Val Asp Ile Ala Asp Val Ala
1               5                   10

<210> SEQ ID NO 115
<211> LENGTH: 13
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 115

Thr Gln Asn Asp Val Asp Ile Ala Asp Val Ala Tyr Tyr
1               5                   10

<210> SEQ ID NO 116
<211> LENGTH: 13
```

```
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 116

Asn Asp Val Asp Ile Ala Asp Val Ala Tyr Tyr Phe Glu
1               5                   10

<210> SEQ ID NO 117
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 117

Val Asp Ile Ala Asp Val Ala Tyr Tyr Phe Glu Lys Asp
1               5                   10

<210> SEQ ID NO 118
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 118

Ile Ala Asp Val Ala Tyr Tyr Phe Glu Lys Asp Val Lys
1               5                   10

<210> SEQ ID NO 119
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 119

Asp Val Ala Tyr Tyr Phe Glu Lys Asp Val Lys Gly Glu
1               5                   10

<210> SEQ ID NO 120
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 120

Ala Tyr Tyr Phe Glu Lys Asp Val Lys Gly Glu Ser Leu
1               5                   10

<210> SEQ ID NO 121
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 121

Tyr Phe Glu Lys Asp Val Lys Gly Glu Ser Leu Phe His
```

```
<210> SEQ ID NO 122
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 122

Glu Lys Asp Val Lys Gly Glu Ser Leu Phe His Ser Lys
1               5                   10

<210> SEQ ID NO 123
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 123

Asp Val Lys Gly Glu Ser Leu Phe His Ser Lys Lys Met
1               5                   10

<210> SEQ ID NO 124
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 124

Lys Gly Glu Ser Leu Phe His Ser Lys Lys Met Asp Leu
1               5                   10

<210> SEQ ID NO 125
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 125

Glu Ser Leu Phe His Ser Lys Lys Met Asp Leu Thr Val
1               5                   10

<210> SEQ ID NO 126
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 126

Leu Phe His Ser Lys Lys Met Asp Leu Thr Val Asn Gly
1               5                   10

<210> SEQ ID NO 127
<211> LENGTH: 13
<212> TYPE: PRT
<213> ORGANISM: Artificial Sequence
<220> FEATURE:
<223> OTHER INFORMATION: Description of Artificial Sequence: Synthetic
```

```
                              -continued

Peptide

<400> SEQUENCE: 127

His Ser Lys Lys Met Asp Leu Thr Val Asn Gly Glu Gln
1               5                   10

<210> SEQ ID NO 128
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 128

Lys Lys Met Asp Leu Thr Val Asn Gly Glu Gln Leu Asp
1               5                   10

<210> SEQ ID NO 129
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 129

Met Asp Leu Thr Val Asn Gly Glu Gln Leu Asp Leu Asp
1               5                   10

<210> SEQ ID NO 130
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 130

Leu Thr Val Asn Gly Glu Gln Leu Asp Leu Asp Pro Gly
1               5                   10

<210> SEQ ID NO 131
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 131

Val Asn Gly Glu Gln Leu Asp Leu Asp Pro Gly Gln Thr
1               5                   10

<210> SEQ ID NO 132
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 132

Gly Glu Gln Leu Asp Leu Asp Pro Gly Gln Thr Leu Ile
1               5                   10

<210> SEQ ID NO 133
```

```
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 133

Gln Leu Asp Leu Asp Pro Gly Gln Thr Leu Ile Tyr Tyr
1               5                   10

<210> SEQ ID NO 134
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 134

Asp Leu Asp Pro Gly Gln Thr Leu Ile Tyr Tyr Val Asp
1               5                   10

<210> SEQ ID NO 135
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 135

Asp Pro Gly Gln Thr Leu Ile Tyr Tyr Val Asp Glu Lys
1               5                   10

<210> SEQ ID NO 136
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 136

Gly Gln Thr Leu Ile Tyr Tyr Val Asp Glu Lys Ala Pro
1               5                   10

<210> SEQ ID NO 137
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 137

Thr Leu Ile Tyr Tyr Val Asp Glu Lys Ala Pro Glu Phe
1               5                   10

<210> SEQ ID NO 138
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 138
```

```
Ile Tyr Tyr Val Asp Glu Lys Ala Pro Glu Phe Ser Met
1               5                  10
```

<210> SEQ ID NO 139
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 139

```
Tyr Val Asp Glu Lys Ala Pro Glu Phe Ser Met Gln Gly
1               5                  10
```

<210> SEQ ID NO 140
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 140

```
Asp Glu Lys Ala Pro Glu Phe Ser Met Gln Gly Leu Lys
1               5                  10
```

<210> SEQ ID NO 141
<211> LENGTH: 321
<212> TYPE: DNA
<213> ORGANISM: Artificial Sequence
<220> FEATURE:
<223> OTHER INFORMATION: Description of Artificial Sequence: Synthetic
      Primer
<220> FEATURE:
<221> NAME/KEY: CDS
<222> LOCATION: (1)..(321)

<400> SEQUENCE: 141

```
gag ctc cag atg acc cag tct cca tcc tcc ctg tct gct tct gtg gga        48
Glu Leu Gln Met Thr Gln Ser Pro Ser Ser Leu Ser Ala Ser Val Gly
1               5                  10                  15 gac aga gtc acc atc act tgt cgg aca agt cag agc att agc agc tat        96
Asp Arg Val Thr Ile Thr Cys Arg Thr Ser Gln Ser Ile Ser Ser Tyr
        20                  25                  30 tta aat tgg tat cag cag aaa cca gga cag cct cct aag ctg ctc att       144
Leu Asn Trp Tyr Gln Gln Lys Pro Gly Gln Pro Pro Lys Leu Leu Ile
    35                  40                  45 tac tgg gca tct acc cgg gaa tcc ggg gtc cct gac cga ttc agt ggc       192
Tyr Trp Ala Ser Thr Arg Glu Ser Gly Val Pro Asp Arg Phe Ser Gly
50                  55                  60 agc ggg tct ggg aca gat ttc act ctc acc atc agc agt cta caa cct       240
Ser Gly Ser Gly Thr Asp Phe Thr Leu Thr Ile Ser Ser Leu Gln Pro
65                  70                  75                  80 gaa gat tct gca act tac tac tgt cag cag agt tac gac atc ccg tac       288
Glu Asp Ser Ala Thr Tyr Tyr Cys Gln Gln Ser Tyr Asp Ile Pro Tyr
                85                  90                  95 act ttt ggc cag ggg acc aag ctg gag atc aaa                           321
Thr Phe Gly Gln Gly Thr Lys Leu Glu Ile Lys
            100                 105
```

<210> SEQ ID NO 142
<211> LENGTH: 107
<212> TYPE: PRT
<213> ORGANISM: Artificial Sequence
<220> FEATURE:

<223> OTHER INFORMATION: Description of Artificial Sequence: Synthetic
      Peptide

<400> SEQUENCE: 142

Glu Leu Gln Met Thr Gln Ser Pro Ser Ser Leu Ser Ala Ser Val Gly
1               5                   10                  15

Asp Arg Val Thr Ile Thr Cys Arg Thr Ser Gln Ser Ile Ser Ser Tyr
            20                  25                  30

Leu Asn Trp Tyr Gln Gln Lys Pro Gly Gln Pro Pro Lys Leu Leu Ile
        35                  40                  45

Tyr Trp Ala Ser Thr Arg Glu Ser Gly Val Pro Asp Arg Phe Ser Gly
50                  55                  60

Ser Gly Ser Gly Thr Asp Phe Thr Leu Thr Ile Ser Ser Leu Gln Pro
65                  70                  75                  80

Glu Asp Ser Ala Thr Tyr Tyr Cys Gln Gln Ser Tyr Asp Ile Pro Tyr
                85                  90                  95

Thr Phe Gly Gln Gly Thr Lys Leu Glu Ile Lys
            100                 105

<210> SEQ ID NO 143
<211> LENGTH: 414
<212> TYPE: DNA
<213> ORGANISM: Artificial Sequence
<220> FEATURE:
<223> OTHER INFORMATION: Description of Artificial Sequence: Synthetic
      Primer
<220> FEATURE:
<221> NAME/KEY: CDS
<222> LOCATION: (1)..(414)

<400> SEQUENCE: 143 gag gtg cag ctg ctc gag tct ggg gga ggc gtg gtc cag cct ggg agg      48
Glu Val Gln Leu Leu Glu Ser Gly Gly Gly Val Val Gln Pro Gly Arg
1               5                   10                  15 tcc ctg aga ctc tcc tgt gca gcc tct gga ttc acc ttc agt agc tat      96
Ser Leu Arg Leu Ser Cys Ala Ala Ser Gly Phe Thr Phe Ser Ser Tyr
            20                  25                  30 ggc atg cac tgg gtc cgc cag gct cca ggc aag ggg ctg gag tgg gtg     144
Gly Met His Trp Val Arg Gln Ala Pro Gly Lys Gly Leu Glu Trp Val
        35                  40                  45 gca gtt ata tca tat gat gga agt aat aaa tac tat gca gac tcc gtg     192
Ala Val Ile Ser Tyr Asp Gly Ser Asn Lys Tyr Tyr Ala Asp Ser Val
50                  55                  60 aag ggc cga ttc acc atc tcc aga gac aat tcc aag aac acg ctg tat     240
Lys Gly Arg Phe Thr Ile Ser Arg Asp Asn Ser Lys Asn Thr Leu Tyr
65                  70                  75                  80 ctg caa atg aac agc ctg aga gct gag gac acg gct gtg tat tac tgt     288
Leu Gln Met Asn Ser Leu Arg Ala Glu Asp Thr Ala Val Tyr Tyr Cys
                85                  90                  95 gcg aaa gat atg ggg tgg ggc agt ggc tgg aga ccc tac tac tac tac     336
Ala Lys Asp Met Gly Trp Gly Ser Gly Trp Arg Pro Tyr Tyr Tyr Tyr
            100                 105                 110 ggt atg gac gtc tgg ggc caa ggg acc acg gtc acc gtc tcc tca gca     384
Gly Met Asp Val Trp Gly Gln Gly Thr Thr Val Thr Val Ser Ser Ala
115                 120                 125 ccc acc aag gct ccg gat gtg ttc cct cta                             414
Pro Thr Lys Ala Pro Asp Val Phe Pro Leu
130                 135

<210> SEQ ID NO 144
<211> LENGTH: 138

<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 144

Glu Val Gln Leu Leu Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Met Gly Trp Gly Ser Gly Trp Arg Pro Tyr Tyr Tyr Tyr
            100                 105                 110

Gly Met Asp Val Trp Gly Gln Gly Thr Thr Val Thr Val Ser Ser Ala
        115                 120                 125

Pro Thr Lys Ala Pro Asp Val Phe Pro Leu
    130                 135

<210> SEQ ID NO 145
<211> LENGTH: 372
<212> TYPE: DNA
<213> ORGANISM: Artificial Sequence
<220> FEATURE:
<223> OTHER INFORMATION: Description of Artificial Sequence: Synthetic
      Primer
<220> FEATURE:
<221> NAME/KEY: CDS
<222> LOCATION: (1)..(372)

<400> SEQUENCE: 145 gag gtg cag ctg ctc gag tct ggg gga gtc gtg gta cag cct ggg ggg      48
Glu Val Gln Leu Leu Glu Ser Gly Gly Val Val Val Gln Pro Gly Gly
1               5                   10                  15 tcc ctg aga ctc tcc tgt gca gcc tct gga ttc acc ttt gat gat tat     96
Ser Leu Arg Leu Ser Cys Ala Ala Ser Gly Phe Thr Phe Asp Asp Tyr
            20                  25                  30 gcc atg cac tgg gtc cgc cag gct cca ggc aag ggg ctg gag tgg gtg    144
Ala Met His Trp Val Arg Gln Ala Pro Gly Lys Gly Leu Glu Trp Val
        35                  40                  45 gca gtt ata tca tat gat gga agt aat aaa tac tat gca gac tcc gtg    192
Ala Val Ile Ser Tyr Asp Gly Ser Asn Lys Tyr Tyr Ala Asp Ser Val
    50                  55                  60 aag ggc cga ttc acc atc tcc aga gac aat tcc aag aac acg ctg tat    240
Lys Gly Arg Phe Thr Ile Ser Arg Asp Asn Ser Lys Asn Thr Leu Tyr
65                  70                  75                  80 ctg caa atg aac agc ctg aga gct gag gac acg gct gtg tat tac tgt    288
Leu Gln Met Asn Ser Leu Arg Ala Glu Asp Thr Ala Val Tyr Tyr Cys
                85                  90                  95 gcg aaa aag gaa ggc tac tgg ggc cag gga acc ctg gtc acc gtc tcc    336
Ala Lys Lys Glu Gly Tyr Trp Gly Gln Gly Thr Leu Val Thr Val Ser
            100                 105                 110 tca gca ccc acc aag gct ccg gat gtg ttc cct cta                    372
Ser Ala Pro Thr Lys Ala Pro Asp Val Phe Pro Leu <210> SEQ ID NO 146
<211> LENGTH: 124
<212> TYPE: PRT
<213> ORGANISM: Artificial Sequence
<220> FEATURE:
<223> OTHER INFORMATION: Description of Artificial Sequence: Synthetic Peptide

<400> SEQUENCE: 146

Glu Val Gln Leu Leu Glu Ser Gly Gly Val Val Gln Pro Gly Gly
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Lys Glu Gly Tyr Trp Gly Gln Gly Thr Leu Val Thr Val Ser
            100                 105                 110

Ser Ala Pro Thr Lys Ala Pro Asp Val Phe Pro Leu
        115                 120

<210> SEQ ID NO 147
<211> LENGTH: 321
<212> TYPE: DNA
<213> ORGANISM: Artificial Sequence
<220> FEATURE:
<223> OTHER INFORMATION: Description of Artificial Sequence: Synthetic Primer
<220> FEATURE:
<221> NAME/KEY: CDS
<222> LOCATION: (1)..(321)

<400> SEQUENCE: 147 gag ctc cag atg acc cag tct cca tcc tcc ctg tct gca tct gta gga        48
Glu Leu Gln Met Thr Gln Ser Pro Ser Ser Leu Ser Ala Ser Val Gly
1               5                   10                  15 gac aga gtc acc atc act tgc cgg gca agt cag agc att agc agc tat        96
Asp Arg Val Thr Ile Thr Cys Arg Ala Ser Gln Ser Ile Ser Ser Tyr
            20                  25                  30 tta aat tgg tat cag cag aaa cca gga cag cct cct aag ctg ctc att       144
Leu Asn Trp Tyr Gln Gln Lys Pro Gly Gln Pro Pro Lys Leu Leu Ile
        35                  40                  45 tac tgg gca tct acc cgg gaa tcc ggg gtc cct gac cga ttc agc ggc       192
Tyr Trp Ala Ser Thr Arg Glu Ser Gly Val Pro Asp Arg Phe Ser Gly
    50                  55                  60 agt gaa tct ggg aca aat tac act ctc acc atc agc agc ctg cag cct       240
Ser Glu Ser Gly Thr Asn Tyr Thr Leu Thr Ile Ser Ser Leu Gln Pro
65                  70                  75                  80 gaa gat ttt gct act tac ttt tgt caa cag tct gac agt ttg ccg atc       288
Glu Asp Phe Ala Thr Tyr Phe Cys Gln Gln Ser Asp Ser Leu Pro Ile
                85                  90                  95 acc ttc ggc caa ggg aca cga ctg gac att caa                           321
Thr Phe Gly Gln Gly Thr Arg Leu Asp Ile Gln
            100                 105

<210> SEQ ID NO 148
<211> LENGTH: 107
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 148

Glu Leu Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Gln Pro Pro Lys Leu Leu Ile
        35                  40                  45

Tyr Trp Ala Ser Thr Arg Glu Ser Gly Val Pro Asp Arg Phe Ser Gly
    50                  55                  60

Ser Glu Ser Gly Thr Asn Tyr Thr Leu Thr Ile Ser Ser Leu Gln Pro
65                  70                  75                  80

Glu Asp Phe Ala Thr Tyr Phe Cys Gln Gln Ser Asp Ser Leu Pro Ile
                85                  90                  95

Thr Phe Gly Gln Gly Thr Arg Leu Asp Ile Gln
            100                 105

<210> SEQ ID NO 149
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 149
aggtgcagct gctcgagtct gg                                          22

<210> SEQ ID NO 150
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 150
cagagtcacc ttgctcgagt ctgg                                        24

<210> SEQ ID NO 151
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 151
caggtgcagc tgctcgagtc ggg                                         23

<210> SEQ ID NO 152
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer

```
<400> SEQUENCE: 152
caggtgcagc tactcgagtg ggg                                              23

<210> SEQ ID NO 153
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 153
caggtacagc tgctcgagtc agg                                              23

<210> SEQ ID NO 154
<211> LENGTH: 29
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 154
tgccttactg tctctggcca gcggaagat                                        29

<210> SEQ ID NO 155
<211> LENGTH: 38
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 155
gagccgcacg agcccgagct ccagatgacc cagtctcc                              38

<210> SEQ ID NO 156
<211> LENGTH: 40
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 156
gagccgcacg agcccgagct cgtgattgac agcagtctcc                            40

<210> SEQ ID NO 157
<211> LENGTH: 39
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 157
gagccgcacg agcccgagct cgtgatgacc tcagtctcc                             39

<210> SEQ ID NO 158
<211> LENGTH: 38
<212> TYPE: DNA
<213> ORGANISM: Artificial Sequence
<220> FEATURE:
<223> OTHER INFORMATION: Description of Artificial Sequence: Synthetic
      Primer
```

```
<400> SEQUENCE: 158
gagccgcacg agcccgagct cacactcacg cagtctcc                              38

<210> SEQ ID NO 159
<211> LENGTH: 38
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 159
gagccgcacg agcccgagct cgtgctgact cagtctcc                              38

<210> SEQ ID NO 160
<211> LENGTH: 58
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 160
gcgccgtcta gaattaacac tctcccctgt tgaagctctt tgtgacgggc gaactcag        58

<210> SEQ ID NO 161
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 161
aattttgagc tcactcagcc ccac                                             24

<210> SEQ ID NO 162
<211> LENGTH: 27
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 162
tctgccgagc tccagcctgc ctccgtg                                          27

<210> SEQ ID NO 163
<211> LENGTH: 27
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 163
tctgtggagc tccagccgcc ctcagtg                                          27

<210> SEQ ID NO 164
<211> LENGTH: 33
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 164
```

```
tctgaagagc tccaggaccc tgttgtgtct gtg                                    33

<210> SEQ ID NO 165
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 165
cagtctgagc tcacgcagcc gccc                                              24

<210> SEQ ID NO 166
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 166
cagactgagc tcactcagga gccc                                              24

<210> SEQ ID NO 167
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 167
caggttgagc tcactcaacc gccc                                              24

<210> SEQ ID NO 168
<211> LENGTH: 27
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 168
caggctgagc tcactcagcc gtcttcc                                           27

<210> SEQ ID NO 169
<211> LENGTH: 30
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 169
cgccgtctag aattatgaac attctgtagg                                        30
```